(12) United States Patent
Lin et al.

(10) Patent No.: US 12,173,340 B2
(45) Date of Patent: Dec. 24, 2024

(54) ATTENUATED GLUTAMINE SYNTHETASE AS A SELECTION MARKER

(71) Applicant: AGENCY FOR SCIENCE, TECHNOLOGY AND RESEARCH, Singapore (SG)

(72) Inventors: Pao Chun Lin, Singapore (SG); Zhiwei Song, Singapore (SG)

(73) Assignee: AGENCY FOR SCIENCE, TECHNOLOGY AND RESEARCH, Singapore (SG)

(*) Notice: Subject to any disclaimer, the term of this patent is extended or adjusted under 35 U.S.C. 154(b) by 442 days.

(21) Appl. No.: 16/461,320

(22) PCT Filed: Nov. 16, 2017

(86) PCT No.: PCT/SG2017/050570
§ 371 (c)(1),
(2) Date: May 15, 2019

(87) PCT Pub. No.: WO2018/093331
PCT Pub. Date: May 24, 2018

(65) Prior Publication Data
US 2019/0352631 A1 Nov. 21, 2019

(30) Foreign Application Priority Data
Nov. 16, 2016 (SG) .............. 10201609619S

(51) Int. Cl.
| C12N 15/52 | (2006.01) |
| C12N 9/00  | (2006.01) |
| C12N 15/09 | (2006.01) |
| C12N 15/81 | (2006.01) |
| C12N 15/85 | (2006.01) |

(52) U.S. Cl.
CPC .............. *C12N 9/93* (2013.01); *C12N 15/52* (2013.01); *C12N 15/85* (2013.01); *C12N 2840/203* (2013.01); *C12Y 603/01002* (2013.01)

(58) Field of Classification Search
CPC .................................. C12N 9/93; C12N 15/85
See application file for complete search history.

(56) References Cited

U.S. PATENT DOCUMENTS

| 5,827,739 A     | 10/1998 | Wilson et al. |             |
| 8,952,217 B2 *  | 2/2015  | Puzio ................ | C12N 15/8247 800/288 |
| 11,384,140 B2 * | 7/2022  | Ketchem ............ | C07K 16/065 |
| 2005/0106580 A1 | 5/2005  | Enenkel et al. |             |
| 2012/0301919 A1 | 11/2012 | Yang et al. |             |

FOREIGN PATENT DOCUMENTS

| WO | WO-2008/116931 A2 | 10/2008 |
| WO | WO-2010/147462 A2 | 12/2010 |
| WO | WO-2011/077387 A1 | 6/2011 |
| WO | WO-2013/137583 A1 | 9/2013 |
| WO | WO-2014/133468 A1 | 9/2014 |
| WO | WO-2017/197098 A1 | 11/2017 |

OTHER PUBLICATIONS

Eisenberg et al., BBA, 1477, 122-145, 2000.*
Lin et al., "Attenuated Glutamine Synthetase as a Selection Marker in CHO Cells to Efficiently Isolate Highly Productive Stable Cells for the Production of Antibodies and Other Biologics", https://doi.org/10.1080/19420862.2019.1612690, published online Jun. 4, 2019, 13 pages.
Frieg et al., "Molecular Mechanisms of Glutamine Synthetase Mutations That Lead to Clinically Relevant Pathologies", PLOS Computational Biology, vol. 12, No. 2, Feb. 2, 2016, 28 pages.
Häberle et al., "Congenital Glutamine Deficiency With Glutamine Synthetase Mutations", The New England Journal of Medicine, vol. 353, No. 18, Nov. 3, 2005, pp. 1926-1933.
Dhalla et al., "Regeneration of Catalytic Activity of Glutamine Synthetase Mutants by Chemical Activation: Exploration of the Role of Arginines 339 and 359 in Activity", Protein Science, vol. 3, No. 3, Mar. 1994, pp. 476-481.
Crespo et al., "Mutational Analysis of Asp51 of Anabaena azollae Glutamine Synthetase. D51E Mutation Confers Resistance to the Active Site Inhibitors L-methionine-DL-sulfoximine and phosphinothricin", Eur J. Biochem., vol. 266, No. 3, Dec. 1999, pp. 1202-1209.
Van Blokland et al., "Methods to Create a Stringent Selection System for Mammalian Cell Lines", Cytotechnology, vol. 63, No. 4, Apr. 21, 2011, pp. 371-384.
Lin et al., "B-cell Display-based One-step Method to Generate Chimeric Human IgG Monoclonal Antibodies", Nucleic Acids Research, vol. 39, No. 3, 2011, 10 pages.
Fan et al., "Improving the Efficiency of CHO Cell Line Generation Using Glutamine Synthetase Gene Knockout Cells", Biotechnology and Bioengineering, vol. 109, No. 4, Apr. 2012, pp. 1007-1015.
Krajewski et al., "Crystal Structures of Mammalian Glutamine Synthetases Illustrate Substrate-Induced Conformational Changes and Provide Opportunities for Drug and Herbicide Design", J. Mol. Biol. vol. 375, 2008, pp. 217-228.
Lai et al., "Advances in Mammalian Cell Line Development Technologies for Recombinant Protein Production", Pharmaceuticals, vol. 6, 2013, pp. 579-603.
Search Report and Written Opinion in International Application No. PCT/SG2017/050570 dated Jan. 31, 2018, 11 pages.
Extended European Search Report in EP Application No. 17872008.2 dated May 4, 2020, 14 pages.
Lianchun et al., "The Use of Glutamine Synthetase as a Selection Marker: Recent Advances in Chinese Hamster Ovary Cell Line Generation Processes", Pharmaceutical Bioprocessing, vol. 1, No. 5, Dec. 1, 2013, pp. 487-502.

(Continued)

*Primary Examiner* — Maryam Monshipouri
(74) *Attorney, Agent, or Firm* — ArentFox Schiff; Daniel W. Clarke

(57) ABSTRACT

Disclosed is an expression vector comprising a polynucleotide encoding for a glutamine synthetase with reduced activity compared to a wild type glutamine synthetase. Also disclosed are host cells, methods for preparing stable cell line, methods of producing polypeptide of interest, and kits thereof.

5 Claims, 10 Drawing Sheets

Specification includes a Sequence Listing.

(56) References Cited

OTHER PUBLICATIONS

Lin et al., "Attenuated Glutamine Synthetase as a Selection Marker in CHO Cells to Efficiently Isolate Highly Productive Stable Cells for the Production of Antibodies and Other Biologics", Mabs, vol. 11, No. 5, Jul. 4, 2019, pp. 965-976.
Fisher et al., "Feedback-Resistant Mutations in Bacillus Subtilis Glutamine Synthetase are Clustered in the Active Site", Journal of Bacteriology, Aug. 15, 2006, pp. 5966-5974.
Xu et al., "Random Mutagenesis of Glutamine Synthetase From *Escherichia coli*: Correlation Between Structure, Activity, and Fitness", Journal of Fermentation and Bioengineering, Society of Fermentation Technology, JP, vol. 77, No. 3, Jan. 1, 1994, pp. 252-258.
Invitation to Respond to Written Opinion and Written Opinion in SG Application No. 11201904406U dated Nov. 9, 2020, 7 pages.
Haeberle et al., "Congenital Glutamine Deficiency with Glutamine Synthetase Mutations", N. Engl. J. Med., 353;18, Nov. 3, 2005, pp. 1926-1933.
Crespo et al., Mutational Analysis of Asp51 of Anabaena Azollae Glutamine Synthetase. D51E Mutation Confers Resistance to the Active Site Inhibitors L-methionine-DL-sulfoximine and Phosphinothricin, Eur. J. Biochem. vol. 266, 1999, pp. 1202-1209.
Dhalla et al., "Regeneration of Catalytic Activity of Glutamine Synthetase Mutants by Chemical Activation: Exploration of the Role of Arginines 339 and 359 in Activity", Protein Science, vol. 3, 1994, pp. 476-481.
Frieg et al., "Molecular Mechanisms of Glutamine Synthetase Mutations That Lead to Clinically Relevant Pathologies", PLOS Computational Biology, DOI:10.1371/journal.pcbi. 1004693, Feb. 2, 2016, 28 pages.
Office Action in Chinese Application No. 201780073752.2, dated Nov. 25, 2022, 12 pages.
Communication Pursuant to Article 94(3) EPC in EP Application No. 17872008.2 dated Dec. 7, 2022, 5 pages.
Second Office Action issued in Chinese Patent Application No. 201780073752.2, dated Jun. 14, 2023, 3 pages. (original and English translation).
Third Office Action in Chinese Application No. 201780073752.2 dated Oct. 20, 2023 (with English translation), 10 pages.
Written Opinion in Singapore Application No. 11201904406U dated Mar. 29, 2024, 4 pages (original and English translation).
Decision of Final Rejection in Chinese Application No. 201780073752.2 dated Mar. 21, 2024 and English langage translation, 14 pages (Original and English translation).

\* cited by examiner

Figure 7

ATTENUATED GLUTAMINE SYNTHETASE AS A SELECTION MARKER

CROSS-REFERENCE TO RELATED APPLICATIONS

This application claims the benefit of priority of Singapore provisional application No. 10201609619S, filed 16 Nov. 2016, the contents of it being hereby incorporated by reference in its entirety for all purposes.

FIELD OF THE INVENTION

The present invention generally relates to mutation or genetic engineering. In particular, the present invention relates to expression vectors and methods for selecting the vector-containing host using markers.

BACKGROUND OF THE INVENTION

In the field of stable cell line development for biologic production, there is a need to select for cells that are high producers and yet stable at the same time. An example of a selection system used in the art is glutamine synthetase (GS) selection system. In certain cells typically used for stable cell line development, the glutamine synthetase (GS) has been inactivated. As such, these cells cannot synthesize glutamine on their own and can only survive and grow if glutamine is added into the culture medium. Therefore, the GS gene has been widely used in expression vectors as a positive selection marker. Thus, only cells that have incorporated expression vectors comprising GS gene will survive when glutamine is removed from the culture medium. Additionally, besides removing glutamine from the culture medium, to ensure that only high producer cells survive, a GS inhibitor will also be added. Addition of a GS inhibitor may amplify the copy number of the expression cassette in the chromosome because GS activity is inhibited. Thus, only the cells with higher copy number of GS gene can survive a GS inhibitor treatment.

Using the method described above, in order to ultimately obtain cell lines that are stable and high producers, hundreds of single clones need to be isolated to determine their productivity. Their stability upon a GS inhibitor removal also has to be assessed over at least 60 generations. This is a labor intensive and time consuming process.

In view of the above, in order to streamline the process of generating stable cell line, there is a need to provide an alternative expression vector comprising a polynucleotide encoding for an alternative glutamine synthetase.

SUMMARY OF THE INVENTION

In one aspect, there is provided an expression vector comprising a polynucleotide encoding for a glutamine synthetase with reduced activity compared to a wild type glutamine synthetase. In one embodiment, the expression vector further comprising at least one polynucleotide encoding for a polypeptide of interest. In another embodiment, the glutamine synthetase with reduced activity comprises one or more mutations as compared to a wild type glutamine synthetase. In yet another embodiment, the glutamine synthetase with reduced activity comprises one or more mutations in the glutamate binding region, the ATP binding region and/or the ammonia binding region. In yet another embodiment, (i) the mutation in the glutamate binding region is of at least one amino acid at the position selected from the group consisting of 134, 136, 196, 203, 248, 249, 253, 299, 319, 338, and 340 of a glutamine synthetase; or (ii) the mutation in the ammonia binding region is of at least one amino acid at the position selected from the group consisting of 63, 66, 162, and 305 of a glutamine synthetase; or (iii) the mutation in the ATP binding region is of at least one amino acid at the position selected from the group consisting of 192, 255, 257, 262, 333, 336, and 324 of a glutamine synthetase; wherein the glutamine synthetase has the amino acid sequence shown in SEQ ID NO: 1, SEQ ID NO: 2, SEQ ID NO: 3, or SEQ ID NO:4. In yet another embodiment, the mutation is of at least one amino acid at the position selected from the group consisting of 12, 19, 63, 66, 91, 116, 134, 136, 160, 162, 172, 176, 181, 192, 194, 196, 198, 199, 203, 230, 248, 249, 253, 255, 257, 260, 262, 271, 299, 305, 319, 336, 338, 333, 340, 324 and 341 of a glutamine synthetase, wherein the glutamine synthetase has the amino acid sequence shown in SEQ ID NO: 1, SEQ ID NO: 2, SEQ ID NO: 3, or SEQ ID NO:4. In yet another embodiment, the mutation is a substitution. In yet another embodiment, the mutation in the glutamine synthetase is selected from the group consisting of R324C, R341C, D63A, S66A, E134A, E136A, Y162A, G192A, E196A, E203A, N248A, G249A, H253A, N255A, S257A, R262A, R299A, E305A, R319A, R324A, Y336A, E338A, K333A, R340A, and R341A of a glutamine synthetase, wherein the glutamine synthetase has the amino acid sequence shown in SEQ ID NO: 1, SEQ ID NO: 2, SEQ ID NO: 3, or SEQ ID NO:4.

In yet another embodiment, the polynucleotide encoding for a glutamine synthetase with reduced activity is operatively linked to a promoter. In yet another embodiment, only one of the at least one polynucleotide encoding for a polypeptide of interest is operatively linked to a promoter. In yet another embodiment, the polynucleotide encoding for a glutamine synthetase with reduced activity compared to a wild type glutamine synthetase is not linked to a promoter. In yet another embodiment, the polypeptide of interest is selected from the group consisting of a recombinant protein and a part thereof, a fusion protein and a part thereof, an antibody and a part thereof. In yet another embodiment, the polypeptide of interest is the heavy chain of an antibody of interest and/or light chain of an antibody of interest. In yet another embodiment, the expression vector comprises two polynucleotides each encoding for a polypeptide of interest, wherein one of the polynucleotides encodes for the light chain of an antibody of interest, and one of the polynucleotides encodes for the heavy chain of the same antibody of interest. In yet another embodiment, the polynucleotide encoding for the light chain of an antibody of interest and the polynucleotide encoding for the heavy chain of the same antibody of interest are separated by polynucleotides encoding an internal ribosome entry site (IRES). In yet another embodiment, the polynucleotide encoding for the heavy chain of an antibody of interest is separated from the polynucleotide encoding for a glutamine synthetase with reduced activity by polynucleotide encoding an internal ribosome entry site (IRES). In yet another embodiment, the polynucleotide encoding the internal ribosome entry site separating the polynucleotide encoding for the light chain of an antibody of interest and the polynucleotide encoding for the heavy chain of the same antibody of interest is polynucleotide encoding a wild type internal ribosome entry site (IRES), and wherein the internal ribosome entry site separating the polynucleotide encoding for the heavy chain of an antibody of interest from the polynucleotide encoding for a glutamine synthetase with reduced activity is polynucleotide encoding an internal ribosome entry site with attenuated translation efficiency (IRESatt).

In another aspect, there is provided a host cell comprising the expression vector as described herein. In yet another aspect, there is provided a method for preparing stable cell line, comprising: (a) transforming a host cell having no glutamine synthetase activity with the expression vector as described herein; and (b) culturing the transformed host cell in a medium that selectively allows the proliferation of the transformed host cells comprising an amplified number of copies of the vector to be selected.

In yet another aspect, there is provided a method of producing polypeptide of interest, comprising: (a) transforming a host cell having no glutamine synthetase activity with the expression vector as described herein; (b) culturing the transformed host cell in a medium that selectively allows the production of polypeptide of interest; and (c) collecting the polypeptide of interest from the medium of (b). In yet another embodiment, the medium is a glutamine free cell culture medium. In yet another embodiment, the method does not comprise the use of a glutamine synthetase inhibitor, optionally wherein the glutamine synthetase inhibitor is methionine sulphoximine (MSX).

In yet another aspect, there is provided a kit comprising the expression vector as described herein. In yet another embodiment, the kit further comprises at least one of the following: (i) a host cell having no glutamine synthetase activity compared to a wild type cell; and (ii) a transfection medium or means to carry out a transfection. In yet another embodiment, the kit further comprises a glutamine free cell culture medium.

BRIEF DESCRIPTION OF THE DRAWINGS

The invention will be better understood with reference to the detailed description when considered in conjunction with the non-limiting examples and the accompanying drawings, in which:

FIG. 1 shows a pair of line graphs depicting amount of antibodies produced using CHOK1 GF$^{-/-}$ GS$^{-/-}$ cells that are transfected with either Tricistronic mAb-GS (SEQ ID NO: 14) or Tricistronic mAb-GSatt (R324C) (SEQ ID NO: 85) in minipools format. FIG. 1 illustrates that for production of both Antibody A and Antibody B, the amount of antibody produced using Tricistronic mAb-GSatt (R324C) is higher than the amount of antibody produced using Tricistronic mAb-GS.

FIG. 2 shows a pair of bar graphs depicting amount of antibodies titer (mAb titer) produced using CHOK1 GFT$^{-/-}$ GS$^{-/-}$ cells that are transfected with either Tricistronic mAb-GS (SEQ ID NO: 14) or Tricistronic mAb-GSatt (R324C) (SEQ ID NO: 85) in stable suspension pool format. For preliminary analysis, the WT GS system (i.e. CHOK1 GF$^{-/-}$ GS$^{-/-}$ cells that are transfected with Tricistronic mAb-GS) and attenuated GS system (i.e. CHOK1 GF$^{-/-}$ GS$^{-/-}$ cells that are transfected with mAb-GSatt (R324C)) were compared directly in the absence of glutamine for a fair comparison. Thus, the WT GS pools were not treated with MSX. FIG. 2 illustrates that amount of mAb titer produced using Tricistronic mAb-GSatt (R324C) is higher than amount of mAb titer produced using Tricistronic mAb-GS.

FIG. 3 illustrates that batch culture mAb titer in stable pools transfected with the mutant GS (i.e. bicistronic mAb-GSatt (R324C)) are generally higher than those WT GS pools (regardless whether the WT GS pools is treated with MSX (25 μM) or not).

FIG. 4 depicts the GS activities of WT GS and GS mutants that have been blanked using the cell lysate of untransfected CHO GS$^{-/-}$ cells and expression normalized using their luciferase activity. The GS activities of GS mutants in FIG. 4 are represented as fold-change over the GS activity of WT GS. Thus, FIG. 4 shows that several sites on the GS, when mutated from any amino acid to alanine, would attenuate the GS activity.

FIG. 5 illustrates that almost all the single clones (more than 95%) are above the stability level of 70%, which signifies that more than 95% of the single clones are stable.

FIG. 6 shows a pair of graphical illustrations depicting expression vector maps. FIG. 6 shows examples of the map of expression vector as described herein.

FIG. 7 shows a sequence alignment comparing GS protein sequences from four different species, namely Chinese hamster (labeled as "XP_003502909-CHO"; SEQ ID NO: 2), mouse (labeled as "NP_032157-mouse"; SEQ ID NO: 3), rat (labeled as "NP_058769-rat"; SEQ ID NO: 4), and human (labeled as "NP_0025056-human"; SEQ ID NO: 1). The line titled "consensus" shows the amino acid residues that are conserved among all four of the species. The arrows indicate the location of the point mutation that will be introduced to the WT GS. The type point mutation for each number is listed on Table 1. The dotted arrows indicate the location of the known human congenital disease mutations. Thus, FIG. 7 shows that the GS protein sequences among the four species listed are highly conserved. The percent sequence similarity of the GS protein sequences of Chinese hamster to mouse is 97%, the percent sequence similarity of the GS protein sequences of Chinese hamster to rat is 96%, and the percent sequence similarity of the GS protein sequences of Chinese hamster to human is 94%.

FIG. 8 illustrates that the average mAb titers generated using GS mutants—Gsm1, Gsm19 and R324C as selection markers are higher than the average mAb titers generated using WT GS as selection markers.

FIG. 9 shows that only two out of five GSwt clones were stable (i.e. maintained at least 70% of its original titer level) whereas four out of five GSm16 clones were stable.

FIG. 10 shows that mutation on multiple residues on the GS would attenuate the GS activity.

DETAILED DESCRIPTION OF THE PRESENT INVENTION

Figure 1A:
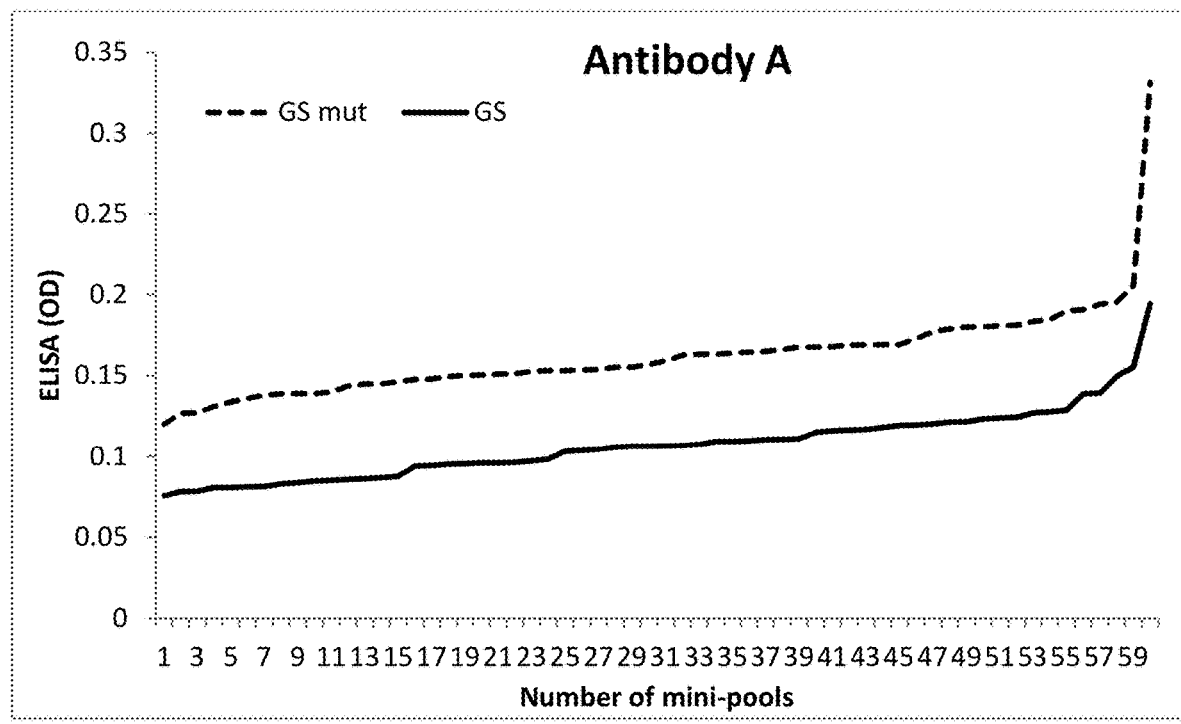
FIG. 1A depicts the experimental result for Antibody A and FIG. 1B depicts the experimental result for Antibody B. Thus.

In certain mammalian cells, particularly the Chinese hamster ovary (CHO) cells, the glutamine synthetase (GS) has been inactivated. As such, these cells cannot synthesize glutamine on their own and can only survive and grow if glutamine is added into the culture medium. Therefore, the GS gene has been widely used in expression vectors as a positive selection marker. In the field of stable cell line development for biologic production, there is a need to select for cells that are high producers and yet stable at the same time. Typically, when using the GS selection system, this is achieved by using methionine sulphoximine (MSX) to amplify the copy number of the expression cassette in the chromosome because MSX inhibits the GS activity; only the cells with higher copy number of GS can survive MSX treatment. Currently, hundreds of single clones need to be isolated to determine their productivity and their stability over at least 60 generations is assessed upon MSX removal. This is a labor intensive and time consuming process. In view of the above problems, there is a need to provide an alternative expression vector comprising a polynucleotide encoding for an alternative glutamine synthetase.

The inventors of the present disclosure have found an alternative expression vector comprising a polynucleotide encoding for an alternative glutamine synthetase, namely the GSatt system. The present invention entails the creation of a series of mutated GS gene as selection markers. The mutated GS, carries a reduced GS activity compared to the normal GS. When the attenuated GS (GSatt) is used as the selection marker for producing recombinant biologics in stably transfected cells, only the cells with the expression vector inserted into highly transcriptionally active site or the cells having several copies of the expression vectors inserted into less active site to compensate for the loss of GS activity can survive the selection. Often, the productivity of the recombinant biologics in these cells is higher because the nucleotide sequences encoding the recombinant biologics are also located in a highly transcriptionally active site or because there are multiple copies of nucleotide sequences encoding the recombinant biologics. Therefore, attenuated selection markers help to increase the selection stringency and increase the chance to identify high producers in a relatively small number stably transfected cells. Additionally, by using the GSatt system, the need to use glutamine synthetase inhibitor such as MSX can be eliminated and the stability can be enhanced as the GSatt marker provides a consistent selection pressure thereby saving effort and time in the generation of stable cell lines. Thus, in one aspect, the present invention provides an expression vector comprising a polynucleotide encoding for a glutamine synthetase with reduced activity compared to a wild type glutamine synthetase. As used herein, an expression vector generally refers to a plasmid or virus designed for gene expression in cells. The vector is used to introduce a specific gene into a target cell, and can commandeer the cell's mechanism for polypeptide synthesis to produce the polypeptide encoded by the gene. As used herein, the term "reduced activity" refers to the decrease in the ability of a mutated enzyme (such as glutamine synthetase) in synthesizing a product (such as glutamine) when compared to wild type enzyme. The activity of an enzyme having reduced activity is about 90%, or about 80%, or about 70%, or about 60%, or about 50%, or about 40%, or about 30%, or about 20%, or about 10%, or about 9%, or about 8%, or about 7%, or about 6%, or about 5%, or about 4%, or about 3%, or about 2%, or about 1.9%, or about 1.8%, or about 1.7%, or about 1.6%, or about 1.5%, or about 1.4%, or about 1.3%, or about 1.2%, or about 1.1%, or about 1%, or about 0.9%, or about 0.8%, or about 0.7%, or about 0.6%, or about 0.5%, or about 0.4%, or about 0.3%, or about 0.2%, or about 0.1% of the activity of a wild type enzyme. In one example, the activity of an enzyme having reduced activity is about 1.6%, of the activity of a wild type enzyme. In other words, if the activity of a wild type enzyme is considered as 100%, the activity of the mutated enzyme (or the enzyme having reduced activity) is reduced by about 10%, or about 20%, or about 30%, or about 40%, or about 50%, or about 60%, or about 70%, or about 80%, or about 90%, or about 91%, or about 92%, or about 93%, or about 94%, or about 95%, or about 96%, or about 97%, or about 98%, or about 98.1%, or about 98.2%, or about 98.3%, or about 98.4%, or about 98.5%, or about 98.6%, or about 98.7%, or about 98.8%, or about 98.9%, or about 99%, or about 99.1%, or about 99.2%, or about 99.3%, or about 99.4%, or about 99.5%, or about 99.6%, or about 99.7%, or about 99.8%, or about 99.9% when compared to the activity of a wild type enzyme. In one example, the activity of the mutated enzyme (or the enzyme having reduced activity) is reduced by about 98.4% when compared to the activity of a wild type enzyme. In one example, the average reduction of the mutated glutamine synthetase such as R324C mutant, D63A mutant, and E305 mutant is about 98.4% when compared to the activity of a wild type glutamine synthetase. In one example, the glutamine synthetase with reduced activity compared to a wild type glutamine synthetase or the glutamine synthetase expressed using the expression vector described herein is a recombinant glutamine synthetase. As used herein, the term "recombinant glutamine synthetase" refers to a polypeptide (such as glutamine synthetase) that results from the expression of recombinant DNA (such as expression vector described herein) within living cells (such as host cells).

In one example, the glutamine synthetase with reduced activity encoded by the expression vector described herein comprises one or more mutations as compared to a wild type glutamine synthetase. As used herein, the term "wild type glutamine synthetase" refers to a typical form of glutamine synthetase that occurs in nature. A wild type glutamine synthetase typically comprises of two major domains, namely the beta grasp domain (from amino acid residue at position 30 to amino acid residue at position 104 in a wild type glutamine synthetase) and the catalytic domain (from amino acid residue at position 134 to amino acid residue at position 351 in a wild type glutamine synthetase). As shown for example on FIG. 7, some of the amino acid residues that are involved in ATP, glutamate or ammonia binding are located within either the beta grasp domain or the catalytic domain. Amino acid sequence of wild type glutamine synthetase sequences from are listed as SEQ ID NO: 1 (wild type human GS sequence), SEQ ID NO: 2 (wild type Chinese hamster GS sequence), SEQ ID NO: 3 (wild type mouse GS sequence), and SEQ ID NO: 4 (wild type rat GS sequence). As used herein, the term "mutation" refers to a nucleotide sequence change in an isolated nucleic acid. The nucleotide sequence change includes, but is not limited to, a missense mutation, a nonsense mutation, a nucleotide substitution, a nucleotide deletion, a nucleotide insertion, nucleotide duplication, a frameshift mutation, a repeat expansion, and the like. However, the mutation cannot include a mutation that completely inactivates the activity of an enzyme (such as glutamine synthetase). An isolated nucleic acid that bears a mutation has a nucleic acid sequence that is statistically different in sequence from a homologous nucleic acid isolated from a corresponding wild-type population. In one example, the mutation may be a substitution or a deletion. A person skilled in the art appreciate that in order to express a GS comprising at least one mutation or a mutated GS, the sequences of the polynucleotide that are used to express the wild type GS has to be altered. Any method known in the art to alter the sequences of the polynucleotide can be used. In one example, the mutation is introduced via site directed mutagenesis. Site directed mutagenesis is performed by determining the target to be mutated and by using primers suitable for introducing the mutation (as shown for example in Table 2).

In order to be able to obtain a glutamine synthetase with reduced activity compared to a wild type glutamine synthetase, the locations of the mutations have to be determined. Thus, in one example, the glutamine synthetase with reduced activity comprises one or more mutations in the glutamate binding region, the ATP binding region and/or the ammonia binding region. A person skilled in the art appreciate that protein such as glutamine synthetase comprises multiple amino acid residues that form a polypeptide chain (also known as primary structure of a protein). Due to interactions between amino acid residues in the polypeptide chain, the polypeptide chain folds and forms three-dimensional structure (also known as tertiary structure of a protein). Therefore, the term "binding region" as used herein does not necessarily refer to a series of amino acid residues that are consecutively linked (or that are located next to each other) in a polypeptide chain. That is, amino acid residues that are part of a certain binding region can be located away from each other within the polypeptide chain. However, those amino acid residues may actually be located near to each other in the three-dimensional structure of the protein and thereby forming a binding region. For example, amino acid residues that are part of the ammonia binding region are located at positions 63, 66, 162, and 305 of the polypeptide chain of a glutamine synthetase, amino acid residues that are part of the glutamate binding region are located at positions 134, 136, 196, 203, 248, 249, 253, 299, 319, 338, and 340 of the polypeptide chain of a glutamine synthetase, and amino acid residues that are part of the ATP binding region are located at positions 192, 255, 257, 262, 324, 333, and 336 of the polypeptide chain of a glutamine synthetase.

As illustrated for example in Table 1, in one example, wherein when the mutation is in the glutamate binding region, the mutation of one, or at least one, or at least two, or at least three, or at least four, or at least five, or at least six, or at least seven, or at least eight, or at least nine, or at least 10, or all of the amino acid(s) is made at a position that includes, but are not limited to, position 134, 136, 196, 203, 248, 249, 253, 299, 319, 338, 340, and the like of a glutamine synthetase, wherein the glutamine synthetase has the amino acid sequence shown in SEQ ID NO: 1, SEQ ID NO: 2, SEQ ID NO: 3 or SEQ ID NO:4. In one example, wherein when the mutation is in the glutamate binding region, the mutation of one amino acid is made at a position that includes, but are not limited to, position 134, 136, 196, 203, 248, 249, 253, 299, 319, 338, 340, and the like of a glutamine synthetase, wherein the glutamine synthetase has the amino acid sequence shown in SEQ ID NO: 1, SEQ ID NO: 2, SEQ ID NO: 3 or SEQ ID NO:4. As illustrated for example in Table 1, in one example, wherein when the mutation is in the ammonia binding region, the mutation of one, or at least one, or at least two, or at least three, or all of the amino acid(s) is made at a position that includes, but are not limited to, position 63, 66, 162, 305, and the like of a glutamine synthetase, wherein the glutamine synthetase has the amino acid sequence shown in SEQ ID NO: 1, SEQ ID NO: 2, SEQ ID NO: 3 or SEQ ID NO:4. In one example, wherein when the mutation is in the ammonia binding region, the mutation of one amino acid is made at a position that includes, but are not limited to, position 63, 66, 162, 305, and the like of a glutamine synthetase, wherein the glutamine synthetase has the amino acid sequence shown in SEQ ID NO: 1, SEQ ID NO: 2, SEQ ID NO: 3 or SEQ ID NO:4. As illustrated for example in Table 1, in one example, wherein when the mutation is in the ATP binding region, the mutation of one, or at least one, or at least two, or at least three, or at least four, or at least five, or all of the amino acid(s) is made at a position that includes, but are not limited to, position 192, 255, 257, 262, 333, 336, 324 and the like of a glutamine synthetase, wherein the glutamine synthetase has the amino acid sequence shown in SEQ ID NO: 1, SEQ ID NO: 2, SEQ ID NO: 3 or SEQ ID NO:4. In one example, wherein when the mutation is in the ATP binding region, the mutation of one amino acid is made at a position that includes, but are not limited to, position 192, 255, 257, 262, 336, 324 and the like of a glutamine synthetase, wherein the glutamine synthetase has the amino acid sequence shown in SEQ ID NO: 1, SEQ ID NO: 2, SEQ ID NO: 3 or SEQ ID NO:4. In one example, the mutation is of at least one amino acid.

Figure 7:
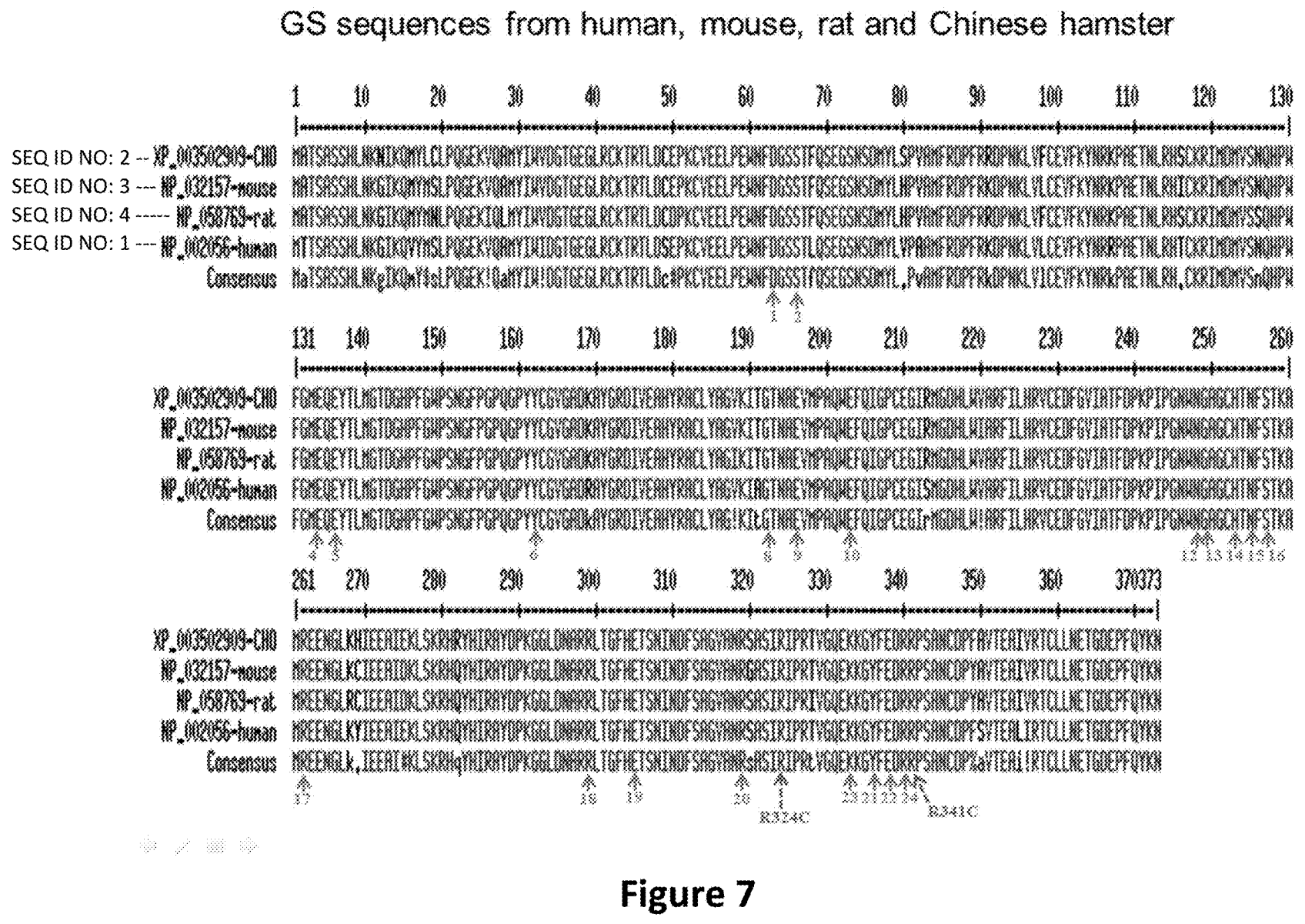

As illustrated for example in FIG. 7, the mutation of at least one amino acid is made at a position wherein there is a consensus among the wild type GS sequences from Chinese hamster (SEQ ID NO: 2), mouse (SEQ ID NO: 3), rat (SEQ ID NO: 4), and human (SEQ ID NO: 1). Thus, in one example, the mutation of one, or at least one, or at least two, or at least three, or at least four, or at least five, or at least six, or at least seven, or at least eight, or at least nine, or at least 10, or at least 11, or at least 12, or at least 13, or at least 14, or at least 15, or at least 16, or at least 17, or at least 18, or at least 19, or at least 20, or at least 21, or at least 22, or all of the amino acid(s) is made at a position that includes, but are not limited to, position 12, 19, 63, 66, 91, 116, 134, 136, 160, 162, 172, 176, 181, 192, 194, 196, 198, 199, 203, 230, 248, 249, 253, 255, 257, 260, 262, 271, 299, 305, 319, 336, 338, 333, 340, 324, 341, and the like of a glutamine synthetase, wherein the glutamine synthetase has the amino acid sequence shown in SEQ ID NO: 1, SEQ ID NO: 2, SEQ ID NO: 3 or SEQ ID NO:4. In one example, the mutation of one amino acid is made at a position that includes, but are not limited to, position 12, 19, 63, 66, 91, 116, 134, 136, 160, 162, 172, 176, 181, 192, 194, 196, 198, 199, 203, 230, 248, 249, 253, 255, 257, 260, 262, 271, 299, 305, 319, 336, 338, 333, 340, 324, 341, and the like of a glutamine synthetase, wherein the glutamine synthetase has the amino acid sequence shown in SEQ ID NO: 1, SEQ ID NO: 2, SEQ ID NO: 3 or SEQ ID NO:4. Without wishing to be bound by theory, the inventors of the present invention have specifically chosen to introduce one or more mutation at the positions listed above because the amino acid residues at those positions are conserved. Additionally, they are also involved in the binding of ammonia (such as amino acid residues at positions 63, 66, 162, and 305 of a glutamine synthetase), glutamate (such as amino acid residues at positions 134, 136, 196, 203, 248, 249, 253, 299, 319, 338, and 340 of a glutamine synthetase), or ATP (such as amino acid residues at positions 192, 255, 257, 262, 324, and 336 of a glutamine synthetase). The inventors have surprisingly found that amino acid residues that are conserved and that are involved in ammonia, glutamate, or ATP binding may be critical for GS activity.

Furthermore, the inventors have also surprisingly found that the amino acid positions listed herein are crucial to the activity of the GS such that substitution of these important sites would attenuate the GS activity. In one example, the mutation in the glutamine synthetase includes, but is not limited to, R324C, R341C, D63A, S66A, E134A, E136A, Y162A, G192A, E196A, E203A, N248A, G249A, H253A, N255A, S257A, R262A, R299A, E305A, R319A, R324A, Y336A, E338A, K333A, R340A, and R341A of a glutamine synthetase, wherein the glutamine synthetase has the amino acid sequence shown in SEQ ID NO: 1, SEQ ID NO: 2, SEQ ID NO: 3 or SEQ ID NO:4. In one example, to reduce its activity, the glutamine synthetase is mutated by substituting or replacing certain amino acids using alanine (A). Without wishing to be bound by theory, alanine (A) is chosen for the substitution or replacement of certain amino acid residues because alanine (A) eliminates the side chain of an amino acid residue beyond the beta carbon and it does not exerts extreme electrostatic and/or steric effect. Thus, a person skilled in the art appreciates that the substitution or replacement of certain amino acid residues in order to reduce glutamine synthetase activity can be performed using any amino acid amino acid residue that does not have extreme electrostatic and/or steric effect. In one example, the mutation in the glutamine synthetase wherein a certain amino acid is replaced by alanine (A) includes, but is not limited to, D63A, S66A, E134A, E136A, Y162A, G192A, E196A, E203A, N248A, G249A, H253A, N255A, S257A, R262A, R299A, E305A, R319A, R324A, Y336A, E338A, K333A, R340A, and R341A of a glutamine synthetase, wherein the glutamine synthetase has the amino acid sequence shown in SEQ ID NO: 1, SEQ ID NO: 2, SEQ ID NO: 3 or SEQ ID NO:4.

In order for the expression vector described herein to be able to express the glutamine synthetase with reduced activity, a promoter is required. As used herein, the term "promoter" refers to polynucleotide sequences (such as DNA sequences) that define where transcription of a gene by RNA polymerase begins. Promoter sequences are typically located directly upstream or at the 5' end of the transcription initiation site. Thus, in one example, in the expression vector as described herein, the polynucleotide encoding for a glutamine synthetase with reduced activity is operatively linked to a promoter. In one example, the promoter is at the 5' direction of the polynucleotide encoding for a glutamine synthetase with reduced activity. As used herein, the term "operatively linked" is intended to mean that the two polynucleotides are connected in a manner such that each polynucleotide can serve its intended function. In one example, two polynucleotides that are operatively linked are connected by a polynucleotide linker having length of up to 10 bp, or up to 20 bp, or up to 30 bp, or up to 40 bp, or up to 50 bp, or up to 60 bp, or up to 70 bp, or up to 80 bp, or up to 90 bp, or up to 100 bp, or up to 110 bp, or up to 120 bp, or up to 130 bp, or up to 140 bp, or up to 150 bp. In one example, both polynucleotides can be transcribed and the product of the transcription can then be translated into polynucleotide.

Figure 6A:
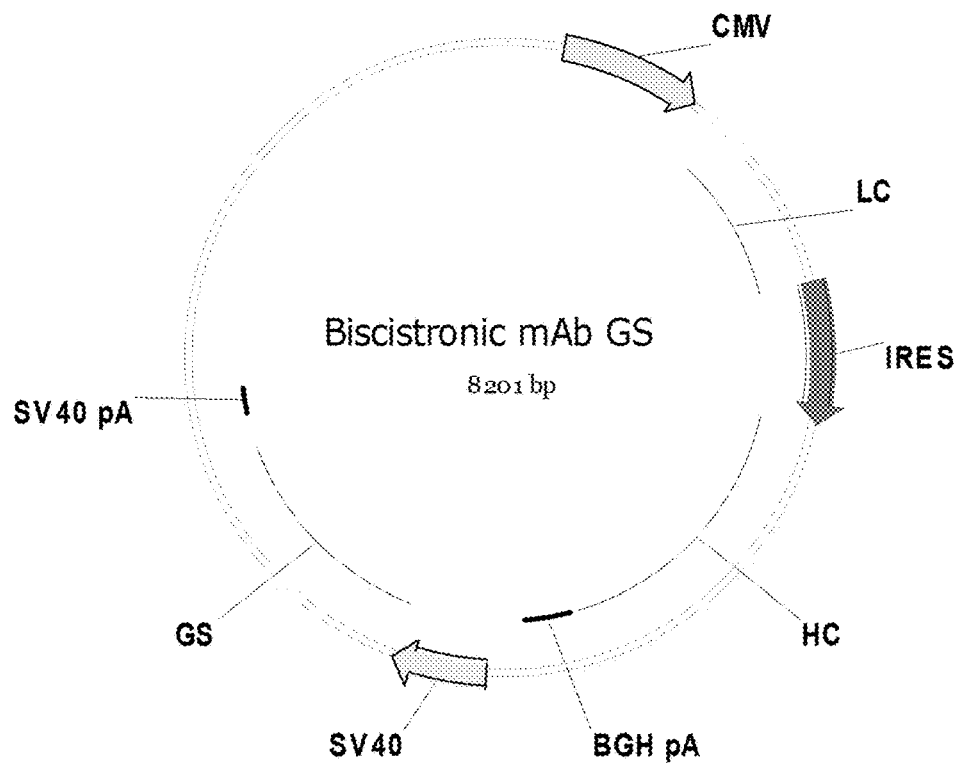
FIG. 6A depicts the expression vector map of bicistronic mAb GS. The full length sequence that corresponds to bicistronic mAb GS is listed as SEQ ID NO: 5. Sequences that correspond to specific regions of the expression vector map of bicistronic mAb GS are listed as SEQ ID NOs: 6 to 13.

As described above, the expression vector described herein can be used for generating a stable cell lines that can produce a polypeptide of interest. In order for the polypeptide of interest to be expressed, a promoter is also required. Thus, in one example, each of the at least one polynucleotide encoding for a polypeptide of interest is operatively linked to a promoter. In one example, the promoter is at the 5' direction of each of the at least one polynucleotide encoding for a polypeptide of interest. A person skilled in the art is aware that more than one promoter may be needed for the expression of more than one polypeptide. Thus, in one example and as shown for example in FIG. 6A, in the expression vector described herein, the promoter linked to the polynucleotide encoding for a glutamine synthetase with reduced activity is different from the promoter linked to the at least one polynucleotide encoding for a polypeptide of interest.

Figure 6B:
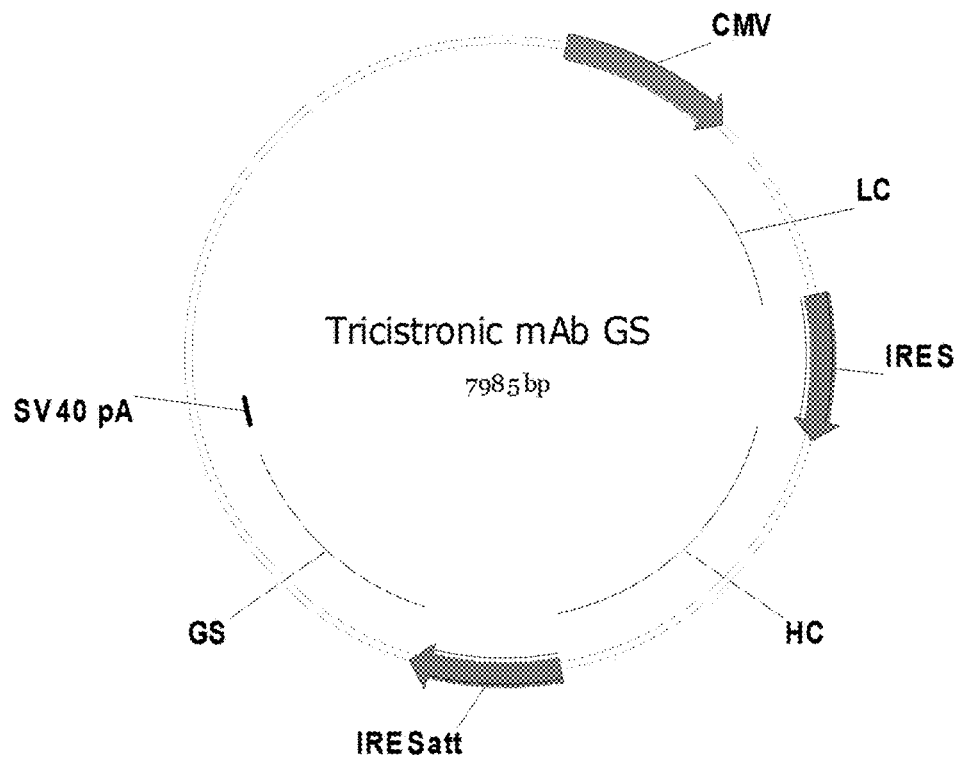
FIG. 6B depicts the expression vector map of tricistronic mAb GS. The full length sequence that corresponds to tricistronic mAb GS is listed as SEQ ID NO: 14. Sequences that correspond to specific regions of the expression vector map of tricistronic mAb GS are listed as SEQ ID NOs: 15 to 30.
Figure 6C:
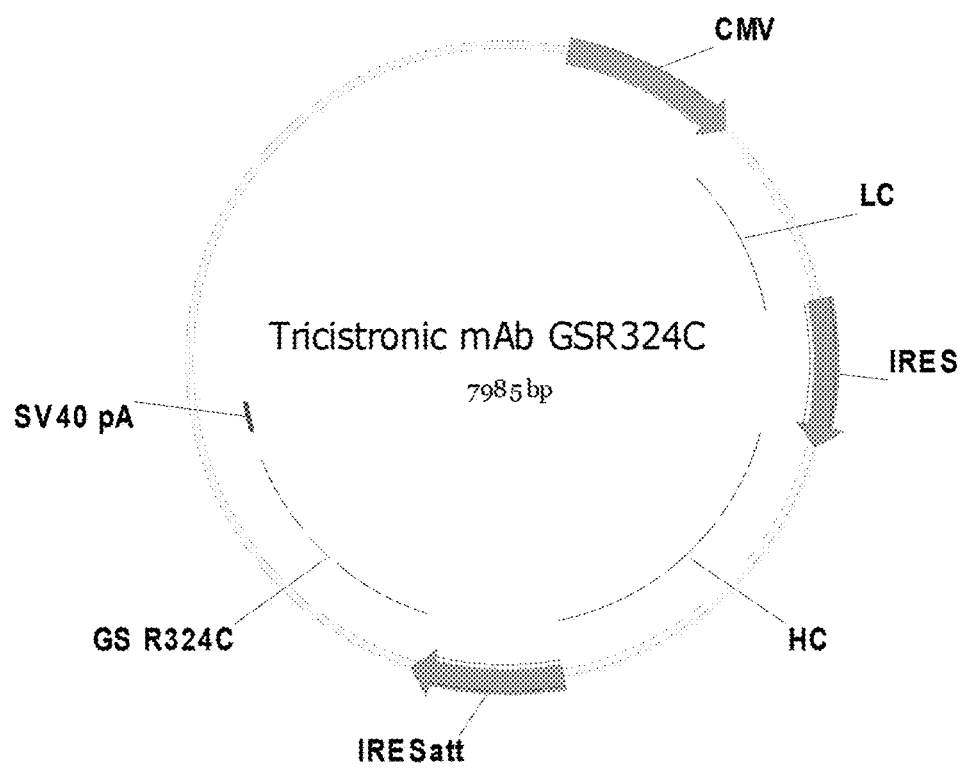
FIG. 6C depicts the expression vector map of tricistronic mAb GS R324C, an exemplary expression vector that express attenuated glutamine synthetase. The full length sequence that corresponds to tricistronic mAb GS R324C is listed as SEQ ID NO: 85. Sequences that correspond to specific regions of the expression vector map of tricistronic mAb GS R324C are listed as SEQ ID NOs: 86 to 101. Thus.

Further to the above and as shown for example on FIGS. 6B and 6C, in the expression vector described herein, only one of the at least one polynucleotide encoding for a polypeptide of interest is operatively linked to a promoter. In one example, the promoter is at the 5' direction of the one polynucleotide encoding for a polypeptide of interest that is operatively linked to a promoter. In one example, the polynucleotide encoding for a glutamine synthetase with reduced activity compared to a wild type glutamine synthetase is not linked to a promoter.

As discussed above, stable cell lines generated using the expression vector described herein can be used to express polypeptide of interest. Thus, in one example, the expression vector described herein further comprising at least one polynucleotide encoding for a polypeptide of interest such as a recombinant gene product. As used herein, the term "polypeptide of interest" refers to a polypeptide that are not native to the host cell and that can be expressed at a suitable amount in a host cell using the expression vector described herein. Thus, non-limiting example of the polypeptide of interest that is encoded by the expression vector includes but is not limited to a recombinant protein and a part thereof, a fusion protein and a part thereof, an antibody and a part thereof, and the like. Any type of antibody that is made of polypeptide can be expressed using the expression vector described herein. In one example, the antibody is a monoclonal antibody. In one example, the monoclonal antibody that is encoded by the expression vector is antibody GA101 (also referred as "Antibody A" in the present disclosure). In one example, the monoclonal antibody that is encoded by the expression vector is Rituximab (also referred as "Antibody B" in the present disclosure). A person skilled in the art is aware that an antibody typically comprises light chains and heavy chains. As used herein, the term "light chains" refer to the shorter or smaller polypeptide subunit of an antibody or an immunoglobulin whereas the term "heavy chains" refer to the longer or larger polypeptide subunit of an antibody or an immunoglobulin. Thus, in one example, the polypeptide of interest that is encoded by the expression vector described herein is the heavy chain of an antibody of interest. In one example, the polypeptide of interest that is encoded by the expression vector described herein is the light chain of an antibody of interest. The heavy chain and the light chain of the antibody of interest as described herein can both be expressed by one expression vector. Thus, in one example, the expression vector as described herein comprises two polynucleotides each encoding for a polypeptide of interest, wherein one of the polynucleotides encodes for the light chain of an antibody of interest and one of the polynucleotides encodes for the heavy chain of the same antibody of interest.

As shown for example in FIG. 6, in the expression vector as described herein, the polynucleotide encoding for the light chain of an antibody of interest and the polynucleotide encoding for the heavy chain of the same antibody of interest are separated by an internal ribosome entry site. As used herein, the term "internal ribosome entry site" or "IRES" refers to polynucleotide sequences in an expression vector (such as a multicistronic, bicistronic, or tricistronic expression vector), which when transcribed into mRNA, are believed to recruit ribosomes directly, without a previous scanning of untranslated region of mRNA by the ribosomes. IRESs are commonly used to direct the expression of the second cistrons of bicistronic mRNAs. As used herein, the term "multicistronic expression vector" refers to an expression vector that comprises of multiple cistrons multiple sections that encodes for multiple polypeptides. Thus, a multicistronic expression vector can be transcribed into an mRNA that can simultaneously expresses two or more separate polypeptides. Therefore, a bicistronic expression vector is an expression vector comprising two cistrons and an mRNA transcribed from a bicistronic expression vector can simultaneously express two separate polypeptides. A tricistronic expression vector is an expression vector comprising three cistrons and an mRNA transcribed from a tricistronic expression vector can simultaneously express three separate polypeptides.

The inventors have found that the ability of the expression vector described herein to express the light chain and the heavy chain of an antibody of interest is not negatively affected by the position of the polynucleotides encoding for the light chain and for the heavy chain of an antibody of interest. Having said that, it is generally understood that the expression level of the polynucleotides in an IRES containing vector is affected by the position of the polynucleotides with respect to the IRES. The first polypeptide (i.e. the polypeptide that is encoded by polynucleotide located before the IRES) will have a higher expression level than the second polypeptide that is encoded by the polynucleotide located after the IRES. Thus, in one example, in the expression vector as described herein, the polynucleotide encoding for the light chain of an antibody of interest is in the 5' direction of the polynucleotide encoding for the heavy chain of the same antibody of interest. In another example, in the expression vector as described herein, the polynucleotide encoding for the heavy chain of an antibody of interest is in the 5' direction of the polynucleotide encoding for the light chain of the same antibody of interest.

As also shown for example in FIG. 6, the polynucleotide encoding the antibody of interest is located upstream or is in the 5' direction of the polynucleotide encoding for a glutamine synthetase with reduced activity. Those polynucleotides are separated by an internal ribosome entry site (IRES). Thus, in one example, in the expression vector as described herein, the polynucleotide encoding for the heavy chain of an antibody of interest is separated from the polynucleotide encoding for a glutamine synthetase with reduced activity by an internal ribosome entry site. In another example, in the expression vector as described herein, the polynucleotide encoding for the light chain of an antibody of interest is separated from the polynucleotide encoding for a glutamine synthetase with reduced activity by an internal ribosome entry site. As used herein, the term "separated from" means that the locations of polynucleotides encoding for a polypeptide that are not located right next to another polynucleotides encoding for another polypeptides. In between those two polynucleotides that encode two different polypeptides, there are polynucleotides encoding other sequences (such as encoding internal ribosome entry site or IRES).

Further to the above, as also shown for example in FIGS. 6B and 6C, an expression vector as described herein may comprise more than one internal ribosome entry sites (IRES). Thus, in one example, the internal ribosome entry site separating the polynucleotide encoding for the light chain of an antibody of interest and the polynucleotide encoding for the heavy chain of the same antibody of interest is different from the internal ribosome entry site separating the polynucleotide encoding for the light/heavy chain of an antibody of interest from the polynucleotide encoding for a glutamine synthetase with reduced activity. When an expression vector as described herein comprises more than one internal ribosome entry sites (IRES), the internal ribosome entry sites can be of multiple types and can have different translation efficiencies. Thus, in one example, in the expression vector described herein, the internal ribosome entry site separating the polynucleotide encoding for the light chain of an antibody of interest and the polynucleotide encoding for the heavy chain of the same antibody of interest is a wild type internal ribosome entry site, and wherein the internal ribosome entry site separating the polynucleotide encoding for the light/heavy chain of an antibody of interest from the polynucleotide encoding for a glutamine synthetase with reduced activity is an internal ribosome entry site with attenuated translation efficiency. As shown for example in FIGS. 6B and 6C, the wild type internal ribosome entry site is denoted as "IRES" and the internal ribosome entry site with attenuated translation efficiency is denoted as "IRESatt". As used herein, the term "internal ribosome entry site with attenuated translation efficiency" or "IRESatt" refers to an IRES wherein its 3' region has been modified such that its translation efficiency is reduced when compared to a wild type IRES.

Further to the above, a person skilled in the art is aware that the 3' ends of most mammalian mRNAs are polyadenylated or are connected with multiple adenine that forms poly(A) tail. Poly(A) tail is essential for the survival, transport, stability, and translation of most mRNAs. In order to provide for the poly(A) tail, the expression vector has to comprise one or more polyadenylation signals. When more than one polyadenylation signals are provided, the polyadenylation signal can be located at the 3' end of each set of polynucleotide sequences that encode for a polypeptide. Thus, in one example, the expression vector as described herein comprises one polyadenylation signal at the 3' end of each of the at least one polynucleotide encoding for a polypeptide of interest, and one polyadenylation signal at the 3' end of the polynucleotide encoding for a glutamine synthetase with reduced activity. As shown for example on FIG. 6A, the expression vector comprises two polyadenylation signals, wherein one signal is located at the 3' end of the polynucleotide encoding the heavy chain of an antibody of interest and wherein the other signal is located at the 3' end of the polynucleotide encoding for a glutamine synthetase with reduced activity. In another example, the expression vector as described herein comprises one polyadenylation signal only at the 3' end of the polynucleotide encoding for a glutamine synthetase with reduced activity. As shown for example on FIGS. 6B and 6C, the expression vector comprises of only one polyadenylation signal, which is located at the 3' end of the polynucleotide encoding for a glutamine synthetase with reduced activity.

As discussed above, to generate stable cell lines using glutamine synthetase with reduced activity as a selection marker, the expression vector as described herein is inserted or incorporated into a host cell. Thus, in one aspect, the present invention provides a host cell comprising the expression vector as described herein. Prior to the insertion or the incorporation of the expression vector described herein, the host cell does not have any glutamine synthetase activity or the host cell has minimum amount of glutamine synthetase activity. As used herein, the term "minimum amount of glutamine synthetase activity" refers to an amount of glutamine synthetase activity that does not allow the host cells to grow and/or survive in the absence of L-glutamine supplementation. After the insertion or the incorporation of the expression vector described herein into the host cell, glutamine synthetase having reduced activity is produced. Therefore, the host cell comprising the expression vector described herein will have glutamine synthetase activity but the glutamine synthetase activity of said host cells will be lower than the glutamine synthetase activity of a wild type cell.

A person skilled in the art appreciated that any type of host cell that does not have glutamine synthetase activity prior to the insertion or incorporation of the expression vector described herein can be used. In one example, the host cells can be prepared from any cells (such as mammalians or yeast cells) that typically have genes that encode for wild type or mutant or attenuated glutamine synthetase and wherein said gene has been knocked out. As used herein, the term "knocked out" refers to genes that have been inactivated and hence cannot express protein of interest. Cells wherein the glutamine synthetase encoding genes have been knocked out lose their glutamine synthetase activity and cannot survive in glutamine-free environment without insertion or incorporation of the expression vector described herein. Therefore, said cells are suitable as host cells for the present disclosure. In one example, the host cell comprising the expression vector described herein is a mammalian cell. Non limiting example of mammalian cell that can be used as a host cell of the expression vector described herein includes, but is not limited to, Chinese hamster ovary (CHO) cell line, human embryonic kidney 293 (HEK293) cell line, cell lines derived from mouse, cell lines derived from rat, cell lines derived from human, and the like. In one example, the host cell comprising the expression vector described herein is a Chinese hamster ovary (CHO) cell line. In one example, the host cell comprising the expression vector described herein is a CHOK1 GFT$^{-/-}$ GS$^{-/-}$ cell line or a CHOK1 GS$^{-/-}$. As used herein the term "GFT" stands for GDP fucose transporter. As used herein, the symbol "-/-" refers to the fact that the cell is deficient of certain enzyme. For example, GFT$^{-/-}$ denotes that the cell is deficient of GDP fucose transporter (GFT) and GS$^{-/-}$ denotes that the cell is deficient of glutamine synthetase (GS). In one example, the host cell comprising the expression vector described herein is a yeast cell. Non limiting example of yeast cell that can be used as a host cell of the expression vector described herein includes, but is not limited to, cell lines derived from *Saccharomyces cerevisiae*, and the like.

Figure 9:
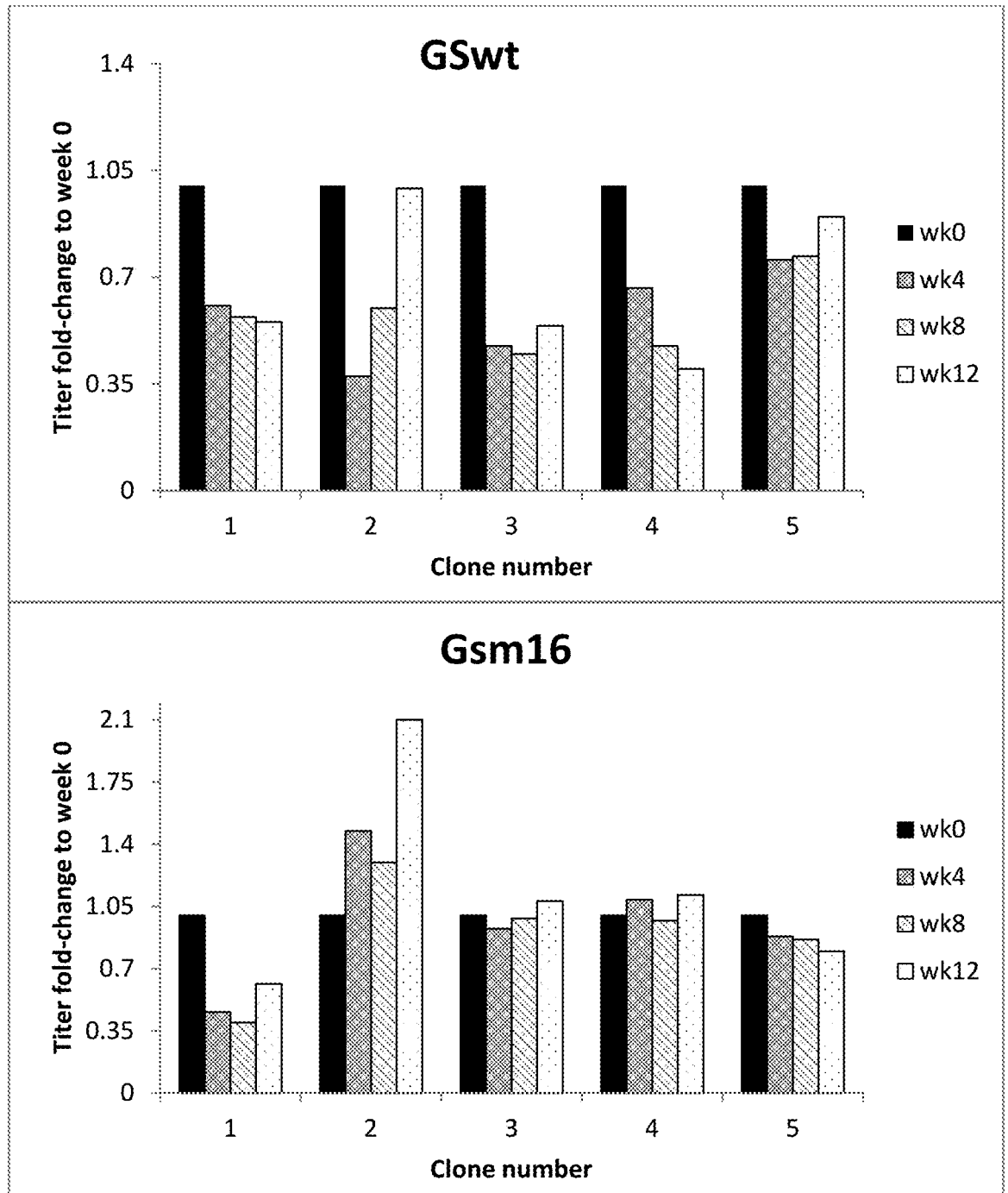
FIG. 9 shows a pair of bar graphs depicting the stability assessment of five random clones from stable generated using GSwt as the selection marker (as shown on FIG. 9A) or GSm16 (i.e. GS having S257A mutation site) as the selection marker (as shown on FIG. 9B). Thus.
Figure 10:
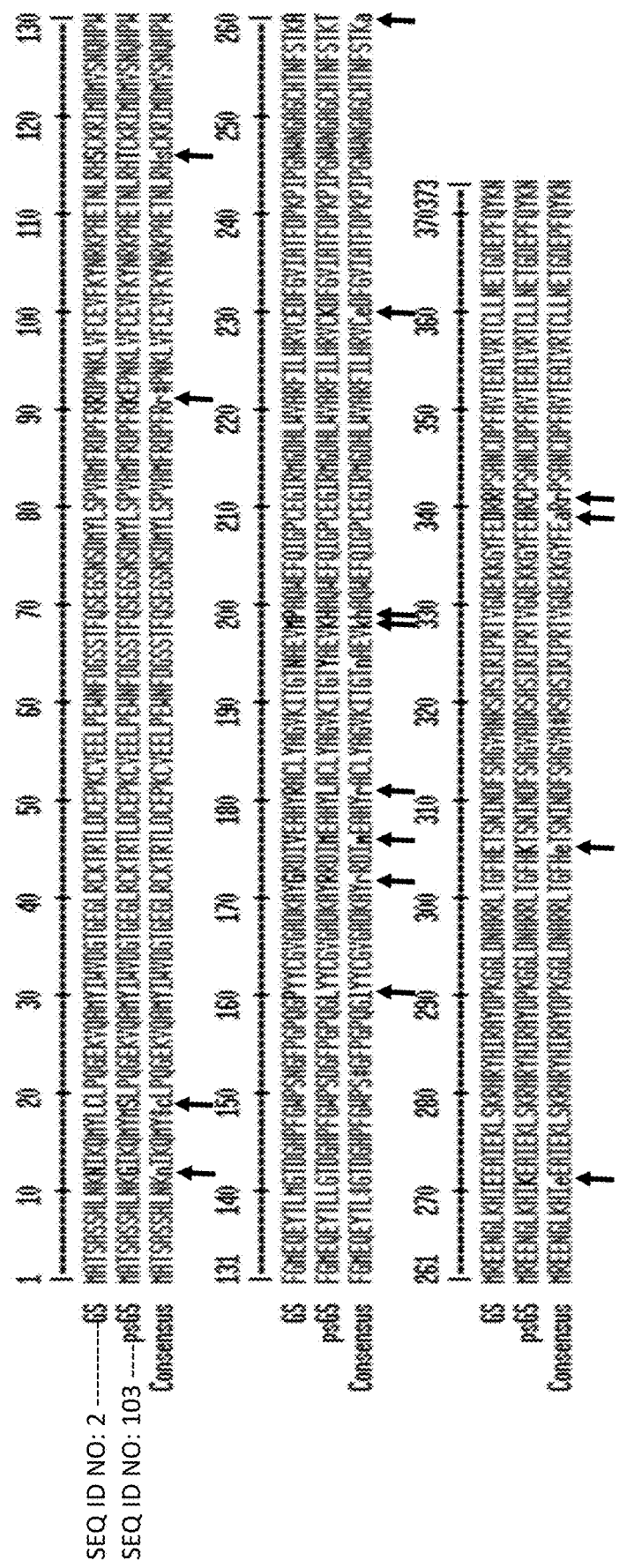
FIG. 10 shows a sequence alignment comparing wild type GS protein sequences from CHO cells (labeled as "GS"; SEQ ID NO: 2) and pseudoGS protein sequences from CHO cells (labeled as "psGS"; SEQ ID NO: 103). PseudoGS (psGS) is a stretch of genomic DNA which seems to also code for the GS protein. This psGS genomic locus, unlike the wild type GS gene, does not contain any intervening intron sequences. PseudoGS protein is typically not expressed. PseudoGS comprises several mutations throughout the protein as shown (using black arrows) in the alignment. Importantly, psGS protein comprises 2 mutation sites that are identified to have attenuating effects on GS activity. The sites are E305 site (E305K) and site R341 (R341C), of which the latter is the congenital diseased patient site. This psGS gene was cloned from CHO-K1 cells and its GS activity was tested. It was found that the psGS protein has minimal activity compared to WT GS as shown in the bar graph on FIG. 4. Thus.

In addition to providing an alternative expression vector and a host cell comprising said expression vector, as shown for example in FIG. 9, the inventors of the present invention have also provided an alternative method for preparing stable cell line. Thus, in yet another aspect, the present invention provides a method for preparing stable cell line, comprising: (a) transforming a host cell having minimum amount of glutamine synthetase activity or no glutamine synthetase activity with the expression vector described herein; (b) culturing the transformed host cell in a medium that selectively allows the proliferation of the transformed host cells comprising an amplified number of copies of the vector to be selected. In yet another aspect, the present invention provides a method for preparing stable cell line, comprising: (a) transforming a host cell having no glutamine synthetase activity with the expression vector described herein; (b) culturing the transformed host cell in a medium that selectively allows the proliferation of the transformed host cells comprising an amplified number of copies of the vector to be selected. As used herein, the term "stable cell line" refers to cells comprising expression vector described herein that are able to sustainably express a polypeptide of interest.

Further to the above, as shown for example in FIG. 2, the inventors of the present invention have also provided an alternative method for producing antibody polypeptide of interest. Thus, in yet another aspect, the present invention provides a method of producing polypeptide of interest, comprising: (a) transforming a host cell having minimum amount of glutamine synthetase activity or no glutamine synthetase activity with the expression vector described herein; (b) culturing the transformed host cell in a medium that selectively allows the production of polypeptide of interest; and (c) collecting the polypeptide of interest from the medium of (b). In yet another aspect, the present invention provides a method of producing polypeptide of interest, comprising: (a) transforming a host cell having no glutamine synthetase activity with the expression vector described herein; (b) culturing the transformed host cell in a medium that selectively allows the production of polypeptide of interest; and (c) collecting the polypeptide of interest from the medium of (b). Collection of the polypeptide of interest from the cell culture medium can be performed using any method known in the art. Non limiting examples of method to collect the polypeptide of interest from the medium include, but are not limited to, size exclusion chromatography, hydrophobic interaction chromatography, ion exchange chromatography, free-flow-electrophoresis, affinity chromatography, immunoaffinity chromatography, high performance liquid chromatography, and the like.

As used herein, the term "transformation" refers to the genetic alternation of a cell resulting from the direct uptake and incorporation of exogenous genetic materials from its surrounding. The term "transforming a host cell" thus refers to the act of introducing or contacting exogenous genetic material such as the expression vector described herein to the host cell. The term "transformed host cell" thus refers to a host cell into which an exogenous genetic material such as the expression vector described herein has been inserted or incorporated. Transformation of a host cells with the expression vector described herein can be performed using any method known in the art. In one example of the method described herein, the medium that allow the transformed host cells comprising an amplified number of copies of the vector to be selected is a glutamine free cell culture medium. In one example of the method described herein, the transformed host cells are cultured under glutamine free conditions. Without wishing to be bound by theory, when the host cells are cultured under glutamine free conditions, host cells that are not inserted by the expression vector described herein or the host cells that do not incorporate the expression vector described herein will not be able to survive and/or proliferate under the glutamine free condition. The inventors have also surprisingly found that when the attenuated GS (GSatt) or a glutamine synthetase with reduced activity compared to a wild type glutamine synthetase is used as the selection marker for producing antibody polypeptide of interest in stably transfected cells, only the cells with the expression vector inserted into highly transcriptionally active site or the cells having several copies of the expression vectors inserted into less active site to compensate for the loss of GS activity can survive the selection. Therefore, unlike when wild type GS is used as a selection marker, the selection of cells using GS inhibitor (i.e. selection for cells having higher copy number of wild type GS) may not be required. Thus, in one example, the method described herein does not comprise the use of a glutamine synthetase inhibitor. The glutamine synthetase inhibitor that is not used in the method described herein can include any glutamine synthetase inhibitor known in the art. In one example, the glutamine synthetase inhibitor that is not used in the method described herein is methionine sulphoximine (MSX).

Figure 3:
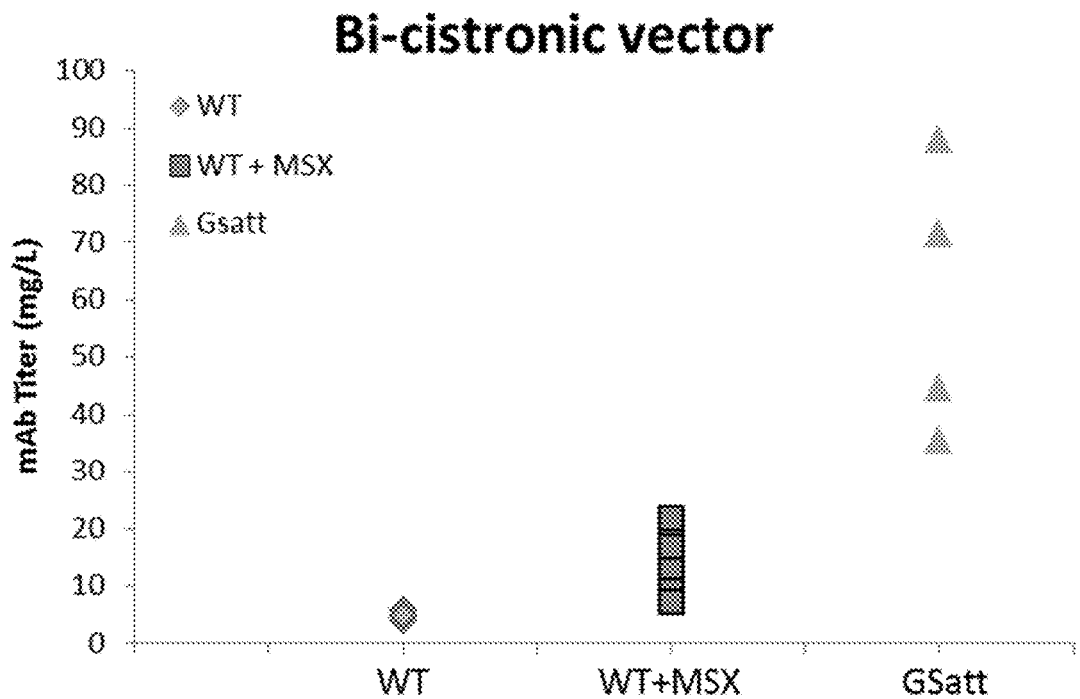
FIG. 3 shows a scatter plot depicting the amount of antibodies titer (mAb titer) produced by stable pools using (a) bicistronic expression vector having wild type GS (WT) as a selection marker (data points are shown in diamonds), or (b) bicistronic expression vector having wild type GS (WT) as a selection marker and wherein the cells are also treated with 25 μM of methionine sulphoximine (MSX) (data points are shown in squares), or (c) bicistronic expression vector having attenuated GS (GSatt) as a selection marker (cells are not treated with MSX; data points are shown in triangles). Thus.

The inventors have surprisingly found that the use of attenuated GS as a selection marker provides an advantage over the use of wild type GS (WT GS) as a selection marker. As shown for example in FIG. 3, the amount of mAb titer in the batch culture stable pools transfected with the mutant GS are generally higher than those WT GS pools treated with MSX (25 µM). The average fold-enhancement is about 9-fold. This is higher than the 2 fold-enhancement between WT GS and WT GS plus MSX that is observed in the prior art.

More importantly, the use of attenuated GS as a selection marker improves production stability. Attenuation of other selection markers like neomycin phosphotransferase II and Dihydrofolate reductase (DHFR) genes through mutation have been previously developed for enhancing the production titer. However, attenuation of those other selection markers still require the use of drug to enhance the productivity. The use of drug induces a problem in the stable cell line generation process where stability testing upon drug removal is required. Stability in production is often tested by isolating hundreds of clones and measuring their production over 60 generations (2 to 3 months). This is a laborious and time consuming process. On the other hand, the use of expression vector described herein (i.e. an expression vector comprising polynucleotide encoding attenuated mutant GS) mimics the inhibition of GS activity via GS inhibitor such as MSX drug. As the mutant GS constantly acts as a selection pressure, the production stability would be enhanced. Hence, the mutant GS creates an advantage in the stability testing.

In yet another aspect, the present invention provides a kit comprising the expression vector described herein. In one example, the kit comprising the expression vector described herein further comprises at least one of the following: (i) a host cell having no glutamine synthetase activity compared to a wild type cell; and (ii) a transfection medium or means to carry out a transfection. In one example, the kit as described herein further comprises a cell culture medium. In one example, the cell culture medium does not contain glutamine. In one example, the kit as described herein further comprises a glutamine free cell culture medium.

As used in this application, the singular form "a," "an," and "the" include plural references unless the context clearly dictates otherwise. For example, the term "an expression vector" includes a plurality of expression vectors, including mixtures and combinations thereof.

As used herein, the terms "increase" and "decrease" refer to the relative alteration of a chosen trait or characteristic in a subset of a population in comparison to the same trait or characteristic as present in the whole population. An increase thus indicates a change on a positive scale, whereas a decrease indicates a change on a negative scale. The term "change", as used herein, also refers to the difference between a chosen trait or characteristic of an isolated population subset in comparison to the same trait or characteristic in the population as a whole. However, this term is without valuation of the difference seen.

As used herein, the term "about" in the context of certain stated values means +/−5% of the stated value, or +/−4% of the stated value, or +/−3% of the stated value, or +/−2% of the stated value, or +/−1% of the stated value, or +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Material and Methods
Generation of Tricistronic mAb GS Vector.

The GS gene was amplified from the CHO cells cDNA library. The DHFR gene of the tricistronic DHFR vector was replaced with the GS gene via standard cloning methods. The primers used were:

```
GSsmaUP (SEQ ID NO: 31):
GTGTGACCCGGGAGATGAGGATCGTTTCGCATGGCCACCTCAGCAAGTTC
CCACTTG;
and GSBstBILP (SEQ ID NO: 32):
GAATTCTTCGAATTAGTTTTTGTATTCGAAGGGCTCGTCGCC.
```

The mAb heavy and light chains were synthesized commercially and subsequently cloned into the region after the CMV promoter of the tricistronic GS vector in the following orientation: Light chain-IRES-heavy chain-IRESatt GS.
Generation of Bicistronic mAb GS Vector.

pcDNA3.1 (+) from Invitrogen was used as the vector backbone. The full length heavy and light chains were cloned into the MCS of the vector as a bicistronic construct: light chain-IRES-heavy chain. The neomycin gene after the SV40 promoter was replaced with the WT GS construct. The primers used for amplifying the GS gene from the tricistronic mAb GS vector were:

```
GSSMASV4UP (SEQ ID NO: 33):
GTGCTCCCGGGAGCTTGTATATCCATTTTCGGATCTGATCAAGAGACAGG
ATGAGGATCGGCCACCATGGCCACCTCAGCAAGTTCCCACTTGAAC;
and GSBSTBISV4LP (SEQ ID NO: 34):
GGTCATTTCGAACCCCAGAGTCCCGCTTAGTTTTTGTATTGGAAGGGCTC
GTCG
```

Generation of the GS-IRES-Luciferase Construct (GS-Luc).

The GS gene was cloned into the MCS region of the pcDNA3.1 (+) vector. The RES construct was cloned in after the GS gene and followed by the firefly luciferase gene. This expression cassette of GS-IRESLuciferase was used to evaluate the GS activity in which the luciferase activity was used to normalize the GS expression level.
Generation of the pseudoGS Construct The coding sequence of the pseudo Glutamine Synthetase gene (psGS gene) was amplified from the genomic DNA of CHO-K1 cells. The psGS gene was then cloned into the GS-Luc construct (as discussed above) to replace the original GS gene to form the expression cassette of psGS-IRESLuciferase. The GS activity assay of this construct was performed as described below.
GS Activity Assay.

Adherent CHO-K1 GS$^{-/-}$ cells were cultured in DMEM with 10% FBS in 37° C., 5% $CO_2$ incubator. The cells were transfected with the various GS/GSm-Luc constructs via LTX transfection reagent (Invitrogen). The cells were harvested 24 hrs post-transfection with the Reporter Lysis buffer (Promega) and their luciferase activity was measured according to the protocol of the Luciferase Assay kit (Promega). The GS activity was measured using the standard GS activity assay whereby GS-catalyzed formation of γ-glutamylhydroxamate from glutamine and hydroxylamine was measured at 500 nm. Briefly, the cell lysate supernatant was incubated with shaking at 37° C. for 45 mins with 100 mM Imidazole-HCl (pH 7), 50 mM L-Glutamine, 0.4 mM $MnCl_2$, 62.5 mM Hydroxylamine (pH 7) and 10 mM sodium arsenate to a final volume 250 μl. The reaction was terminated by the addition of 250 μl $FeCl_3$ reagent (0.37M $FeCl_3$, 0.67M HCl, 0.2M TCA). Precipitate was removed by centrifugation at 10,000 rpm for 5 mins and the absorbance of supernatant was measured at 500 nm using a spectrophotometer. The activity of the GS was normalized over that of the luciferase level.
Mutagenesis of the GS Gene.

Mutageneses of the specific sites were achieved by designing primers with the specific mutations. The sites targeted (as shown on Table 1 below) were conserved between human and Chinese hamster GS. QuikChange site directed mutagenesis reaction of the Tricistronic mAb GS/bicistronic mAb GS/or the GSLuc vectors were performed using the primers listed in Table 2 below. Sequencing was performed to ensure that the mutations were achieved.

TABLE 1

Legend of the GS Mutation Sites

| Name | Mutation | Amino Acid at said position typically involved in |
|---|---|---|
| R324C | Identified as congenital GS mutation | ATP binding |
| R341C | Identified as congenital GS mutation | N/A |

TABLE 1-continued

Legend of the GS Mutation Sites

| Name | Mutation | Amino Acid at said position typically involved in |
|---|---|---|
| 1 | D63A | Ammonia binding |
| 2 | S66A | Ammonia binding |
| 4 | E134A | Glutamate binding |
| 5 | E136A | Glutamate binding |
| 6 | Y162A | Ammonia binding |
| 8 | G192A | ATP binding |
| 9 | E196A | Glutamate binding |
| 10 | E203A | Glutamate binding |
| 12 | N248A | Glutamate binding |
| 13 | G249A | Glutamate binding |
| 14 | H253A | Glutamate binding |
| 15 | N255A | ATP binding |
| 16 | S257A | ATP binding |
| 17 | R262A | ATP binding |
| 18 | R299A | Glutamate binding |
| 19 | E305A | Ammonia binding |
| 20 | R319A | Glutamate binding |
| 21 | Y336A | ATP binding |
| 22 | E338A | Glutamate binding |
| 23 | K333A | ATP binding |
| 24 | R340A | Glutamate binding |

TABLE 2

List of primers for GS mutation

| SEQ ID NO | Name | Sequence |
|---|---|---|
| SEQ ID NO: 35 | R324C FP | CGCAGTGCCAGCATCTGCATTCCCCGGACTGTCGGC |
| SEQ ID NO: 36 | R324C LP | GCCGACAGTCCGGGGAATGCAGATGCTGGCACTGCG |
| SEQ ID NO: 37 | R341C FP | GGTTACTTTGAAGACCGCTGCCCCTCTGCCAATTGTGAC |
| SEQ ID NO: 38 | R341C LP | GTCACAATTGGCAGAGGGGCAGCGGTCTTCAAAGTAACC |
| SEQ ID NO: 39 | R324A UP | CGCAGTGCCAGCATCGCCATTCCCCGGACTGTC |
| SEQ ID NO: 40 | R324A LP | GACAGTCCGGGGAATGGCGATGCTGGCACTGCG |
| SEQ ID NO: 41 | R341A UP | TACTTTGAAGACCGCGCCCCCTCTGCCAATTGT |
| SEQ ID NO: 42 | R341A LP | ACAATTGGCAGAGGGGGCGCGGTCTTCAAAGTA |
| SEQ ID NO: 43 | GSM1 UP | CCTGAGTGGAATTTTGCTGGCTCTAGTACCTTTCAG |
| SEQ ID NO: 44 | GSM1 LP | CTGAAAGGTACTAGTGCCAGCAAAATTCCACTCAGG |
| SEQ ID NO: 45 | GSM2 UP | TGGAATTTTGATGGCTCTGCTACCTTTCAGTCTGAGGGC |
| SEQ ID NO: 46 | GSM2 LP | GCCCTCAGACTGAAAGGTAGCAGAGCCATCAAAATTCCA |
| SEQ ID NO: 47 | GSM4 UP | CACCCCTGGTTTGGAATGGCACAGGAGTATACTCTG |
| SEQ ID NO: 48 | GSM4 LP | CAGAGTATACTCCTGTGCCATTCCAAACCAGGGGTG |
| SEQ ID NO: 49 | GSM5 UP | TGGTTTGGAATGGAACAGGCGTATACTCTGATGGGAACA |
| SEQ ID NO: 50 | GSM5 LP | TGTTCCCATCAGAGTATACGCCTGTTCCATTCCAAACCA |
| SEQ ID NO: 51 | GSM6 UP | CCCCAAGGTCCGTATGCCTGTGGTGTGGGCGCAGAC |
| SEQ ID NO: 52 | GSM6 LP | GTCTGCGCCCACACCACAGGCATACGGACCTTGGGG |

TABLE 2-continued

List of primers for GS mutation

| SEQ ID NO | Name | Sequence |
|---|---|---|
| SEQ ID NO: 53 | GSM8 UP | GGGGTCAAGATTACAGCAACAAATGCTGAGGTC |
| SEQ ID NO: 54 | GSM8 LP | GACCTCAGCATTTGTTGCTGTAATCTTGACCCC |
| SEQ ID NO: 55 | GSM9 UP | ACAGGAACAAATGCTGCGGTCATGCCTGCCCAG |
| SEQ ID NO: 56 | GSM9 LP | CTGGGCAGGCATGACCGCAGCATTTGTTCCTGT |
| SEQ ID NO: 57 | GSM10 UP | ATGCCTGCCCAGTGGGCATTCCAAATAGGACCC |
| SEQ ID NO: 58 | GSM10 LP | GGGTCCTATTTGGAATGCCCACTGGGCAGGCAT |
| SEQ ID NO: 59 | GSM12 UP | ATTCCTGGGAACTGGGCAGGTGCAGGCTGCCATACC |
| SEQ ID NO: 60 | GSM12 LP | GGTATGGCAGCCTGCACCTGCCCAGTTCCCAGGAAT |
| SEQ ID NO: 61 | GSM13 UP | CCTGGGAACTGGAATGCTGCAGGCTGCCATACC |
| SEQ ID NO: 62 | GSM13 LP | GGTATGGCAGCCTGCAGCATTCCAGTTCCCAGG |
| SEQ ID NO: 63 | GSM14 UP | AATGGTGCAGGCTGCGCAACCAACTTTAGCACC |
| SEQ ID NO: 64 | GSM14 LP | GGTGCTAAAGTTGGTTGCGCAGCCTGCACCATT |
| SEQ ID NO: 65 | GSM15 UP | GCAGGCTGCCATACCGCATTTAGCACCAAGGCC |
| SEQ ID NO: 66 | GSM15 LP | GGCCTTGGTGCTAAATGCGGTATGGCAGCCTGC |
| SEQ ID NO: 67 | GSM16 UP | GGCTGCCATACCAACTTTGCAACCAAGGCCATGCGG |
| SEQ ID NO: 68 | GSM16 LP | CCGCATGGCCTTGGTTGCAAAGTTGGTATGGCAGCC |
| SEQ ID NO: 69 | GSM17 UP | AGCACCAAGGCCATGGCGGAGGAGAATGGTCTG |
| SEQ ID NO: 70 | GSM17 LP | CAGACCATTCTCCTCCGCCATGGCCTTGGTGCT |
| SEQ ID NO: 71 | GSM18 UP | CTGGACAATGCCCGTGCTCTGACTGGGTTCCAC |
| SEQ ID NO: 72 | GSM18 LP | GTGGAACCCAGTCAGAGCACGGGCATTGTCCAG |
| SEQ ID NO: 73 | GSM19 UP | CTGACTGGGTTCCACGCAACGTCCAACATCAAC |
| SEQ ID NO: 74 | GSM19 LP | GTTGATGTTGGACGTTGCGTGGAACCCAGTCAG |
| SEQ ID NO: 75 | GSM20 UP | GCTGGTGTCGCCAATGCCAGTGCCAGCATCCGC |
| SEQ ID NO: 76 | GSM20 LP | GCGGATGCTGGCACTGGCATTGGCGACACCAGC |

TABLE 2-continued

List of primers for GS mutation

| SEQ ID NO | Name | Sequence |
|---|---|---|
| SEQ ID NO: 77 | GSM21 UP | CAGGAGAAGAAAGGTGCTTTTGAAGACCGCCGC |
| SEQ ID NO: 78 | GSM21 LP | GCGGCGGTCTTCAAAAGCACCTTTCTTCTCCTG |
| SEQ ID NO: 79 | GSM22 UP | AAGAAAGGTTACTTTGCAGACCGCCGCCCCTCTGCC |
| SEQ ID NO: 80 | GSM22 LP | GGCAGAGGGGCGGCGGTCTGCAAAGTAACCTTTCTT |
| SEQ ID NO: 81 | GSM23 UP | ACTGTCGGCCAGGAGGCGAAAGGTTACTTTGAA |
| SEQ ID NO: 82 | GSM23 LP | TTCAAAGTAACCTTTCGCCTCCTGGCCGACAGT |
| SEQ ID NO: 83 | GSM24 UP | GGTTACTTTGAAGACGCCCGCCCCTCTGCCAAT |
| SEQ ID NO: 84 | GSM24 LP | ATTGGCAGAGGGGCGGGCGTCTTCAAAGTAACC |

Notes:
Primers designated as "R324C" and "R341C" introduce point mutation wherein Arginine (R) is mutated to Cysteine (C) at amino acid position 324 and position 341.
Primers designated as "R324A" and "R341A" introduce point mutation wherein Arginine (R) is mutated to Alanine (A) at amino acid position 324 and position 341.
Primers designated as "GSM##" introduce point mutation wherein the amino acid residue is mutated to Alanine (A). The number on "GSM##" corresponds to the column titled "Name" in Table 1. For example, primer designated as GSM1 corresponds to a primer that introduces D63A mutation (i.e. point mutation wherein Aspartic acid (D) at amino acid position 63 is mutated to Alanine (A)) and so on.
Primers that are designated as "UP" or "FP" are forward primer. Primers that are designated as "LP" are reverse primer Cell Culture, Transfection and Stable Pool Generation.

Suspension CHO-K1 GS$^{-/-}$ cells were cultured in HyClone PF CHO mixed with CD CHO media in 1:1 ratio (50/50) and incubated in 37° C., 8% CO$_2$ shaking incubator. The 50/50 media was supplemented with 0.05% Pluronic F-68 acid and 6 mM L-Glutamine. Cells were transfected with the Tricistronic/Bicistronic mAb GS/GSm constructs via Electroporation (LONZA SG kit) in the following conditions: 10 million cells with 5 ug of DNA. Two days post transfection, the transfected cells were placed under the L-glutamine free selection till their viability recovered to more than 90%. Batch culture was then performed on the recovered pools to measure the level of IgG production. IgG level was measured using the Nephelometer with the IgGC assay reagent.

Experimental Result

Transfection of CHO-K1 GFT$^{-/-}$ GS$^{-/-}$ with Either Tricistronic mAb-GS or Tricistronic mAb-GSatt (R324C)-Minipools Format.

Mutation of the GS gene at site -R324 to C (GSatt), corresponding to the glutamate binding region of the enzyme was made. The vector encoding an antibody gene and the GSatt selection marker in the tricistronic vector (Ho S C et. al., 2012) was compared with the wild type GS in the same format. The comparison in stable productivity level was done in CHO-K1-GF$^{-/-}$ GS$^{-/-}$ cells. The stable productions of 2 different antibodies were tested.

Figure 1B:
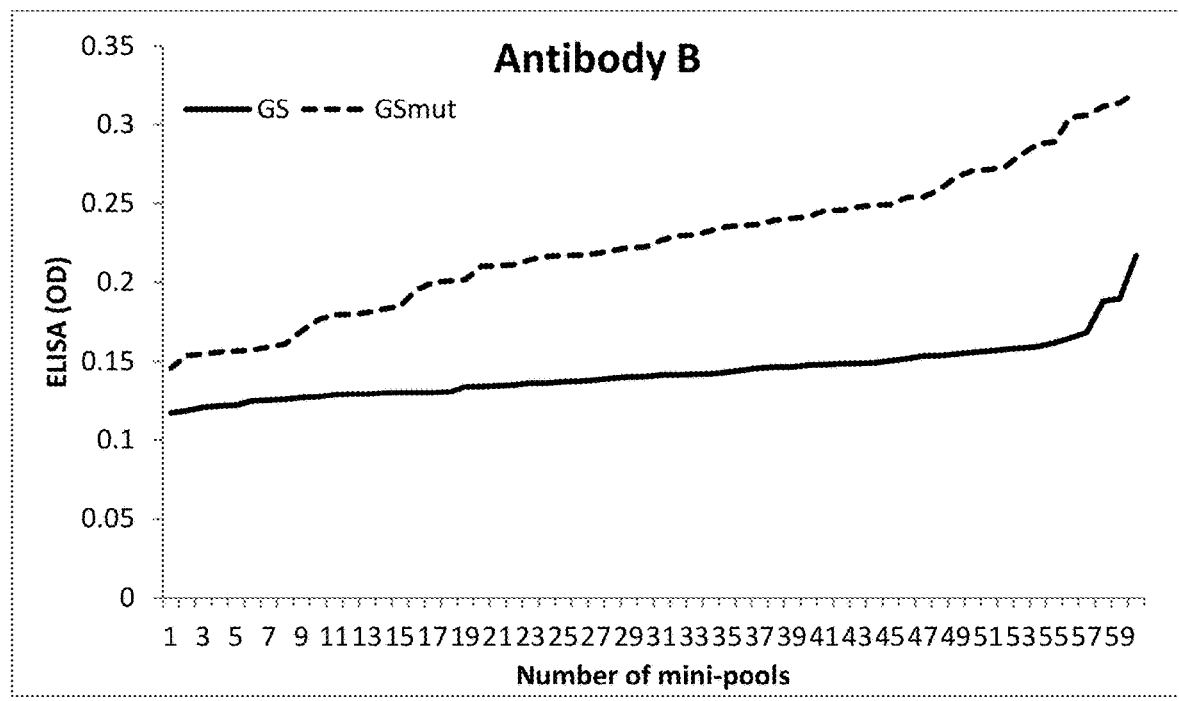

1×10$^7$ cells with 5 μg of DNA per transfection was performed for each of the construct. Two different antibodies were tested—Antibody A and B. Three days post-transfection, a small aliquot from WT GS and GSatt transfectants were each seeded into a 96 well plate at 2000 cells/well in 50/50 media (CD CHO/Hyclone) without L-Glutamine selection media. The cells were passaged once 2 weeks later and incubated for another 2 weeks for overgrowth assay. The supernatants were collected and their OD readings were evaluated in an ELISA format using anti-human antibody as the capture agent. The OD readings for both WT GS and GSatt were collected and tabulated in FIG. 1. Overall, the GSatt minipools showed an enhanced antibody production level over that of WT GS for both GA101 and Rituximab. Transfection of CHOK1 GFT$^{-/-}$ GS$^{-/-}$ with Either Tricistronic mAb-GS or Tricistronic mAb-GSatt (R324C)-Stable Suspension Pool Format.

Mutation of the GS gene at site -R324 to C (GSatt), corresponding to the glutamate binding region of the enzyme was made. The vector encoding an antibody gene and the GSatt selection marker in the tricistronic vector (Ho S C et. al., 2012) was compared with the wild type GS in the same format. The comparison in stable productivity level was done in CHO-K1 GFT$^{-/-}$ GS$^{-/-}$ cells. The stable productions of 2 different antibodies were tested.

Three transfections per construct (1×10$^7$ cells with 5 μg of DNA per transfection) were performed. Two different antibodies were tested—Antibody A and B. The transfectant pools were selected in 50/50 media (CD CHO/Hyclone) without L-Glutamine until they recover. Upon recovery, a batch culture was performed to determine the productivity. The WT GS and GSatt pools took an average of about 3.5 weeks and 6.5 weeks to recover respectively before the batch culture was performed.

Figure 2A:
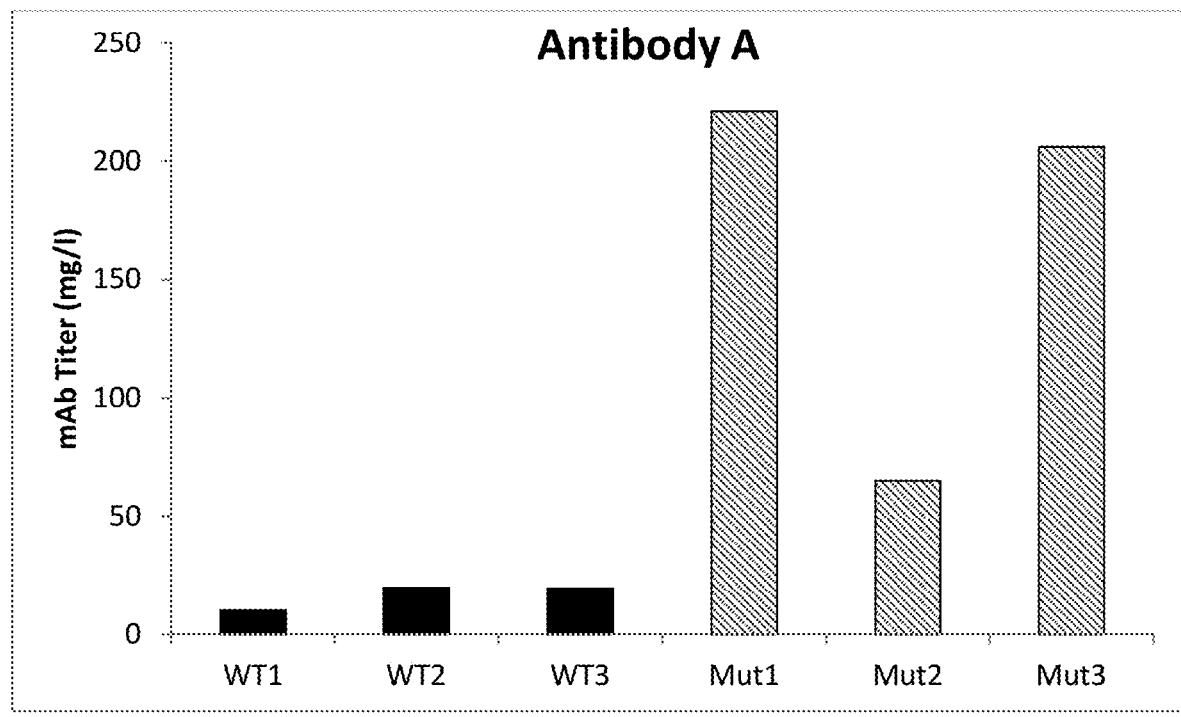
FIG. 2A depicts the experimental result for Antibody A; demonstrating that amount of mAb titer produced using Tricistronic mAb-GSatt (R324C) (data labeled as Mut1, Mut2, and Mut3) is approximately 9.9-fold more than amount of mAb titer produced using Tricistronic mAb-GS (data labeled as WT1, WT2, and WT3).
Figure 2B:
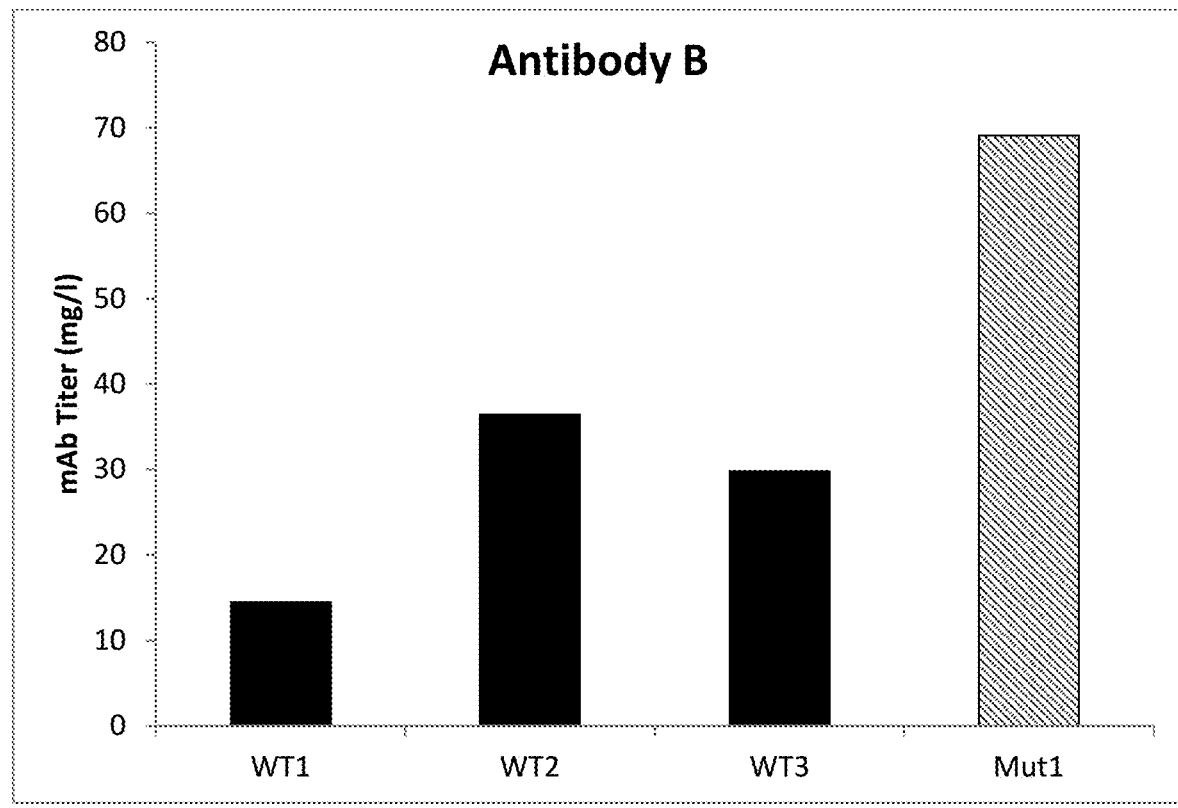
FIG. 2B depicts the experimental result for Antibody B; demonstrating that amount of mAb titer produced using Tricistronic mAb-GSatt (R324C) (data labeled as Mut1) is approximately 2.6-fold more than amount of mAb titer produced using Tricistronic mAb-GS (data labeled as WT1, WT2, and WT3). Thus.

The experimental result for Antibody A was shown in FIG. 2A. All 3 pools with the GSatt selection maker (Mut1-3) demonstrated significantly higher level of mAb titer over that of the wild type GS (WT1-3). The GSatt pools showed at average of 9.9-fold more titer than the WT GS pools. The experimental result for Antibody B was shown in FIG. 2B. Two pools for the Antibody B-GSatt did not survive. The remaining pool (Mutt) showed at least 2.6× more titer than the average of the 3 WT pools. Based on the results shown on FIGS. 2A and 2B, the use of GSatt can enhance the stable production of 2 different antibodies in CHO cells.

Several Novel Sites on the GS, when Mutated to Alanine, would Attenuate the GS Activity.

Figure 4:
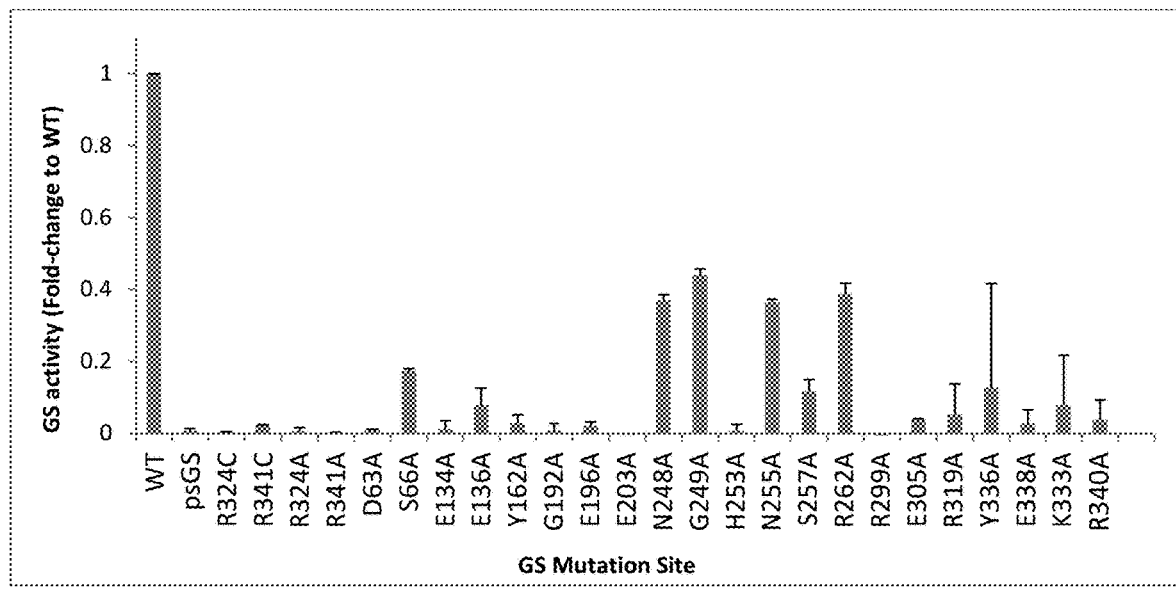
FIG. 4 shows a bar graph depicting the comparison of the GS activities of WT GS and several GS mutants.
Figure 5:
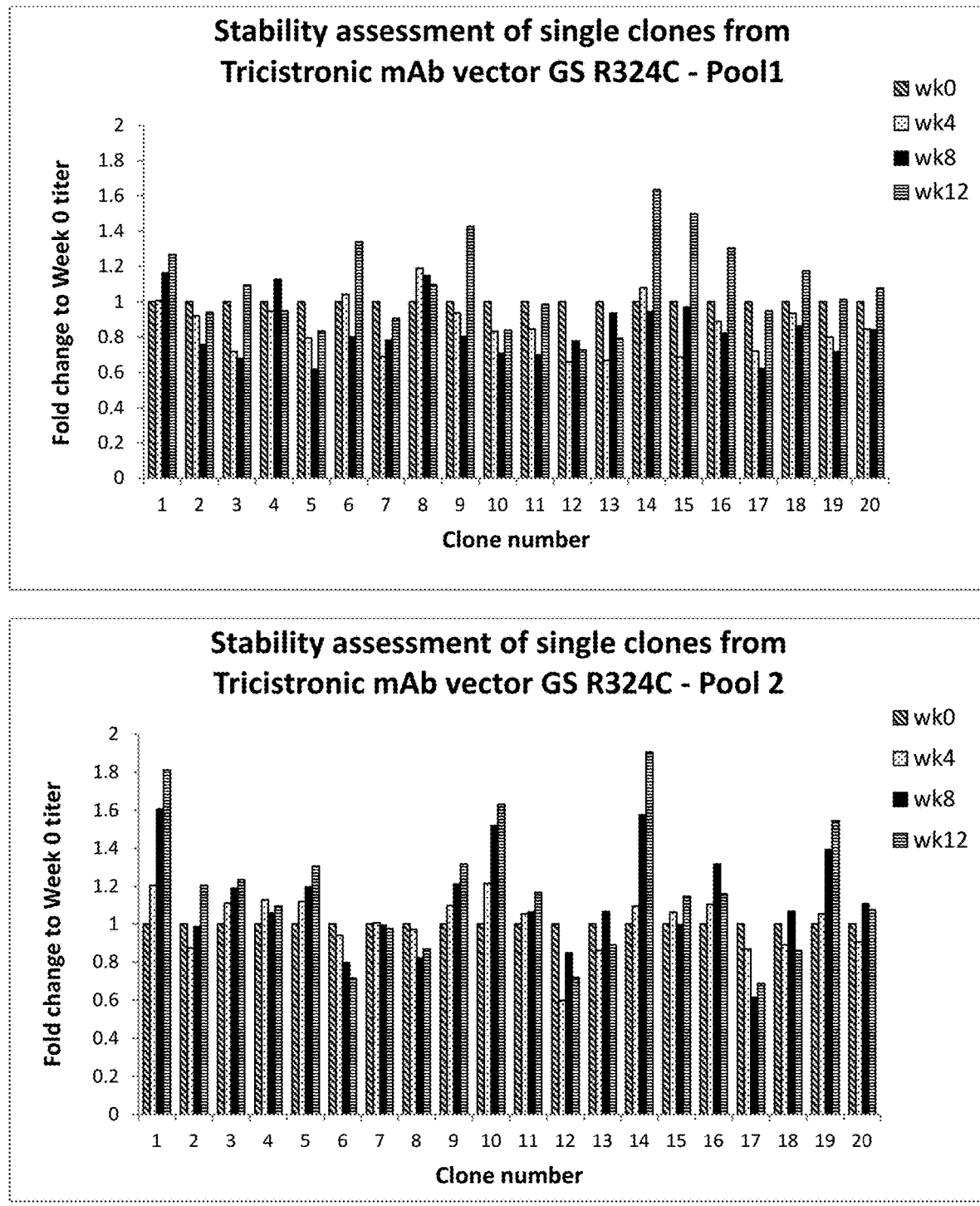
FIG. 5 shows a bar graph depicting the stability assessment of 20 single clones derived from 2 stable pools (top: pool 1, bottom: pool 2) transfected with Tricistronic mAb-GSatt (R324C) (SEQ ID NO: 85). Thus.

The methods to prepare GS constructs, measure GS activity, and measure luciferase activity were described in the Materials and Methods section. FIG. 4 represented an actual percentage of the GS activity normalized to that of WT GS activity. The GS activities, before luciferase normalization, were blanked with an untransfected CHO-K1 GS$^{-/-}$ cell lysate. The expression variations across the GS constructs were normalized accordingly via their luciferase activities. It was noted that the GS activity assay might not be sensitive enough for very low GS activity such that the known R342C and R341C mutants have near blank level activities. Nevertheless, the attenuation caused by the different mutations can be clearly observed. This result was a representative of two independent experiments.

Stability Assessment of the mAb Producing Clones Selected Using the GS Mutant.

Stability assessment of 20 single clones derived from 2 stable pools transfected with Tricistronic mAb GS construct. The mAb production of these single clones was measured over 12 weeks (about 60 generations) to assess the stability of these clones. The mAb titer of week 12 was divided over that of week 0 to obtain the fold change. Typically, stability level of 70% and above is defined as an acceptable level of stability for the stable clone. The graph showed that almost all the single clones except for clone 17 of stable pool2 (68%) was above the 70% benchmark. This is a relatively high percentage (>95%) of clones with the desired level of stability. This results support the advantage of using attenuated GS as the selection marker as the selection pressure is constantly present. The single clones are isolated from the pools containing the R324C mutation.

Comparison of the mAb Titers Generated Using the Wild-type (Wt) GS and GS Mutants as the Selection Markers.

Figure 8:
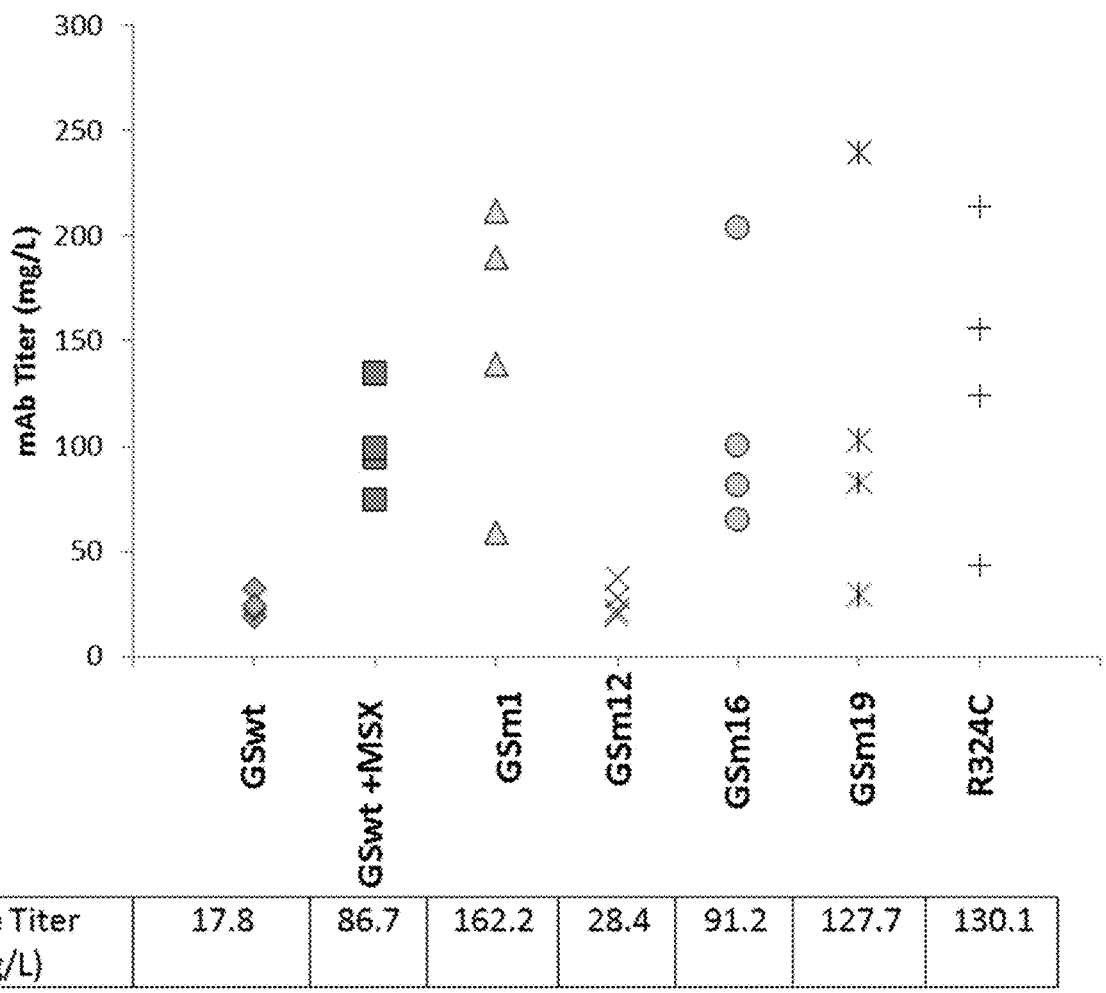
FIG. 8 shows a combined scatter plot and table depicting the comparisons of the amount of mAb titers generated using WT GS and GS mutants as selection markers in CHO-K1 GS$^{-/-}$ cells. For the WT samples, samples labeled as "GSwt" were not subjected to MSX selection while samples labeled as "GSwt+MSX" were subjected to 25 µM MSX selection. For the GS mutant samples, "GSm1" corresponds to GS having D63A mutation site, "GSm12" corresponds to GS having N248A mutation site, "GSm16" corresponds to GS having S257A mutation site, "GSm19" corresponds to GS having E305A mutation site, and "R324C" corresponds to GS having R324C mutation site. Thus.

The selection marker was incorporated into the tricistronic vector expressing Antibody A and transfected into CHO-K1 GS$^{-/-}$ cells. The selection was performed by removing L-glutamine from the media. For GSwt+MSX, after recovery from L-glutamine free media, the stable pools were then subjected to 25 μM MSX selection. The batch-culture titer for each stable pools generated is represented as a data point in the graph as shown on FIG. 8.

Stability Assessment of 5 Random Clones from Stable Pools Generated Using GSwt or GSm16 as the Selection Marker.

Stable pools of GA101 expressing CHO-K1 GS$^{-/-}$ cells were generated using either the GSwt (wild type GS) or GSm16 (GS having S257A mutation site) selection marker in the tricistronic vector. Five random clones from each pool were scaled up for stability assessment in growth media without MSX and L-glutamine. Batch-culture titers were measure every 4 weeks. As depicted on FIG. 9, the results showed that only 2 out of 5 GSwt clones were stable (i.e. maintained at least 70% of its original titer level) whereas 4 out of 5 GSm16 clones were stable.

The invention claimed is:

1. An expression vector comprising a polynucleotide encoding an attenuated glutamine synthetase comprising a single amino acid substitution with alanine at position 305 of a wild type glutamine synthetase comprising the amino acid sequence set forth in SEQ ID NO: 2.

2. The expression vector of claim 1, wherein the polynucleotide encoding the attenuated glutamine synthetase is operatively linked to a promoter.

3. The expression vector of claim 1, wherein the polynucleotide encoding the attenuated glutamine synthetase is not linked to a promoter.

4. A kit comprising the expression vector of claim 1.

5. The kit of claim 4, wherein the kit further comprises at least one of the following:

(i) a host cell having no glutamine synthetase activity; and

(11) a transfection medium or means to carry out a transfection;

and/or wherein the kit further comprises a glutamine free cell culture medium.

* * * * *

SEQUENCE LISTING

```
<160> NUMBER OF SEQ ID NOS: 103

<210> SEQ ID NO 1
<211> LENGTH: 373
<212> TYPE: PRT
<213> ORGANISM: Homo sapiens

<400> SEQUENCE: 1

Met Thr Thr Ser Ala Ser Ser His Leu Asn Lys Gly Ile Lys Gln Val
1               5                   10                  15

Tyr Met Ser Leu Pro Gln Gly Glu Lys Val Gln Ala Met Tyr Ile Trp
            20                  25                  30

Ile Asp Gly Thr Gly Glu Gly Leu Arg Cys Lys Thr Arg Thr Leu Asp
        35                  40                  45

Ser Glu Pro Lys Cys Val Glu Glu Leu Pro Glu Trp Asn Phe Asp Gly
    50                  55                  60

Ser Ser Thr Leu Gln Ser Glu Gly Ser Asn Ser Asp Met Tyr Leu Val
65                  70                  75                  80

Pro Ala Ala Met Phe Arg Asp Pro Phe Arg Lys Asp Pro Asn Lys Leu
                85                  90                  95

Val Leu Cys Glu Val Phe Lys Tyr Asn Arg Arg Pro Ala Glu Thr Asn
            100                 105                 110

Leu Arg His Thr Cys Lys Arg Ile Met Asp Met Val Ser Asn Gln His
        115                 120                 125

Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
```

```
                145                 150                 155                 160
Tyr Tyr Cys Gly Val Gly Ala Asp Arg Ala Tyr Gly Arg Asp Ile Val
                    165                 170                 175
Glu Ala His Tyr Arg Ala Cys Leu Tyr Ala Gly Val Lys Ile Ala Gly
                    180                 185                 190
Thr Asn Ala Glu Val Met Pro Ala Gln Trp Glu Phe Gln Ile Gly Pro
                    195                 200                 205
Cys Glu Gly Ile Ser Met Gly Asp His Leu Trp Val Ala Arg Phe Ile
                    210                 215                 220
Leu His Arg Val Cys Glu Asp Phe Gly Val Ile Ala Thr Phe Asp Pro
225                 230                 235                 240
Lys Pro Ile Pro Gly Asn Trp Asn Gly Ala Gly Cys His Thr Asn Phe
                    245                 250                 255
Ser Thr Lys Ala Met Arg Glu Glu Asn Gly Leu Lys Tyr Ile Glu Glu
                    260                 265                 270
Ala Ile Glu Lys Leu Ser Lys Arg His Gln Tyr His Ile Arg Ala Tyr
                    275                 280                 285
Asp Pro Lys Gly Gly Leu Asp Asn Ala Arg Arg Leu Thr Gly Phe His
                    290                 295                 300
Glu Thr Ser Asn Ile Asn Asp Phe Ser Ala Gly Val Ala Asn Arg Ser
305                 310                 315                 320
Ala Ser Ile Arg Ile Pro Arg Thr Val Gly Gln Glu Lys Lys Gly Tyr
                    325                 330                 335
Phe Glu Asp Arg Arg Pro Ser Ala Asn Cys Asp Pro Phe Ser Val Thr
                    340                 345                 350
Glu Ala Leu Ile Arg Thr Cys Leu Leu Asn Glu Thr Gly Asp Glu Pro
                    355                 360                 365
Phe Gln Tyr Lys Asn
         370

<210> SEQ ID NO 2
<211> LENGTH: 373
<212> TYPE: PRT
<213> ORGANISM: Cricetulus griseus

<400> SEQUENCE: 2

Met Ala Thr Ser Ala Ser Ser His Leu Asn Lys Asn Ile Lys Gln Met
1               5                   10                  15
Tyr Leu Cys Leu Pro Gln Gly Glu Lys Val Gln Ala Met Tyr Ile Trp
                    20                  25                  30
Val Asp Gly Thr Gly Glu Gly Leu Arg Cys Lys Thr Arg Thr Leu Asp
                    35                  40                  45
Cys Glu Pro Lys Cys Val Glu Glu Leu Pro Glu Trp Asn Phe Asp Gly
50                  55                  60
Ser Ser Thr Phe Gln Ser Glu Gly Ser Asn Ser Asp Met Tyr Leu Ser
65                  70                  75                  80
Pro Val Ala Met Phe Arg Asp Pro Phe Arg Asp Pro Asn Lys Leu
                    85                  90                  95
Val Phe Cys Glu Val Phe Lys Tyr Asn Arg Lys Pro Ala Glu Thr Asn
                    100                 105                 110
Leu Arg His Ser Cys Lys Arg Ile Met Asp Met Val Ser Asn Gln His
                    115                 120                 125
Pro Trp Phe Gly Met Glu Gln Glu Tyr Thr Leu Met Gly Thr Asp Gly
                    130                 135                 140
```

```
His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
            165                 170                 175

Glu Ala His Tyr Arg Ala Cys Leu Tyr Ala Gly Val Lys Ile Thr Gly
                180                 185                 190

Thr Asn Ala Glu Val Met Pro Ala Gln Trp Glu Phe Gln Ile Gly Pro
            195                 200                 205

Cys Glu Gly Ile Arg Met Gly Asp His Leu Trp Val Ala Arg Phe Ile
210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys His Ile Glu Glu
            260                 265                 270

Ala Ile Glu Lys Leu Ser Lys Arg His Arg Tyr His Ile Arg Ala Tyr
            275                 280                 285

Asp Pro Lys Gly Gly Leu Asp Asn Ala Arg Arg Leu Thr Gly Phe His
290                 295                 300

Glu Thr Ser Asn Ile Asn Asp Phe Ser Ala Gly Val Ala Asn Arg Ser
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Phe Ala Val Thr
            340                 345                 350

Glu Ala Ile Val Arg Thr Cys Leu Leu Asn Glu Thr Gly Asp Glu Pro
            355                 360                 365

Phe Gln Tyr Lys Asn
            370

<210> SEQ ID NO 3
<211> LENGTH: 373
<212> TYPE: PRT
<213> ORGANISM: Mus musculus

<400> SEQUENCE: 3

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
        35                  40                  45

Cys Glu Pro Lys Cys Val Glu Leu Pro Glu Trp Asn Phe Asp Gly
    50                  55                  60

Ser Ser Thr Phe Gln Ser Glu Gly Ser Asn Ser Asp Met Tyr Leu His
65                  70                  75                  80

Pro Val Ala Met Phe Arg Asp Pro Phe Arg Lys Asp Pro Asn Lys Leu
                85                  90                  95

Val Leu Cys Glu Val Phe Lys Tyr Asn Arg Lys Pro Ala Glu Thr Asn
            100                 105                 110

Leu Arg His Ile Cys Lys Arg Ile Met Asp Met Val Ser Asn Gln His
        115                 120                 125

Pro Trp Phe Gly Met Glu Gln Glu Tyr Thr Leu Met Gly Thr Asp Gly
130                 135                 140
```

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
            165                 170                 175

Glu Ala His Tyr Arg Ala Cys Leu Tyr Ala Gly Val Lys Ile Thr Gly
        180                 185                 190

Thr Asn Ala Glu Val Met Pro Ala Gln Trp Glu Phe Gln Ile Gly Pro
    195                 200                 205

Cys Glu Gly Ile Arg Met Gly Asp His Leu Trp Ile Ala Arg Phe Ile
210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Cys Ile Glu Glu
            260                 265                 270

Ala Ile Asp Lys Leu Ser Lys Arg His Gln Tyr His Ile Arg Ala Tyr
        275                 280                 285

Asp Pro Lys Gly Gly Leu Asp Asn Ala Arg Arg Leu Thr Gly Phe His
    290                 295                 300

Glu Thr Ser Asn Ile Asn Asp Phe Ser Ala Gly Val Ala Asn Arg Gly
305                 310                 315                 320

Ala Ser Ile Arg Ile Pro Arg Thr Val Gly Gln Lys Lys Gly Tyr
                325                 330                 335

Phe Glu Asp Arg Arg Pro Ser Ala Asn Cys Asp Pro Tyr Ala Val Thr
                340                 345                 350

Glu Ala Ile Val Arg Thr Cys Leu Leu Asn Glu Thr Gly Asp Glu Pro
            355                 360                 365

Phe Gln Tyr Lys Asn
        370

<210> SEQ ID NO 4
<211> LENGTH: 373
<212> TYPE: PRT
<213> ORGANISM: Rattus norvegicus

<400> SEQUENCE: 4

Met Ala Thr Ser Ala Ser Ser His Leu Asn Lys Gly Ile Lys Gln Met
1               5                   10                  15

Tyr Met Asn Leu Pro Gln Gly Glu Lys Ile Gln Leu Met Tyr Ile Trp
            20                  25                  30

Val Asp Gly Thr Gly Glu Gly Leu Arg Cys Lys Thr Arg Thr Leu Asp
        35                  40                  45

Cys Asp Pro Lys Cys Val Glu Glu Leu Pro Glu Trp Asn Phe Asp Gly
    50                  55                  60

Ser Ser Thr Phe Gln Ser Glu Gly Ser Asn Ser Asp Met Tyr Leu His
65                  70                  75                  80

Pro Val Ala Met Phe Arg Asp Pro Phe Arg Arg Asp Pro Asn Lys Leu
                85                  90                  95

Val Phe Cys Glu Val Phe Lys Tyr Asn Arg Lys Pro Ala Glu Thr Asn
            100                 105                 110

Leu Arg His Ser Cys Lys Arg Ile Met Asp Met Val Ser Ser Gln His
        115                 120                 125

Pro Trp Phe Gly Met Glu Gln Glu Tyr Thr Leu Met Gly Thr Asp Gly

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Ile Lys Ile Thr Gly
            180                 185                 190

Thr Asn Ala Glu Val Met Pro Ala Gln Trp Glu Phe Gln Ile Gly Pro
        195                 200                 205

Cys Glu Gly Ile Arg Met Gly Asp His Leu Trp Val Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Arg Cys Ile Glu Glu
            260                 265                 270

Ala Ile Asp Lys Leu Ser Lys Arg His Gln Tyr His Ile Arg Ala Tyr
        275                 280                 285

Asp Pro Lys Gly Gly Leu Asp Asn Ala Arg Arg Leu Thr Gly Phe His
    290                 295                 300

Glu Thr Ser Asn Ile Asn Asp Phe Ser Ala Gly Val Ala Asn Arg Ser
305                 310                 315                 320

Ala Ser Ile Arg Ile Pro Arg Ile Val Gly Gln Glu Lys Lys Gly Tyr
                325                 330                 335

Phe Glu Asp Arg Arg Pro Ser Ala Asn Cys Asp Pro Tyr Ala Val Thr
            340                 345                 350

Glu Ala Ile Val Arg Thr Cys Leu Leu Asn Glu Thr Gly Asp Glu Pro
        355                 360                 365

Phe Gln Tyr Lys Asn
    370

<210> SEQ ID NO 5
<211> LENGTH: 8201
<212> TYPE: DNA
<213> ORGANISM: Artificial Sequence
<220> FEATURE:
<223> OTHER INFORMATION: Biscistronic mAb GS

<400> SEQUENCE: 5
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660

```
                                                           -continued actcacgggg atttccaagt ctccacccca ttgacgtcaa tgggagtttg ttttggcacc      720
aaaatcaacg ggactttcca aaatgtcgta acaactccgc cccattgacg caaatgggcg      780
gtaggcgtgt acggtgggag gtctatataa gcagagctct ctggctaact agagaaccca     840
ctgcttactg gcttatcgaa attaatacga ctcactatag ggagacccaa gctggctagc      900
gtttaaactt aagcttggta ccgagctcgg atccactagt ccagtgtggt ggaattctgc      960
agatatccag cacagtggcg gccgccacca tggacatgag ggtccctgct cagtcctgg     1020 ggctcctgct gctctggctc tcaggtgcca gatgtgacat tgtaatgaca cagaccccac     1080
tctccctgcc cgtcacccct ggagagccgg cctccatctc ctgcaggtct agtaagagcc     1140
tcctgcatag taatggaatc acctatttgt actggtacct gcagaagcca gggcagtctc     1200
cacagctcct gatctatcag atgtctaatc tggtgtccgg ggtccctgac aggttcagtg     1260
gcagtggatc aggcacagat tttacactga aaatcagcag agtggaggct gaggatgttg     1320
gggtttatta ctgcgcccaa aacctagagc tgccctacac tttcggcgga gggaccaagg     1380
tggagatcaa acgtaccgtg gcggcgccat ctgtcttcat cttcccgcca tctgatgagc     1440
agttgaaatc tggaactgcc tctgttgtgt gcctgctgaa taacttctat cccagagagg     1500
ccaaagtaca gtggaaggtg gataacgccc tccaatcggg taactcccag gagagtgtca     1560
cagagcagga cagcaaggac agcacctaca gcctcagcag caccctgacg ctgagcaaag     1620
cagactacga gaaacacaaa gtctacgcct gcgaagtcac ccatcagggc ctgagctcgc     1680
ccgtcacaaa gagcttcaac aggggagagt gttagtagga tatcgtctag acccctctcc     1740 ctccccccc cctaacgtta ctggccgaag ccgcttggaa taaggccggt gtgcgtttgt     1800
ctatatgtta ttttccacca tattgccgtc ttttggcaat gtgagggccc ggaaacctgg     1860
ccctgtcttc ttgacgagca ttcctagggg tctttcccct ctcgccaaag gaatgcaagg     1920
tctgttgaat gtcgtgaagg aagcagttcc tctggaagct tcttgaagac aaacaacgtc     1980
tgtagcgacc ctttgcaggc agcggaaccc cccacctggc gacaggtgcc tctgcggcca     2040
aaagccacgt gtataagata cacctgcaaa ggcggcacaa ccccagtgcc acgttgtgag     2100
ttggatagtt gtggaaagag tcaaatggct ctcctcaagc gtattcaaca aggggctgaa     2160
ggatgcccag aaggtacccc attgtatggg atctgatctg gggcctcggt acacatgctt     2220
tacatgtgtt tagtcgaggt taaaaaaacg tctaggcccc ccgaaccacg ggacgtggt      2280 tttcctttga aaaacacgat gataatatgg ccacaaccat ggagtttggg ctgagctggg     2340
ttttcctcgt tgctcttttt agaggtgtcc agtgtcaggt gcagctggtg cagtctgggg     2400
ctgaggtgaa gaagcctggg tcctccgtga aggtctcctg caaggcctct ggatacgcct     2460
tctcctactc ttggatcaac tgggtgcgac aggcccctgg acaagggctc gagtggatgg     2520
gacggatctt ccctggcgat ggtgacacag actacaacgg caagttcaag ggcagagtca     2580
ccatcaccgc cgacaagtcc acgagcacag cctacatgga actgagcagc ctgagatctg     2640
aggacacggc cgtctattac tgtgcacgaa acgtgttcga tggctattgg ctggtgtact     2700
ggggccaggg gaccctggtc accgtcagca gcgctagcac caagggccca tcggtcttcc     2760
ccctggcacc ctcctccaag agcacctctg gggcacagc ggccctgggc tgcctggtca     2820
aggactactt ccccgaaccg gtgacggtgt catggaactc aggcgccctg accagcggcg     2880
tgcacacctt cccggctgtc ctacagtcct caggactcta ctccctcagc agcgtggtga     2940
ccgtgccctc cagcagcttg ggcacccaga cctacatctg caacgtgaat cacaagccca     3000
gcaacaccaa ggtggacaag aaagttgagc ccaaatcttg tgacaaaact cacacatgcc     3060
```

```
caccgtgccc agcacctgaa ctcctggggg gaccgtcagt cttcctcttc cccccaaaac   3120
ccaaggacac cctcatgatc tcccggaccc ctgaggtcac atgcgtggtg gtggacgtga   3180
gccacgaaga ccctgaggtc aagttcaact ggtacgtgga cggcgtggag gtgcataatg   3240
ccaagacaaa gccgcgggag gagcagtaca acagcacgta ccgtgtggtc agcgtcctca   3300
ccgtcctgca ccaggactgg ctgaatggca aggagtacaa gtgcaaggtc tccaacaaag   3360
ccctcccagc ccccatcgag aaaaccatct ccaaagccaa agggcagccc cgagaaccac   3420
aggtgtacac cctgccccca tcccgggatg agctgaccaa gaaccaggtc agcctgacct   3480
gcctggtcaa aggcttctat cccagcgaca tcgccgtgga gtgggagagc aatgggcagc   3540
cggagaacaa ctacaagacc acgcctcccg tgctggactc cgacggctcc ttcttcctct   3600
acagcaagct caccgtggac aagagcaggt ggcagcaggg gaacgtcttc tcatgctccg   3660
tgatgcatga ggctctgcac aaccactaca cgcagaagag cctctccctg tctccgggta   3720
aatgatcgag tctagagggc ccgtttaaac ccgctgatca gcctcgactg tgccttctag   3780
gcggccgctt gccagccatc tgttgtttgc cctcccccg tgccttcctt gaccctggaa   3840
ggtgccactc ccactgtcct ttcctaataa aatgaggaaa ttgcatcgca ttgtctgagt   3900
aggtgtcatt ctattctggg gggtggggtg gggcaggaca gcaggggga ggattgggaa   3960
gacaatagca ggcatgctgg ggatgcggtg ggctctatgg cttctgaggc ggaaagaacc   4020
agctggggct ctagggggta tccccacgcg ccctgtagcg gcgcattaag cgcggcgggt   4080
gtggtggtta cgcgcagcgt gaccgctaca cttgccagcg ccctagcgcc cgctcctttc   4140
gctttcttcc cttcctttct cgccacgttc gccggtctgt ggaatgtgtg tcagttaggg   4200
tgtggaaagt ccccaggctc cccagcaggc agaagtatgc aaagcatgca tctcaattag   4260
tcagcaacca ggtgtggaaa gtccccaggc tccccagcag gcagaagtat gcaaagcatg   4320
catctcaatt agtcagcaac catagtcccg cccctaactc cgcccatccc gcccctaact   4380
ccgcccagtt ccgcccattc tccgccccat ggctgactaa ttttttttat ttatgcagag   4440
gccgaggccg cctctgcctc tgagctattc cagaagtagt gaggaggctt ttttggaggc   4500
ctaggctttt gcaaaaagct cccgggagct tgtatatcca ttttcggatc tgatcaagag   4560
acaggatgag gatcggccac catggccacc tcagcaagtt cccacttgaa caaaaacatc   4620
aagcaaatgt acttgtgcct gccccagggt gagaaagtcc aagccatgta tatctgggtt   4680
gatggtactg gagaaggact gcgctgcaaa acccgcaccc tggactgtga gcccaagtgt   4740
gtagaagagt tacctgagtg gaattttgat ggctctagta cctttcagtc tgagggctcc   4800
aacagtgaca tgtatctcag ccctgttgcc atgtttcggg accccttccg cagagatccc   4860
aacaagctgg tgttctgtga gttttcaag tacaaccgga agcctgcaga gaccaattta   4920
aggcactcgt gtaaacggat aatggacatg gtgagcaacc agcacccctg gtttggaatg   4980
gaacaggagt atactctgat gggaacagat gggcacccct ttggttggcc ttccaatggc   5040
tttcctgggc cccaaggtcc gtattactgt ggtgtgggcg cagacaaagc ctatggcagg   5100
gatatcgtgg aggctcacta ccgcgcctgc ttgtatgctg gggtcaagat tacaggaaca   5160
aatgctgagg tcatgcctgc ccagtgggaa ttccaaatag accctgtga aggaatccgc   5220
atgggagatc atctctgggt ggcccgtttc atcttgcatc gagtatgtga agactttggg   5280
gtaatagcaa ccttttgaccc caagcccatt cctgggaact ggaatggtgc aggctgccat   5340
accaaccttta gcaccaaggc catgcgggag gagaatggtc tgaagcacat cgaggaggcc   5400
```

```
atcgagaaac taagcaagcg gcaccggtac cacattcgag cctacgatcc caaggggggc    5460
ctggacaatg cccgtcgtct gactgggttc cacgaaacgt ccaacatcaa cgactttct    5520
gctggtgtcg ccaatcgcag tgccagcatc cgcattcccc ggactgtcgg ccaggagaag   5580
aaaggttact ttgaagaccg ccgcccctct gccaattgtg accccttgc agtgacagaa    5640
gccatcgtcc gcacatgcct tctcaatgag actggcgacg agcccttcca atacaaaaac  5700
taagcgggac tctggggttc gaaatgaccg accaagcgac gcccaacctg ccatcacgag   5760
atttcgattc caccgccgcc ttctatgaaa ggttgggctt cggaatcgtt ttccgggacg   5820
ccggctggat gatcctccag cgcggggatc tcatgctgga gttcttcgcc cacccccaact  5880
tgtttattgc agcttataat ggttacaaat aaagcaatag catcacaaat ttcacaaata   5940
aagcattttt ttcactgcat tctagttgtg gtttgtccaa actcatcaat gtatcttatc   6000
atgtctgtat accgtcgacc tctagctaga gcttggcgta atcatggtca tagctgtttc   6060
ctgtgtgaaa ttgttatccg ctcacaattc cacacaacat acgagccgga agcataaagt   6120
gtaaagcctg gggtgcctaa tgagtgagct aactcacatt aattgcgttg cgctcactgc   6180
ccgctttcca gtcgggaaac ctgtcgtgcc agctgcatta tgaatcggc caacgcgcgg    6240
ggagaggcgg tttgcgtatt gggcgctctt ccgcttcctc gctcactgac tcgctgcgct   6300
cggtcgttcg gctgcggcga gcggtatcag ctcactcaaa ggcggtaata cggttatcca   6360
cagaatcagg ggataacgca ggaaagaaca tgtgagcaaa aggccagcaa aaggccagga   6420
accgtaaaaa ggccgcgttg ctggcgtttt tccataggct ccgcccccct gacgagcatc   6480
acaaaaatcg acgctcaagt cagaggtggc gaaacccgac aggactataa agataccagg   6540
cgtttccccc tggaagctcc ctcgtgcgct ctcctgttcc gaccctgccg cttaccggat   6600
acctgtccgc ctttctccct tcgggaagcg tggcgctttc tcatagctca cgctgtaggt   6660
atctcagttc ggtgtaggtc gttcgctcca agctgggctg tgtgcacgaa ccccccgttc   6720
agcccgaccg ctgcgcctta tccggtaact atcgtcttga gtccaacccg gtaagacacg   6780
acttatcgcc actggcagca gccactggta acaggattag cagagcgagg tatgtaggcg   6840
gtgctacaga gttcttgaag tggtggccta actacggcta cactagaaga acagtatttg   6900
gtatctgcgc tctgctgaag ccagttacct tcggaaaaag agttggtagc tcttgatccg   6960
gcaaacaaac caccgctggt agcggttttt ttgtttgcaa gcagcagatt acgcgcagaa   7020
aaaaaggatc tcaagaagat cctttgatct tttctacggg gtctgacgct cagtggaacg   7080
aaaactcacg ttaagggatt ttggtcatga gattatcaaa aaggatcttc acctagatcc   7140
ttttaaatta aaaatgaagt tttaaatcaa tctaaagtat atatgagtaa acttggtctg   7200
acagttacca atgcttaatc agtgaggcac ctatctcagc gatctgtcta tttcgttcat   7260
ccatagttgc ctgactcccc gtcgtgtaga taactacgat acgggagggc ttaccatctg   7320
gccccagtgc tgcaatgata ccgcgagacc cacgctcacc ggctccagat ttatcagcaa   7380
taaaccagcc agccggaagg gccgagcgca gaagtggtcc tgcaacttta tccgcctcca   7440
tccagtctat taattgttgc cgggaagcta gagtaagtag ttcgccagtt aatagtttgc   7500
gcaacgttgt tgccattgct acaggcatcg tggtgtcacg ctcgtcgttt ggtatggctt   7560
cattcagctc cggttcccaa cgatcaaggc gagttacatg atccccatg ttgtgcaaaa   7620
aagcggttag ctccttcggt cctccgatcg ttgtcagaag taagttggcc gcagtgttat   7680
cactcatggt tatggcagca ctgcataatt ctcttactgt catgccatcc gtaagatgct   7740
tttctgtgac tggtgagtac tcaaccaagt cattctgaga atagtgtatg cggcgaccga   7800
```

| | | |
|---|---|---|
| gttgctcttg cccggcgtca atacgggata ataccgcgcc acatagcaga actttaaaag | 7860 |
| tgctcatcat tggaaaacgt tcttcggggc gaaaactctc aaggatctta ccgctgttga | 7920 |
| gatccagttc gatgtaaccc actcgtgcac ccaactgatc ttcagcatct tttactttca | 7980 |
| ccagcgtttc tgggtgagca aaaacaggaa ggcaaaatgc cgcaaaaaag gaataagggc | 8040 |
| gacacggaa atgttgaata ctcatactct ccttttttca atattattga agcatttatc | 8100 |
| agggttattg tctcatgagc ggatacatat ttgaatgtat ttagaaaaat aaacaaatag | 8160 |
| gggttccgcg cacatttccc cgaaaagtgc cacctgacgt c | 8201 |

<210> SEQ ID NO 6
<211> LENGTH: 588
<212> TYPE: DNA
<213> ORGANISM: Artificial Sequence
<220> FEATURE:
<223> OTHER INFORMATION: CMV Promoter

<400> SEQUENCE: 6

| | | |
|---|---|---|
| gttgacattg attattgact agttattaat agtaatcaat tacgggtca ttagttcata | 60 |
| gcccatatat ggagttccgc gttacataac ttacggtaaa tggcccgcct ggctgaccgc | 120 |
| ccaacgaccc ccgcccattg acgtcaataa tgacgtatgt tcccatagta acgccaatag | 180 |
| ggactttcca ttgacgtcaa tgggtggagt atttacggta aactgcccac ttggcagtac | 240 |
| atcaagtgta tcatatgcca agtacgcccc ctattgacgt caatgacggt aaatggcccg | 300 |
| cctggcatta tgcccagtac atgaccttat gggactttcc tacttggcag tacatctacg | 360 |
| tattagtcat cgctattacc atggtgatgc ggttttggca gtacatcaat gggcgtggat | 420 |
| agcggtttga ctcacgggga tttccaagtc tccaccccat tgacgtcaat gggagtttgt | 480 |
| tttggcacca aaatcaacgg gactttccaa aatgtcgtaa caactccgcc ccattgacgc | 540 |
| aaatgggcgg taggcgtgta cggtgggagg tctatataag cagagctc | 588 |

<210> SEQ ID NO 7
<211> LENGTH: 729
<212> TYPE: DNA
<213> ORGANISM: Artificial Sequence
<220> FEATURE:
<223> OTHER INFORMATION: Light chain of antibody GA101 (LC 1-729)

<400> SEQUENCE: 7

| | | |
|---|---|---|
| atggacatga gggtccctgc tcagctcctg gggctcctgc tgctctggct ctcaggtgcc | 60 |
| agatgtgaca ttgtaatgac acagacccca ctctccctgc ccgtcacccc tggagagccg | 120 |
| gcctccatct cctgcaggtc tagtaagagc ctcctgcata gtaatggaat cacctatttg | 180 |
| tactggtacc tgcagaagcc agggcagtct ccacagctcc tgatctatca gatgtctaat | 240 |
| ctggtgtccg ggtccctga caggttcagt ggcagtggat caggcacaga ttttacactg | 300 |
| aaaatcagca gagtggaggc tgaggatgtt ggggtttatt actgcgccca aaacctagag | 360 |
| ctgcccctaca ctttcggcgg agggaccaag gtggagatca acgtaccgt ggcggcgcca | 420 |
| tctgtcttca tcttcccgcc atctgatgag cagttgaaat ctggaactgc ctctgttgtg | 480 |
| tgcctgctga ataacttcta tcccagagag gccaaagtac agtggaaggt ggataacgcc | 540 |
| ctccaatcgg gtaactccca ggagagtgtc acagagcagg acagcaagga cagcacctac | 600 |
| agcctcagca gcaccctgac gctgagcaaa gcagactacg agaaacacaa agtctacgcc | 660 |
| tgcgaagtca cccatcaggg cctgagctcg cccgtcacaa agagcttcaa caggggagag | 720 | tgttagtag                                                               729

<210> SEQ ID NO 8
<211> LENGTH: 20
<212> TYPE: DNA
<213> ORGANISM: Artificial Sequence
<220> FEATURE:
<223> OTHER INFORMATION: Wild type Internal Ribosome Entry Site

<400> SEQUENCE: 8
atgataatat ggccacaacc                                                    20

<210> SEQ ID NO 9
<211> LENGTH: 1407
<212> TYPE: DNA
<213> ORGANISM: Artificial Sequence
<220> FEATURE:
<223> OTHER INFORMATION: Heavy chain of antibody GA101 (HC 1329-2747)

<400> SEQUENCE: 9
atggagtttg ggctgagctg ggttttcctc gttgctcttt ttagaggtgt ccagtgtcag         60
gtgcagctgg tgcagtctgg ggctgaggtg aagaagcctg gtcctccgt gaaggtctcc        120 tgcaaggcct ctggatacgc cttctcctac tcttggatca actgggtgcg acaggccct        180 ggacaagggc tcgagtggat gggacggatc ttccctggcg atggtgacac agactacaac        240
ggcaagttca gggcagagt caccatcacc gccgacaagt ccacgagcac agcctacatg        300
gaactgagca gcctgagatc tgaggacacg gccgtctatt actgtgcacg aaacgtgttc        360
gatggctatt ggctggtgta ctggggccag gggaccctgg tcaccgtcag cagcgctagc        420
accaagggcc catcggtctt ccccctggca ccctcctcca agagcacctc tgggggcaca        480
gcggccctgg gctgcctggt caaggactac ttccccgaac cggtgacggt gtcatggaac        540
tcaggcgccc tgaccagcgg cgtgcacacc ttcccggctg tcctacagtc ctcaggactc        600
tactccctca gcagcgtggt gaccgtgccc tccagcagct gggcacccca gacctacatc        660
tgcaacgtga atcacaagcc cagcaacacc aaggtggaca agaaagttga gcccaaatct        720
tgtgacaaaa ctcacacatg cccaccgtgc ccagcacctg aactcctggg gggaccgtca        780
gtcttcctct tccccccaaa acccaaggac accctcatga tctcccggac ccctgaggtc        840
acatgcgtgg tggtggacgt gagccacgaa gaccctgagg tcaagttcaa ctggtacgtg        900
gacggcgtgg aggtgcataa tgccaagaca agccgcggg aggagcagta caacagcacg        960
taccgtgtgg tcagcgtcct caccgtcctg caccaggact ggctgaatgg caaggagtac       1020
aagtgcaagg tctccaacaa agccctccca gcccccatcg agaaaaccat ctccaaagcc       1080
aaagggcagc cccgagaacc acaggtgtac accctgcccc catcccggga tgagctgacc       1140
aagaaccagg tcagcctgac ctgcctggtc aaaggcttct atcccagcga catcgccgtg       1200
gagtgggaga gcaatgggca gccggagaac aactacaaga ccacgcctcc cgtgctggac       1260
tccgacggct ccttcttcct ctacagcaag ctcaccgtgg acaagagcag gtggcagcag       1320
gggaacgtct tctcatgctc cgtgatgcat gaggctctgc acaaccacta cacgcagaag       1380
agcctctccc tgtctccggg taaatga                                          1407

<210> SEQ ID NO 10
<211> LENGTH: 232
<212> TYPE: DNA
<213> ORGANISM: Artificial Sequence
<220> FEATURE:
<223> OTHER INFORMATION: Bovine Growth Hormone Polyadenylation signal (BGH pA)

<400> SEQUENCE: 10

| tgtgccttct | aggcggccgc | ttgccagcca | tctgttgttt | gccctcccc | cgtgccttcc | 60 |
| ttgaccctgg | aaggtgccac | tcccactgtc | ctttcctaat | aaaatgagga | aattgcatcg | 120 |
| cattgtctga | gtaggtgtca | ttctattctg | ggggtgggg | tggggcagga | cagcaagggg | 180 |
| gaggattggg | aagacaatag | caggcatgct | ggggatgcgg | tgggctctat | gg | 232 |

<210> SEQ ID NO 11
<211> LENGTH: 17
<212> TYPE: DNA
<213> ORGANISM: Artificial Sequence
<220> FEATURE:
<223> OTHER INFORMATION: SV40 promoter

<400> SEQUENCE: 11
ctgtggaatg tgtgtca                                                17

<210> SEQ ID NO 12
<211> LENGTH: 1122
<212> TYPE: DNA
<213> ORGANISM: Artificial Sequence
<220> FEATURE:
<223> OTHER INFORMATION: Glutamine Synthetase (GS); Wild Type Glutamine
      Synthetase from CHO cell

<400> SEQUENCE: 12

| atggccacct | cagcaagttc | ccacttgaac | aaaaacatca | agcaaatgta | cttgtgcctg | 60 |
| ccccagggtg | agaaagtcca | agccatgtat | atctgggttg | atggtactgg | agaaggactg | 120 |
| cgctgcaaaa | cccgcaccct | ggactgtgag | cccaagtgtg | tagaagagtt | acctgagtgg | 180 |
| aattttgatg | gctctagtac | cttttcagtct | gagggctcca | acagtgacat | gtatctcagc | 240 |
| cctgttgcca | tgtttcggga | cccttccgc | agagatccca | acaagctggt | gttctgtgaa | 300 |
| gttttcaagt | acaaccggaa | gcctgcagag | accaatttaa | ggcactcgtg | taaacggata | 360 |
| atggacatgg | tgagcaacca | gcaccctctg | tttggaatgg | aacaggagta | tactctgatg | 420 |
| ggaacagatg | ggcaccctt | tggttggcct | tccaatggct | tcctgggcc | ccaaggtccg | 480 |
| tattactgtg | gtgtgggcgc | agacaaagcc | tatggcaggg | atatcgtgga | ggctcactac | 540 |
| cgcgcctgct | tgtatgctgg | ggtcaagatt | acaggaacaa | tgctgaggt | catgcctgcc | 600 |
| cagtgggaat | tccaaatagg | accctgtgaa | ggaatccgca | tgggagatca | tctctgggtg | 660 |
| gcccgtttca | tcttgcatcg | agtatgtgaa | gactttggg | taatagcaac | ctttgacccc | 720 |
| aagcccattc | ctgggaactg | gaatggtgca | ggctgccata | ccaactttag | caccaaggcc | 780 |
| atgcgggagg | agaatggtct | gaagcacatc | gaggaggcca | tcgagaaact | aagcaagcgg | 840 |
| caccggtacc | acattcgagc | ctacgatccc | aagggggcc | tggacaatgc | ccgtcgtctg | 900 |
| actgggttcc | acgaaacgtc | caacatcaac | gactttctg | ctggtgtcgc | caatcgcagt | 960 |
| gccagcatcc | gcattccccg | gactgtcggc | caggagaaga | aaggttactt | tgaagaccgc | 1020 |
| cgccctctg | ccaattgtga | ccctttgca | gtgacagaag | ccatcgtccg | cacatgcctt | 1080 |
| ctcaatgaga | ctggcgacga | gcccttccaa | tacaaaaact | aa | | 1122 |

<210> SEQ ID NO 13
<211> LENGTH: 130
<212> TYPE: DNA
<213> ORGANISM: Artificial Sequence
<220> FEATURE:

<223> OTHER INFORMATION: SV40 pA terminator sequence (SV40pA)

<400> SEQUENCE: 13

```
acttgtttat tgcagcttat aatggttaca aataaagcaa tagcatcaca aatttcacaa      60
ataaagcatt ttttcactg cattctagtt gtggtttgtc caaactcatc aatgtatctt      120
atcatgtctg                                                             130
```

<210> SEQ ID NO 14
<211> LENGTH: 7985
<212> TYPE: DNA
<213> ORGANISM: Artificial Sequence
<220> FEATURE:
<223> OTHER INFORMATION: Tricistronic mAb GS

<400> SEQUENCE: 14

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac tcgagtcctt agggagcgat ccagcacgag gagaggccgg gaggggcgg     660
gacggggcgg ggcctctggg agagtgggtt gcggggaggc tggcttttgg caggaagtaa     720
cgcatttgct ggactcgagt gatgcggttt tgcagtaca tcaatgggcg tggatagcgg     780
tttgactcac ggggatttcc aagtctccac cccattgacg tcaatgggag tttgttttgg     840
caccaaaatc aacgggactt tccaaaatgt cgtaacaact ccgcccatt gacgcaaatg     900
ggcggtaggc gtgtacggtg ggaggtctat ataagcagag ctctctggct agcgtttaaa     960
cttaagcttg gtaccgagct cggatccaga attcgccaca atggacatga gggtccctgc    1020
tcagctcctg gggctcctgc tgctctggct ctcaggtgcc agatgtgaca ttgtaatgac    1080
acagacccca ctctccctgc ccgtcacccc tggagagccg gcctccatct cctgcaggtc    1140
tagtaagagc ctcctgcata gtaatggaat cacctatttg tactggtacc tgcagaagcc    1200
agggcagtct ccacagctcc tgatctatca gatgtctaat ctggtgtccg ggtccctga    1260
caggttcagt ggcagtggat caggcacaga ttttacactg aaaatcagca gagtggaggc    1320
tgaggatgtt gggtttatt actgcgccca aaacctagag ctgccctaca ctttcggcgg    1380
agggaccaag gtggagatca aacgtaccgt ggcggcgcca tctgtcttca tcttcccgcc    1440
atctgatgag cagttgaaat ctggaactgc ctctgttgtg tgcctgctga ataacttcta    1500
tcccagagag gccaaagtac agtggaaggt ggataacgcc ctccaatcgg gtaactccca    1560
ggagagtgtc acagagcagg acagcaagga cagcacctac agcctcagca gcaccctgac    1620
gctgagcaaa gcagactacg agaaacacaa agtctacgcc tgcgaagtca cccatcaggg    1680
cctgagctcg cccgtcacaa agagcttcaa caggggagag tgttagtagg atatcgtcta    1740
gaccctcc cctcccccc cctaacgtt actggccgaa gccgcttgga ataaggccgg        1800
```

```
tgtgcgtttg tctatatgtt attttccacc atattgccgt cttttggcaa tgtgagggcc    1860
cggaaacctg gccctgtctt cttgacgagc attcctaggg gtctttcccc tctcgccaaa    1920
ggaatgcaag gtctgttgaa tgtcgtgaag gaagcagttc ctctggaagc ttcttgaaga    1980
caaacaacgt ctgtagcgac cctttgcagg cagcggaacc ccccacctgg cgacaggtgc    2040
ctctgcggcc aaaagccacg tgtataagat acacctgcaa aggcggcaca accccagtgc    2100
cacgttgtga gttggatagt tgtggaaaga gtcaaatggc tctcctcaag cgtattcaac    2160
aaggggctga aggatgccca gaaggtaccc cattgtatgg gatctgatct ggggcctcgg    2220
tacacatgct ttacatgtgt ttagtcgagg ttaaaaaaac gtctaggccc cccgaaccac    2280
ggggacgtgg ttttcctttg aaaaacacga tgataatatg ccacaaccca tggagtttgg    2340
gctgagctgg gttttcctcg ttgctctttt tagaggtgtc cagtgtcagg tgcagctggt    2400
gcagtctggg gctgaggtga agaagcctgg gtcctcgtg aaggtctcct gcaaggcctc    2460
tggatacgcc ttctcctact cttggatcaa ctgggtgcga caggccctg acaagggct    2520
cgagtggatg ggacggatct tccctggcga tggtgacaca gactacaacg caagttcaa    2580
gggcagagtc accatcaccg ccgacaagtc cacgagcaca gcctacatgg aactgagcag    2640
cctgagatct gaggacacgg ccgtctatta ctgtgcacga aacgtgttcg atggctattg    2700
gctggtgtac tggggccagg ggaccctggt caccgtcagc agcgctagca ccaagggccc    2760
atcggtcttc cccctggcac cctcctccaa gagcacctct gggggcacag cggccctggg    2820
ctgcctggtc aaggactact ccccgaacc ggtgacggtg tcatggaact caggcgccct    2880
gaccagcggc gtgcacacct tcccggctgt cctacagtcc tcaggactct actccctcag    2940
cagcgtggtg accgtgccct ccagcagctt gggcacccag acctacatct gcaacgtgaa    3000
tcacaagccc agcaacacca aggtggacaa gaaagttgag cccaaatctt gtgacaaaac    3060
tcacacatgc ccaccgtgcc cagcacctga actcctgggg ggaccgtcag tcttcctctt    3120
ccccccaaaa cccaaggaca ccctcatgat ctcccggacc cctgaggtca catgcgtggt    3180
ggtggacgtg agccacgaag accctgaggt caagttcaac tggtacgtgg acggcgtgga    3240
ggtgcataat gccaagacaa agccgcggga ggagcagtac aacagcacgt accgtgtggt    3300
cagcgtcctc accgtcctgc accaggactg gctgaatggc aaggagtaca agtgcaaggt    3360
ctccaacaaa gccctcccag cccccatcga gaaaaccatc tccaaagcca aagggcagcc    3420
ccgagaacca caggtgtaca ccctgccccc atcccgggat gagctgacca gaaccaggt    3480
cagcctgacc tgcctggtca aaggcttcta tcccagcgac atcgccgtgg agtgggagag    3540
caatgggcag ccggagaaca actacaagac cacgcctccc gtgctggact ccgacggctc    3600
cttcttcctc tacagcaagc tcaccgtgga caagagcagg tggcagcagg ggaacgtctt    3660
ctcatgctcc gtgatgcatg aggctctgca caaccactac acgcagaaga gcctctccct    3720
gtctccgggt aaatgaatcg atgcctgcag gtggccggcc acaccggtgc ccctctccct    3780
cccccccccc taacgttact ggccgaagcc gcttggaata aggccggtgt gcgtttgtct    3840
atatgttatt ttccaccata ttgccgtctt ttggcaatgt gagggcccgg aaacctggcc    3900
ctgtcttctt gacgagcatt cctaggggtc ttttcccctct cgccaaagga atgcaaggtc    3960
tgttgaatgt cgtgaaggaa gcagttcctc tggaagcttc ttgaagacaa acaacgtctg    4020
tagcgaccct ttgcaggcag cggaaccccc cacctggcga caggtgcctc tgcggccaaa    4080
agccacgtgt ataagataca cctgcaaagg cggcacaacc ccagtgccac gttgtgagtt    4140
```

-continued

```
ggatagttgt ggaaagagtc aaatggctct cctcaagcgt attcaacaag gggctgaagg      4200
atgcccagaa ggtaccccat tgtatgggat ctgatctggg gcctcggtac acatgcttta      4260
catgtgttta gtcgaggtta aaaaaacgtc taggcccccc gaaccacggg gacgtggttt      4320
tcctttgaaa aacacgatga taagcttgcc acaaccccgg gagatgagga tcgtttcgca      4380
tggccacctc agcaagttcc cacttgaaca aaaacatcaa gcaaatgtac ttgtgcctgc      4440
cccagggtga gaaagtccaa gccatgtata tctgggttga tggtactgga gaaggactgc      4500
gctgcaaaac ccgcaccctg gactgtgagc ccaagtgtgt agaagagtta cctgagtgga      4560
attttgatgg ctctagtacc tttcagtctg agggctccaa cagtgacatg tatctcagcc      4620
ctgttgccat gtttcgggac cccttccgca gagatcccaa caagctggtg ttctgtgaag      4680
ttttcaagta caaccggaag cctgcagaga ccaatttaag gcactcgtgt aaacggataa      4740
tggacatggt gagcaaccag caccctggt ttggaatgga acaggagtat actctgatgg      4800
gaacagatgg gcaccttttt ggttggcctt ccaatggctt tcctgggccc caaggtccgt      4860
attactgtgg tgtgggcgca gacaaagcct atggcaggga tatcgtggag ctcactacc      4920 gcgcctgctt gtatgctggg gtcaagatta caggaacaaa tgctgaggtc atgcctgccc      4980
agtgggaatt ccaaatagga ccctgtgaag gaatccgcat gggagatcat ctctgggtgg      5040 cccgttttcat cttgcatcga gtatgtgaag actttggggt aatagcaacc tttgacccca      5100
agcccattcc tgggaactgg aatggtgcag gctgccatac caactttagc accaaggcca      5160
tgcgggagga gaatggtctg aagcacatcg aggaggccat cgagaaacta agcaagcggc      5220
accggtacca cattcgagcc tacgatccca aggggggcct ggacaatgcc cgtcgtctga      5280
ctgggttcca cgaaacgtcc aacatcaacg acttttctgc tggtgtcgcc aatcgcagtg      5340
ccagcatccg cattccccgg actgtcgccc aggagaagaa aggttacttt gaagaccgcc      5400
gcccctctgc caattgtgac ccctttgcag tgacagaagc catcgtccgc acatgccttc      5460
tcaatgagac tggcgacgag cccttccaat acaaaaacta attcgaaatg accgaccaag      5520
cgacgcccaa cctgccatca cgagatttcg attccaccgc cgccttctat gaaaggttgg      5580
gcttcggaat cgttttccgg gacgccggct ggatgatcct ccagcgcggg gatctcatgc      5640
tggagttctt cgcccacccc aacttgttta ttgcagctta taatggttac aaataaagca      5700
atagcatcac aaatttcaca aataaagcat ttttttcact gcattctagt tgtggtttgt      5760
ccaaactcat caatgtatct tatcatgtct gtataccgtc gacctctagc tagagcttgg      5820
cgtaatcatg gtcatagctg tttcctgtgt gaaattgtta tccgctcaca attccacaca      5880
acatacgagc cggaagcata aagtgtaaag cctggcgcgc taatgagtg agctaactca      5940 cattaattgc gttgcgctca ctgcccgctt tccagtcggg aaacctgtcg tgccagctgc      6000
attaatgaat cggcgatcgc gcggggagag gcggtttgcg tattgggcgc tcttccgctt      6060
cctcgctcac tgactcgctg cgctcggtcg ttcggctgcg gcgagcggta tcagctcact      6120
caaaggcggt aatacggtta tccacagaat caggggataa cgcaggaaag aacatgtgag      6180
caaaaggcca gcaaaaggcc aggaaccgta aaaaggccgc gttgctggcg ttttccata      6240 ggctccgccc ccctgacgag catcacaaaa atcgacgctc aagtcagagg tggcgaaacc      6300
cgacaggact ataaagatac caggcgtttc ccctggaag ctccctcgtg cgctctcctg      6360
ttccgaccct gccgcttacc ggatacctgt ccgcctttct cccttcggga agcgtggcgc      6420
tttctcatag ctcacgctgt aggtatctca gttcggtgta ggtcgttcgc tccaagctgg      6480
gctgtgtgca cgaaccccc gttcagcccg accgctgcgc cttatccggt aactatcgtc      6540
```

```
ttgagtccaa cccggtaaga cacgacttat cgccactggc agcagccact ggtaacagga      6600
ttagcagagc gaggtatgta ggcggtgcta cagagttctt gaagtggtgg cctaactacg      6660
gctacactag aagaacagta tttggtatct gcgctctgct gaagccagtt accttcggaa      6720
aaagagttgg tagctcttga tccggcaaac aaaccaccgc tggtagcggt ttttttgttt      6780
gcaagcagca gattacgcgc agaaaaaaag gatctcaaga agatcctttg atcttttcta      6840
cggggtctga cgctcagtgg aacgaaaact cacgttaagg gattttggtc atgagattat      6900
caaaaaggat cttcacctag atccttttaa attaaaaatg aagttttaaa tcaatctaaa      6960
gtatatatga gtaaacttgg tctgacagtt accaatgctt aatcagtgag gcacctatct      7020
cagcgatctg tctatttcgt tcatccatag ttgcctgact ccccgtcgtg tagataacta      7080
cgatacggga gggcttacca tctggcccca gtgctgcaat gataccgcga gacccacgct      7140
caccggctcc agatttatca gcaataaacc agccagccgg aagggccgag cgcagaagtg      7200
gtcctgcaac tttatccgcc tccatccagt ctattaattg ttgccgggaa gctagagtaa      7260
gtagttcgcc agttaatagt ttgcgcaacg ttgttgccat tgctacaggc atcgtggtgt      7320
cacgctcgtc gtttggtatg gcttcattca gctccggttc ccaacgatca aggcgagtta      7380
catgatcccc catgttgtgc aaaaaagcgg ttagctcctt cggtcctccg atcgttgtca      7440
gaagtaagtt ggccgcagtg ttatcactca tggttatggc agcactgcat aattctctta      7500
ctgtcatgcc atccgtaaga tgcttttctg tgactggtga gtactcaacc aagtcattct      7560
gagaatagtg tatgcggcga ccgagttgct cttgcccggc gtcaatacgg gataataccg      7620
cgccacatag cagaacttta aaagtgctca tcattggaaa acgttcttcg ggcgaaaac      7680 tctcaaggat cttaccgctg ttgagatcca gttcgatgta acccactcgt gcacccaact      7740
gatcttcagc atcttttact ttcaccagcg tttctgggtg agcaaaaaca ggaaggcaaa      7800
atgccgcaaa aaagggaata agggcgacac ggaaatgttg aatactcata ctcttccttt      7860
ttcaatatta ttgaagcatt tatcagggtt attgtctcat gagcggatac atatttgaat      7920
gtatttagaa aaataaacaa ataggggttc cgcgcacatt tccccgaaaa gtgccacctg      7980
acgtc                                                                 7985

<210> SEQ ID NO 15
<211> LENGTH: 712
<212> TYPE: DNA
<213> ORGANISM: Artificial Sequence
<220> FEATURE:
<223> OTHER INFORMATION: CMV Promoter

<400> SEQUENCE: 15
gttgacattg attattgact agttattaat agtaatcaat tacggggtca ttagttcata       60
gcccatatat ggagttccgc gttacataac ttacggtaaa tggcccgcct ggctgaccgc      120
ccaacgaccc ccgcccattg acgtcaataa tgacgtatgt tcccatagta acgccaatag      180
ggactttcca ttgacgtcaa tgggtggagt atttacggta aactgcccac ttggcagtac      240
atcaagtgta tcatatgcca agtacgcccc ctattgacgt caatgacggt aaatggcccg      300
cctggcatta tgcccagtac atgaccttat gggactttcc tacttggcag tacatctacg      360
tattagtcat cgctattact cgagtcctta gggagcgatc cagcacgagg agaggccggg      420 aggggggcggg acgggcggg gcctctggga gagtgggttg cggggaggct ggcttttggc      480
aggaagtaac gcatttgctg gactcgagtg atgcggtttt ggcagtacat caatgggcgt      540
```

```
ggatagcggt ttgactcacg gggatttcca agtctccacc ccattgacgt caatgggagt    600
ttgttttggc accaaaatca acgggacttt ccaaaatgtc gtaacaactc cgccccattg    660
acgcaaatgg gcggtaggcg tgtacggtgg gaggtctata taagcagagc tc            712

<210> SEQ ID NO 16
<211> LENGTH: 128
<212> TYPE: DNA
<213> ORGANISM: Artificial Sequence
<220> FEATURE:
<223> OTHER INFORMATION: Part of hamster?s Aprt (Adenine
      phosphoribosyltransferase) exon2 complementary strand

<400> SEQUENCE: 16
tcgagtcctt agggagcgat ccagcacgag gagaggccgg gaggggcgg gacgggcgg      60 ggcctctggg agagtgggtt gcggggaggc tggcttttgg caggaagtaa cgcatttgct   120
ggactcga                                                             128

<210> SEQ ID NO 17
<211> LENGTH: 41
<212> TYPE: DNA
<213> ORGANISM: Artificial Sequence
<220> FEATURE:
<223> OTHER INFORMATION: Multiple Cloning Site (MCS)

<400> SEQUENCE: 17
gctagcgttt aaacttaagc ttggtaccga gctcggatcc a                        41

<210> SEQ ID NO 18
<211> LENGTH: 729
<212> TYPE: DNA
<213> ORGANISM: Artificial Sequence
<220> FEATURE:
<223> OTHER INFORMATION: Light chain of antibody GA101 (LC 1-729)

<400> SEQUENCE: 18
atggacatga gggtccctgc tcagctcctg gggctcctgc tgctctggct ctcaggtgcc    60
agatgtgaca ttgtaatgac acagacccca ctctccctgc ccgtcacccc tggagagccg   120
gcctccatct cctgcaggtc tagtaagagc ctcctgcata gtaatggaat cacctatttg   180
tactggtacc tgcagaagcc agggcagtct ccacagctcc tgatctatca gatgtctaat   240
ctggtgtccg ggtccctga caggttcagt ggcagtggat caggcacaga tttttacactg   300 aaaatcagca gagtggaggc tgaggatgtt ggggtttatt actgcgccca aaacctagag   360 ctgcccctaca ctttcggcgg agggaccaag gtggagatca aacgtaccgt ggcggcgcca   420
tctgtcttca tcttcccgcc atctgatgag cagttgaaat ctggaactgc ctctgttgtg   480
tgcctgctga ataacttcta tcccagagag gccaaagtac agtggaaggt ggataacgcc   540
ctccaatcgg gtaactccca ggagagtgtc acagagcagg acagcaagga cagcacctac   600
agcctcagca gcaccctgac gctgagcaaa gcagactacg agaaacacaa agtctacgcc   660
tgcgaagtca cccatcaggg cctgagctcg cccgtcacaa agagcttcaa caggggagag   720
tgttagtag                                                            729

<210> SEQ ID NO 19
<211> LENGTH: 20
<212> TYPE: DNA
<213> ORGANISM: Artificial Sequence
<220> FEATURE:
<223> OTHER INFORMATION: Wild type Internal Ribosome Entry Site
```

<400> SEQUENCE: 19
atgataatat ggccacaacc                                                    20

<210> SEQ ID NO 20
<211> LENGTH: 1407
<212> TYPE: DNA
<213> ORGANISM: Artificial Sequence
<220> FEATURE:
<223> OTHER INFORMATION: Heavy chain of antibody GA101 (HC 1329-2747)

<400> SEQUENCE: 20

```
atggagtttg ggctgagctg ggttttcctc gttgctcttt ttagaggtgt ccagtgtcag    60
gtgcagctgg tgcagtctgg ggctgaggtg aagaagcctg gtcctccgt gaaggtctcc    120
tgcaaggcct ctggatacgc cttctcctac tcttggatca actgggtgcg acaggcccct    180
ggacaagggc tcgagtggat gggacggatc ttccctggcg atggtgacac agactacaac    240
ggcaagttca gggcagagt caccatcacc gccgacaagt ccacgagcac agcctacatg    300
gaactgagca gcctgagatc tgaggacacg gccgtctatt actgtgcacg aaacgtgttc    360
gatggctatt ggctggtgta ctggggccag ggaccctgg tcaccgtcag cagcgctagc    420
accaagggcc catcggtctt ccccctggca ccctcctcca gagcacctc tgggggcaca    480
gcggccctgg gctgcctggt caaggactac ttccccgaac cggtgacggt gtcatggaac    540
tcaggcgccc tgaccagcgg cgtgcacacc ttcccggctg tcctacagtc ctcaggactc    600
tactccctca gcagcgtggt gaccgtgccc tccagcagct gggcaccca gacctacatc    660
tgcaacgtga atcacaagcc cagcaacacc aaggtggaca gaaagttga gcccaaatct    720
tgtgacaaaa ctcacacatg cccaccgtgc ccagcacctg aactcctggg gggaccgtca    780
gtcttcctct tccccccaaa acccaaggac accctcatga tctcccggac ccctgaggtc    840
acatgcgtgg tggtggacgt gagccacgaa gaccctgagg tcaagttcaa ctggtacgtg    900
gacggcgtgg aggtgcataa tgccaagaca agccgcggg aggagcagta caacagcacg    960
taccgtgtgg tcagcgtcct caccgtcctg caccaggact ggctgaatgg caaggagtac    1020
aagtgcaagg tctccaacaa agccctccca gccccatcg agaaaccat ctccaaagcc    1080
aaagggcagc cccgagaacc acaggtgtac accctgcccc catcccggga tgagctgacc    1140
aagaaccagg tcagcctgac ctgcctggtc aaaggcttct atcccagcga catcgccgtg    1200
gagtgggaga gcaatgggca gccggagaac aactacaaga ccacgcctcc cgtgctggac    1260
tccgacggct ccttcttcct ctacagcaag ctcaccgtgg acaagagcag gtggcagcag    1320
gggaacgtct tctcatgctc cgtgatgcat gaggctctgc acaaccacta cacgcagaag    1380
agcctctccc tgtctccggg taaatga                                         1407
```

<210> SEQ ID NO 21
<211> LENGTH: 594
<212> TYPE: DNA
<213> ORGANISM: Artificial Sequence
<220> FEATURE:
<223> OTHER INFORMATION: Attenuated Internal Ribosome Entry Site
      (IRESatt)

<400> SEQUENCE: 21

```
accggtgccc ctctccctcc ccccccccta acgttactgg ccgaagccgc ttggaataag    60
gccggtgtgc gtttgtctat atgttatttt ccaccatatt gccgtctttt ggcaatgtga    120
gggcccggaa acctggccct gtcttcttga cgagcattcc taggggtctt tcccctctcg    180
```

-continued

| | |
|---|---|
| ccaaaggaat gcaaggtctg ttgaatgtcg tgaaggaagc agttcctctg gaagcttctt | 240 |
| gaagacaaac aacgtctgta gcgacccttt gcaggcagcg gaaccccca cctggcgaca | 300 |
| ggtgcctctg cggccaaaag ccacgtgtat aagatacacc tgcaaaggcg cacaacccc | 360 |
| agtgccacgt tgtgagttgg atagttgtgg aaagagtcaa atggctctcc tcaagcgtat | 420 |
| tcaacaaggg gctgaaggat gcccagaagg tacccccattg tatgggatct gatctggggc | 480 |
| ctcggtacac atgctttaca tgtgtttagt cgaggttaaa aaaacgtcta ggccccccga | 540 |
| accacgggga cgtggttttc ctttgaaaaa cacgatgata agcttgccac aacc | 594 |

<210> SEQ ID NO 22
<211> LENGTH: 23
<212> TYPE: DNA
<213> ORGANISM: Artificial Sequence
<220> FEATURE:
<223> OTHER INFORMATION: Attenuation stretch

<400> SEQUENCE: 22

| | |
|---|---|
| ccgggagatg aggatcgttt cgc | 23 |

<210> SEQ ID NO 23
<211> LENGTH: 1122
<212> TYPE: DNA
<213> ORGANISM: Artificial Sequence
<220> FEATURE:
<223> OTHER INFORMATION: Glutamine Synthetase (GS); Wild Type Glutamine
    Synthetase from CHO cell

<400> SEQUENCE: 23

| | |
|---|---|
| atggccacct cagcaagttc ccacttgaac aaaaacatca agcaaatgta cttgtgcctg | 60 |
| ccccagggtg agaaagtcca agccatgtat atctgggttg atggtactgg agaaggactg | 120 |
| cgctgcaaaa cccgcaccct ggactgtgag cccaagtgtg tagaagagtt acctgagtgg | 180 |
| aatttgatg gctctagtac ctttcagtct gagggctcca acagtgacat gtatctcagc | 240 |
| cctgttgcca tgtttcggga cccccttccgc agagatccca acaagctggt gttctgtgaa | 300 |
| gtttcaagt acaaccggaa gcctgcagag accaatttaa ggcactcgtg taaacggata | 360 |
| atggacatgg tgagcaacca gcacccctgg tttggaatgg aacaggagta tactctgatg | 420 |
| ggaacagatg ggcacccttt tggttggcct tccaatggct ttcctgggcc ccaaggtccg | 480 |
| tattactgtg gtgtgggcgc agacaaagcc tatggcaggg atatcgtgga ggctcactac | 540 |
| cgcgcctgct tgtatgctgg ggtcaagatt acaggaacaa atgctgaggt catgcctgcc | 600 |
| cagtgggaat tccaaatagg accctgtgaa ggaatccgca tggagatca tctctgggtg | 660 |
| gcccgtttca tcttgcatcg agtatgtgaa gactttgggg taatagcaac ctttgacccc | 720 |
| aagcccattc ctgggaactg gaatggtgca ggctgccata ccaactttag caccaaggcc | 780 |
| atgcgggagg agaatggtct gaagcacatc gaggaggcca tcgagaaact aagcaagcgg | 840 |
| caccggtacc acattcgagc ctacgatccc aaggggggcc tggacaatgc ccgtcgtctg | 900 |
| actgggttcc acgaaacgtc caacatcaac gacttttctg ctggtgtcgc caatcgcagt | 960 |
| gccagcatcc gcattccccg gactgtcggc caggagaaga aggttacttt tgaagaccgc | 1020 |
| cgcccctctg ccaattgtga cccctttgca gtgacagaag ccatcgtccg cacatgcctt | 1080 |
| ctcaatgaga ctggcgacga gcccttccaa tacaaaaact aa | 1122 |

<210> SEQ ID NO 24
<211> LENGTH: 159
<212> TYPE: DNA

<213> ORGANISM: Artificial Sequence
<220> FEATURE:
<223> OTHER INFORMATION: pcDNA sequence between neo and SV40pA

<400> SEQUENCE: 24

```
ttcgaaatga ccgaccaagc gacgcccaac ctgccatcac gagatttcga ttccaccgcc      60
gccttctatg aaaggttggg cttcggaatc gttttccggg acgccggctg gatgatcctc     120
cagcgcgggg atctcatgct ggagttcttc gcccacccc                            159
```

<210> SEQ ID NO 25
<211> LENGTH: 131
<212> TYPE: DNA
<213> ORGANISM: Artificial Sequence
<220> FEATURE:
<223> OTHER INFORMATION: SV40 pA terminator sequence (SV40pA)

<400> SEQUENCE: 25

```
aacttgttta ttgcagctta taatggttac aaataaagca atagcatcac aaatttcaca      60
aataaagcat ttttttcact gcattctagt tgtggtttgt ccaaactcat caatgtatct     120
tatcatgtct g                                                          131
```

<210> SEQ ID NO 26
<211> LENGTH: 382
<212> TYPE: DNA
<213> ORGANISM: Artificial Sequence
<220> FEATURE:
<223> OTHER INFORMATION: Corresponding region with pcDNA3.1

<400> SEQUENCE: 26

```
tataccgtcg acctctagct agagcttggc gtaatcatgg tcatagctgt ttcctgtgtg      60
aaattgttat ccgctcacaa ttccacacaa catacgagcc ggaagcataa agtgtaaagc     120
ctggcgcgcc taatgagtga gctaactcac attaattgcg ttgcgctcac tgcccgcttt     180
ccagtcggga aacctgtcgt gccagctgca ttaatgaatc ggcgatcgcg cggggagagg     240
cggtttgcgt attgggcgct cttccgcttc ctcgctcact gactcgctgc gctcggtcgt     300
tcggctgcgg cgagcggtat cagctcactc aaaggcggta atacggttat ccacagaatc     360
agggggataac gcaggaaaga ac                                             382
```

<210> SEQ ID NO 27
<211> LENGTH: 671
<212> TYPE: DNA
<213> ORGANISM: Artificial Sequence
<220> FEATURE:
<223> OTHER INFORMATION: pUC origin

<400> SEQUENCE: 27

```
atgtgagcaa aaggccagca aaaggccagg aaccgtaaaa aggccgcgtt gctggcgttt      60
ttccataggc tccgcccccc tgacgagcat cacaaaaatc gacgctcaag tcagaggtgg     120
cgaaacccga caggactata agataccagg cgtttccccc tggaagctcc ctcgtgcgc     180
tctcctgttc cgaccctgcc gcttaccgga tacctgtccg cctttctccc ttcgggaagc     240
gtggcgcttt ctcatagctc acgctgtagg tatctcagtt cggtgtaggt cgttcgctcc     300
aagctgggct gtgtgcacga accccccgtt cagcccgacc gctgcgcctt atccggtaac     360
tatcgtcttg agtccaaccc ggtaagacac gacttatcgc cactggcagc agccactggt     420
aacaggatta gcagagcgag gtatgtaggc ggtgctacag agttcttgaa gtggtggcct     480
aactacggct acactagaag aacagtattt ggtatctgcg ctctgctgaa gccagttacc     540
```

```
ttcggaaaaa gagttggtag ctcttgatcc ggcaaacaaa ccaccgctgg tagcggtttt      600
tttgtttgca agcagcagat tacgcgcaga aaaaaaggat ctcaagaaga tcctttgatc      660
ttttctacgg g                                                          671
```

<210> SEQ ID NO 28
<211> LENGTH: 144
<212> TYPE: DNA
<213> ORGANISM: Artificial Sequence
<220> FEATURE:
<223> OTHER INFORMATION: Corresponding region with pcDNA3.1

<400> SEQUENCE: 28

```
gtctgacgct cagtggaacg aaaactcacg ttaagggatt ttggtcatga gattatcaaa       60
aaggatcttc acctagatcc ttttaaatta aaaatgaagt tttaaatcaa tctaaagtat      120
atatgagtaa acttggtctg acag                                             144
```

<210> SEQ ID NO 29
<211> LENGTH: 861
<212> TYPE: DNA
<213> ORGANISM: Artificial Sequence
<220> FEATURE:
<223> OTHER INFORMATION: Ampicillin (Amp) resistance gene on
      complementary strand

<400> SEQUENCE: 29

```
ttaccaatgc ttaatcagtg aggcacctat ctcagcgatc tgtctatttc gttcatccat       60
agttgcctga ctccccgtcg tgtagataac tacgatacgg gagggcttac catctggccc      120
cagtgctgca atgataccgc gagacccacg ctcaccggct ccagatttat cagcaataaa      180
ccagccagcc ggaagggccg agcgcagaag tggtcctgca actttatccg cctccatcca      240
gtctattaat tgttgccggg aagctagagt aagtagttcg ccagttaata gtttgcgcaa      300
cgttgttgcc attgctacag gcatcgtggt gtcacgctcg tcgtttggta tggcttcatt      360
cagctccggt tcccaacgat caaggcgagt tacatgatcc cccatgttgt gcaaaaaagc      420
ggttagctcc ttcggtcctc cgatcgttgt cagaagtaag ttggccgcag tgttatcact      480
catggttatg gcagcactgc ataattctct tactgtcatg ccatccgtaa gatgcttttc      540
tgtgactggt gagtactcaa ccaagtcatt ctgagaatag tgtatgcggc gaccgagttg      600
ctcttgcccg gcgtcaatac gggataatac cgcgccacat agcagaactt taaaagtgct      660
catcattgga aaacgttctt cggggcgaaa actctcaagg atcttaccgc tgttgagatc      720
cagttcgatg taacccactc gtgcacccaa ctgatcttca gcatctttta ctttcaccag      780
cgtttctggg tgagcaaaaa caggaaggca aaatgccgca aaaaagggaa taagggcgac      840
acggaaatgt tgaatactca t                                               861
```

<210> SEQ ID NO 30
<211> LENGTH: 136
<212> TYPE: DNA
<213> ORGANISM: Artificial Sequence
<220> FEATURE:
<223> OTHER INFORMATION: beta-Lactamase (bla) promoter

<400> SEQUENCE: 30

```
actcttcctt tttcaatatt attgaagcat ttatcagggt tattgtctca tgagcggata       60
catatttgaa tgtatttaga aaaataaaca ataggggtt ccgcgcacat ttccccgaaa       120
agtgccacct gacgtc                                                     136
```

<210> SEQ ID NO 31
<211> LENGTH: 57
<212> TYPE: DNA
<213> ORGANISM: Artificial Sequence
<220> FEATURE:
<223> OTHER INFORMATION: primer GSsmaUP

<400> SEQUENCE: 31
gtgtgacccg ggagatgagg atcgtttcgc atggccacct cagcaagttc ccacttg    57

<210> SEQ ID NO 32
<211> LENGTH: 42
<212> TYPE: DNA
<213> ORGANISM: Artificial Sequence
<220> FEATURE:
<223> OTHER INFORMATION: primer GSBstBILP

<400> SEQUENCE: 32
gaattcttcg aattagtttt tgtattcgaa gggctcgtcg cc    42

<210> SEQ ID NO 33
<211> LENGTH: 96
<212> TYPE: DNA
<213> ORGANISM: Artificial Sequence
<220> FEATURE:
<223> OTHER INFORMATION: primer GSSMASV4UP

<400> SEQUENCE: 33
gtgctcccgg gagcttgtat atccattttc ggatctgatc aagagacagg atgaggatcg    60
gccaccatgg ccacctcagc aagttcccac ttgaac    96

<210> SEQ ID NO 34
<211> LENGTH: 54
<212> TYPE: DNA
<213> ORGANISM: Artificial Sequence
<220> FEATURE:
<223> OTHER INFORMATION: primer GSBSTBISV4LP

<400> SEQUENCE: 34
ggtcatttcg aaccccagag tcccgcttag tttttgtatt ggaagggctc gtcg    54

<210> SEQ ID NO 35
<211> LENGTH: 36
<212> TYPE: DNA
<213> ORGANISM: Artificial Sequence
<220> FEATURE:
<223> OTHER INFORMATION: primer R324CFP

<400> SEQUENCE: 35
cgcagtgcca gcatctgcat tccccggact gtcggc    36

<210> SEQ ID NO 36
<211> LENGTH: 36
<212> TYPE: DNA
<213> ORGANISM: Artificial Sequence
<220> FEATURE:
<223> OTHER INFORMATION: primer R324CLP

<400> SEQUENCE: 36
gccgacagtc cggggaatgc agatgctggc actgcg    36

<210> SEQ ID NO 37
<211> LENGTH: 39
<212> TYPE: DNA

```
<213> ORGANISM: Artificial Sequence
<220> FEATURE:
<223> OTHER INFORMATION: primer R341CFP

<400> SEQUENCE: 37
ggttactttg aagaccgctg cccctctgcc aattgtgac                              39

<210> SEQ ID NO 38
<211> LENGTH: 39
<212> TYPE: DNA
<213> ORGANISM: Artificial Sequence
<220> FEATURE:
<223> OTHER INFORMATION: primer R341CLP

<400> SEQUENCE: 38
gtcacaattg gcagaggggc agcggtcttc aaagtaacc                              39

<210> SEQ ID NO 39
<211> LENGTH: 33
<212> TYPE: DNA
<213> ORGANISM: Artificial Sequence
<220> FEATURE:
<223> OTHER INFORMATION: primer R324AUP

<400> SEQUENCE: 39
cgcagtgcca gcatcgccat tccccggact gtc                                   33

<210> SEQ ID NO 40
<211> LENGTH: 33
<212> TYPE: DNA
<213> ORGANISM: Artificial Sequence
<220> FEATURE:
<223> OTHER INFORMATION: primer R324ALP

<400> SEQUENCE: 40
gacagtccgg ggaatggcga tgctggcact gcg                                   33

<210> SEQ ID NO 41
<211> LENGTH: 33
<212> TYPE: DNA
<213> ORGANISM: Artificial Sequence
<220> FEATURE:
<223> OTHER INFORMATION: primer R341AUP

<400> SEQUENCE: 41
tactttgaag accgcgcccc ctctgccaat tgt                                   33

<210> SEQ ID NO 42
<211> LENGTH: 33
<212> TYPE: DNA
<213> ORGANISM: Artificial Sequence
<220> FEATURE:
<223> OTHER INFORMATION: primer R341ALP

<400> SEQUENCE: 42
acaattggca gagggggcgc ggtcttcaaa gta                                   33

<210> SEQ ID NO 43
<211> LENGTH: 36
<212> TYPE: DNA
<213> ORGANISM: Artificial Sequence
<220> FEATURE:
<223> OTHER INFORMATION: primer GSM1 UP

<400> SEQUENCE: 43
cctgagtgga attttgctgg ctctagtacc tttcag                                36
```

<210> SEQ ID NO 44
<211> LENGTH: 36
<212> TYPE: DNA
<213> ORGANISM: Artificial Sequence
<220> FEATURE:
<223> OTHER INFORMATION: primer GSM1 LP

<400> SEQUENCE: 44
ctgaaaggta ctagtgccag caaaattcca ctcagg                36

<210> SEQ ID NO 45
<211> LENGTH: 39
<212> TYPE: DNA
<213> ORGANISM: Artificial Sequence
<220> FEATURE:
<223> OTHER INFORMATION: primer GSM2 UP

<400> SEQUENCE: 45
tggaattttg atggctctgc tacctttcag tctgagggc             39

<210> SEQ ID NO 46
<211> LENGTH: 39
<212> TYPE: DNA
<213> ORGANISM: Artificial Sequence
<220> FEATURE:
<223> OTHER INFORMATION: primer GSM2 LP

<400> SEQUENCE: 46
gccctcagac tgaaaggtag cagagccatc aaaattcca             39

<210> SEQ ID NO 47
<211> LENGTH: 36
<212> TYPE: DNA
<213> ORGANISM: Artificial Sequence
<220> FEATURE:
<223> OTHER INFORMATION: primer GSM4 UP

<400> SEQUENCE: 47
cacccctggt ttggaatggc acaggagtat actctg                36

<210> SEQ ID NO 48
<211> LENGTH: 36
<212> TYPE: DNA
<213> ORGANISM: Artificial Sequence
<220> FEATURE:
<223> OTHER INFORMATION: primer GSM4 LP

<400> SEQUENCE: 48
cagagtatac tcctgtgcca ttccaaacca ggggtg                36

<210> SEQ ID NO 49
<211> LENGTH: 39
<212> TYPE: DNA
<213> ORGANISM: Artificial Sequence
<220> FEATURE:
<223> OTHER INFORMATION: primer GSM5 UP

<400> SEQUENCE: 49
tggtttggaa tggaacaggc gtatactctg atgggaaca             39

<210> SEQ ID NO 50
<211> LENGTH: 39
<212> TYPE: DNA
<213> ORGANISM: Artificial Sequence
<220> FEATURE:

```
<223> OTHER INFORMATION: primer GSM5 LP

<400> SEQUENCE: 50
tgttcccatc agagtatacg cctgttccat tccaaacca                              39

<210> SEQ ID NO 51
<211> LENGTH: 36
<212> TYPE: DNA
<213> ORGANISM: Artificial Sequence
<220> FEATURE:
<223> OTHER INFORMATION: primer GSM6 UP

<400> SEQUENCE: 51
ccccaaggtc cgtatgcctg tggtgtgggc gcagac                                 36

<210> SEQ ID NO 52
<211> LENGTH: 36
<212> TYPE: DNA
<213> ORGANISM: Artificial Sequence
<220> FEATURE:
<223> OTHER INFORMATION: primer GSM6 LP

<400> SEQUENCE: 52
gtctgcgccc acaccacagg catacggacc ttgggg                                 36

<210> SEQ ID NO 53
<211> LENGTH: 33
<212> TYPE: DNA
<213> ORGANISM: Artificial Sequence
<220> FEATURE:
<223> OTHER INFORMATION: primer GSM8 UP

<400> SEQUENCE: 53
ggggtcaaga ttacagcaac aaatgctgag gtc                                    33

<210> SEQ ID NO 54
<211> LENGTH: 33
<212> TYPE: DNA
<213> ORGANISM: Artificial Sequence
<220> FEATURE:
<223> OTHER INFORMATION: primer GSM8 LP

<400> SEQUENCE: 54
gacctcagca tttgttgctg taatcttgac ccc                                    33

<210> SEQ ID NO 55
<211> LENGTH: 33
<212> TYPE: DNA
<213> ORGANISM: Artificial Sequence
<220> FEATURE:
<223> OTHER INFORMATION: primer GSM9 UP

<400> SEQUENCE: 55
acaggaacaa atgctgcggt catgcctgcc cag                                    33

<210> SEQ ID NO 56
<211> LENGTH: 33
<212> TYPE: DNA
<213> ORGANISM: Artificial Sequence
<220> FEATURE:
<223> OTHER INFORMATION: primer GSM9 LP

<400> SEQUENCE: 56
ctgggcaggc atgaccgcag catttgttcc tgt                                    33
```

```
<210> SEQ ID NO 57
<211> LENGTH: 33
<212> TYPE: DNA
<213> ORGANISM: Artificial Sequence
<220> FEATURE:
<223> OTHER INFORMATION: primer GSM10 UP

<400> SEQUENCE: 57
atgcctgccc agtgggcatt ccaaatagga ccc                             33

<210> SEQ ID NO 58
<211> LENGTH: 33
<212> TYPE: DNA
<213> ORGANISM: Artificial Sequence
<220> FEATURE:
<223> OTHER INFORMATION: primer GSM10 LP

<400> SEQUENCE: 58
gggtcctatt tggaatgccc actgggcagg cat                             33

<210> SEQ ID NO 59
<211> LENGTH: 36
<212> TYPE: DNA
<213> ORGANISM: Artificial Sequence
<220> FEATURE:
<223> OTHER INFORMATION: primer GSM12 UP

<400> SEQUENCE: 59
attcctggga actgggcagg tgcaggctgc catacc                          36

<210> SEQ ID NO 60
<211> LENGTH: 36
<212> TYPE: DNA
<213> ORGANISM: Artificial Sequence
<220> FEATURE:
<223> OTHER INFORMATION: primer GSM12 LP

<400> SEQUENCE: 60
ggtatggcag cctgcacctg cccagttccc aggaat                          36

<210> SEQ ID NO 61
<211> LENGTH: 33
<212> TYPE: DNA
<213> ORGANISM: Artificial Sequence
<220> FEATURE:
<223> OTHER INFORMATION: primer GSM13 UP

<400> SEQUENCE: 61
cctgggaact ggaatgctgc aggctgccat acc                             33

<210> SEQ ID NO 62
<211> LENGTH: 33
<212> TYPE: DNA
<213> ORGANISM: Artificial Sequence
<220> FEATURE:
<223> OTHER INFORMATION: primer GSM13 LP

<400> SEQUENCE: 62
ggtatggcag cctgcagcat tccagttccc agg                             33

<210> SEQ ID NO 63
<211> LENGTH: 33
<212> TYPE: DNA
<213> ORGANISM: Artificial Sequence
<220> FEATURE:
<223> OTHER INFORMATION: primer GSM14 UP
```

```
<400> SEQUENCE: 63
aatggtgcag gctgcgcaac caactttagc acc                                    33

<210> SEQ ID NO 64
<211> LENGTH: 33
<212> TYPE: DNA
<213> ORGANISM: Artificial Sequence
<220> FEATURE:
<223> OTHER INFORMATION: primer GSM14 LP

<400> SEQUENCE: 64
ggtgctaaag ttggttgcgc agcctgcacc att                                    33

<210> SEQ ID NO 65
<211> LENGTH: 33
<212> TYPE: DNA
<213> ORGANISM: Artificial Sequence
<220> FEATURE:
<223> OTHER INFORMATION: primer GSM15 UP

<400> SEQUENCE: 65
gcaggctgcc ataccgcatt tagcaccaag gcc                                    33

<210> SEQ ID NO 66
<211> LENGTH: 33
<212> TYPE: DNA
<213> ORGANISM: Artificial Sequence
<220> FEATURE:
<223> OTHER INFORMATION: primer GSM15 LP

<400> SEQUENCE: 66
ggccttggtg ctaaatgcgg tatggcagcc tgc                                    33

<210> SEQ ID NO 67
<211> LENGTH: 36
<212> TYPE: DNA
<213> ORGANISM: Artificial Sequence
<220> FEATURE:
<223> OTHER INFORMATION: primer GSM16 UP

<400> SEQUENCE: 67
ggctgccata ccaactttgc aaccaaggcc atgcgg                                 36

<210> SEQ ID NO 68
<211> LENGTH: 36
<212> TYPE: DNA
<213> ORGANISM: Artificial Sequence
<220> FEATURE:
<223> OTHER INFORMATION: primer GSM16 LP

<400> SEQUENCE: 68
ccgcatggcc ttggttgcaa agttggtatg gcagcc                                 36

<210> SEQ ID NO 69
<211> LENGTH: 33
<212> TYPE: DNA
<213> ORGANISM: Artificial Sequence
<220> FEATURE:
<223> OTHER INFORMATION: primer GSM17 UP

<400> SEQUENCE: 69
agcaccaagg ccatggcgga ggagaatggt ctg                                    33

<210> SEQ ID NO 70
<211> LENGTH: 33
```

```
<212> TYPE: DNA
<213> ORGANISM: Artificial Sequence
<220> FEATURE:
<223> OTHER INFORMATION: primer GSM17 LP

<400> SEQUENCE: 70
cagaccattc tcctccgcca tggccttggt gct                              33

<210> SEQ ID NO 71
<211> LENGTH: 33
<212> TYPE: DNA
<213> ORGANISM: Artificial Sequence
<220> FEATURE:
<223> OTHER INFORMATION: primer GSM18 UP

<400> SEQUENCE: 71
ctggacaatg cccgtgctct gactgggttc cac                              33

<210> SEQ ID NO 72
<211> LENGTH: 33
<212> TYPE: DNA
<213> ORGANISM: Artificial Sequence
<220> FEATURE:
<223> OTHER INFORMATION: primer GSM18 LP

<400> SEQUENCE: 72
gtggaaccca gtcagagcac gggcattgtc cag                              33

<210> SEQ ID NO 73
<211> LENGTH: 33
<212> TYPE: DNA
<213> ORGANISM: Artificial Sequence
<220> FEATURE:
<223> OTHER INFORMATION: primer GSM19 UP

<400> SEQUENCE: 73
ctgactgggt tccacgcaac gtccaacatc aac                              33

<210> SEQ ID NO 74
<211> LENGTH: 33
<212> TYPE: DNA
<213> ORGANISM: Artificial Sequence
<220> FEATURE:
<223> OTHER INFORMATION: primer GSM19 LP

<400> SEQUENCE: 74
gttgatgttg gacgttgcgt ggaacccagt cag                              33

<210> SEQ ID NO 75
<211> LENGTH: 33
<212> TYPE: DNA
<213> ORGANISM: Artificial Sequence
<220> FEATURE:
<223> OTHER INFORMATION: primer GSM20 UP

<400> SEQUENCE: 75
gctggtgtcg ccaatgccag tgccagcatc cgc                              33

<210> SEQ ID NO 76
<211> LENGTH: 33
<212> TYPE: DNA
<213> ORGANISM: Artificial Sequence
<220> FEATURE:
<223> OTHER INFORMATION: primer GSM20 LP

<400> SEQUENCE: 76
```

```
gcggatgctg gcactggcat tggcgacacc agc                                33
```

```
<210> SEQ ID NO 77
<211> LENGTH: 33
<212> TYPE: DNA
<213> ORGANISM: Artificial Sequence
<220> FEATURE:
<223> OTHER INFORMATION: primer GSM21 UP

<400> SEQUENCE: 77
caggagaaga aaggtgcttt tgaagaccgc cgc                                33
```

```
<210> SEQ ID NO 78
<211> LENGTH: 33
<212> TYPE: DNA
<213> ORGANISM: Artificial Sequence
<220> FEATURE:
<223> OTHER INFORMATION: primer GSM21 LP

<400> SEQUENCE: 78
gcggcggtct tcaaaagcac ctttcttctc ctg                                33
```

```
<210> SEQ ID NO 79
<211> LENGTH: 36
<212> TYPE: DNA
<213> ORGANISM: Artificial Sequence
<220> FEATURE:
<223> OTHER INFORMATION: primer GSM22 UP

<400> SEQUENCE: 79
aagaaaggtt actttgcaga ccgccgcccc tctgcc                             36
```

```
<210> SEQ ID NO 80
<211> LENGTH: 36
<212> TYPE: DNA
<213> ORGANISM: Artificial Sequence
<220> FEATURE:
<223> OTHER INFORMATION: primer GSM22 LP

<400> SEQUENCE: 80
ggcagagggg cggcggtctg caaagtaacc tttctt                             36
```

```
<210> SEQ ID NO 81
<211> LENGTH: 33
<212> TYPE: DNA
<213> ORGANISM: Artificial Sequence
<220> FEATURE:
<223> OTHER INFORMATION: primer GSM23 UP

<400> SEQUENCE: 81
actgtcggcc aggaggcgaa aggttacttt gaa                                33
```

```
<210> SEQ ID NO 82
<211> LENGTH: 33
<212> TYPE: DNA
<213> ORGANISM: Artificial Sequence
<220> FEATURE:
<223> OTHER INFORMATION: primer GSM23 LP

<400> SEQUENCE: 82
ttcaaagtaa cctttcgcct cctggccgac agt                                33
```

```
<210> SEQ ID NO 83
<211> LENGTH: 33
<212> TYPE: DNA
<213> ORGANISM: Artificial Sequence
```

```
<220> FEATURE:
<223> OTHER INFORMATION: primer GSM24 UP

<400> SEQUENCE: 83
ggttactttg aagacgcccg cccctctgcc aat                                 33

<210> SEQ ID NO 84
<211> LENGTH: 33
<212> TYPE: DNA
<213> ORGANISM: Artificial Sequence
<220> FEATURE:
<223> OTHER INFORMATION: primer GSM24 LP

<400> SEQUENCE: 84
attggcagag gggcgggcgt cttcaaagta acc                                 33

<210> SEQ ID NO 85
<211> LENGTH: 7985
<212> TYPE: DNA
<213> ORGANISM: Artificial Sequence
<220> FEATURE:
<223> OTHER INFORMATION: Tricistronic GA101 GS R324C

<400> SEQUENCE: 85
gacggatcgg gagatctccc gatcccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac tcgagtcctt agggagcgat ccagcacgag gagaggccgg gaggggcgg   660 gacggggcgg ggcctctggg agagtgggtt gcgggaggc tggcttttgg caggaagtaa   720
cgcatttgct ggactcgagt gatgcggttt tgcagtaca tcaatgggcg tggatagcgg   780
tttgactcac ggggatttcc aagtctccac cccattgacg tcaatgggag tttgttttgg   840
caccaaaatc aacgggactt tccaaaatgt cgtaacaact ccgccccatt gacgcaaatg   900
ggcggtaggc gtgtacggtg gaaggtctat ataagcagag ctctctggct agcgtttaaa   960
cttaagcttg gtaccgagct cggatccaga attcgccaca atggacatga gggtccctgc  1020
tcagctcctg gggctcctgc tgctctggct ctcaggtgcc agatgtgaca ttgtaatgac  1080
acagacccca ctctccctgc ccgtcacccc tggagagccg gcctccatct cctgcaggtc  1140
tagtaagagc ctcctgcata gtaatggaat cacctatttg tactggtacc tgcagaagcc  1200
agggcagtct ccacagctcc tgatctatca gatgtctaat ctggtgtccg ggtccctga  1260 caggttcagt ggcagtggat caggcacaga ttttacactg aaaatcagca gagtggaggc  1320
tgaggatgtt ggggtttatt actgcgccca aaacctagag ctgccctaca ctttcggcgg  1380
agggaccaag gtggagatca aacgtaccgt ggcggcgcca tctgtcttca tcttcccgcc  1440
atctgatgag cagttgaaat ctggaactgc ctctgttgtg tgcctgctga ataacttcta  1500
```

```
tcccagagag gccaaagtac agtggaaggt ggataacgcc ctccaatcgg gtaactccca    1560
ggagagtgtc acagagcagg acagcaagga cagcacctac agcctcagca gcaccctgac    1620
gctgagcaaa gcagactacg agaaacacaa agtctacgcc tgcgaagtca cccatcaggg    1680
cctgagctcg cccgtcacaa agagcttcaa caggggagag tgttagtagg atatcgtcta    1740 gaccccctctc cctccccccc ccctaacgtt actggccgaa gccgcttgga ataaggccgg    1800
tgtgcgtttg tctatatgtt attttccacc atattgccgt cttttggcaa tgtgagggcc    1860
cggaaacctg gccctgtctt cttgacgagc attcctaggg gtctttcccc tctcgccaaa    1920
ggaatgcaag gtctgttgaa tgtcgtgaag gaagcagttc ctctggaagc ttcttgaaga    1980
caaacaacgt ctgtagcgac cctttgcagg cagcggaacc ccccacctgg cgacaggtgc    2040
ctctgcggcc aaaagccacg tgtataagat acacctgcaa aggcggcaca accccagtgc    2100
cacgttgtga gttggatagt tgtggaaaga gtcaaatggc tctcctcaag cgtattcaac    2160
aaggggctga aggatgccca gaaggtaccc cattgtatgg gatctgatct ggggcctcgg    2220
tacacatgct ttacatgtgt ttagtcgagg ttaaaaaaac gtctaggccc cccgaaccac    2280
ggggacgtgg ttttcctttg aaaaacacga tgataatatg ccacaaccca tggagtttgg    2340
gctgagctgg gttttcctcg ttgctctttt tagaggtgtc cagtgtcagg tgcagctggt    2400
gcagtctggg gctgaggtga agaagcctgg gtcctccgtg aaggtctcct gcaaggcctc    2460
tggatacgcc ttctcctact cttggatcaa ctgggtgcga caggcccctg gacaagggct    2520
cgagtggatg ggacggatct tccctggcga tggtgacaca gactacaacg gcaagttcaa    2580
gggcagagtc accatcaccg ccgacaagtc cacgagcaca gcctacatgg aactgagcag    2640
cctgagatct gaggacacgg ccgtctatta ctgtgcacga aacgtgttcg atggctattg    2700
gctggtgtac tggggccagg ggaccctggt caccgtcagc agcgctagca ccaagggccc    2760
atcggtcttc cccctggcac cctcctccaa gagcacctct ggggggcacag cggccctggg    2820 ctgcctggtc aaggactact ccccgaacc ggtgacggtg tcatggaact caggcgccct    2880
gaccagcggc gtgcacacct tcccggctgt cctacagtcc tcaggactct actccctcag    2940
cagcgtggtg accgtgccct ccagcagctt gggcacccag acctacatct gcaacgtgaa    3000
tcacaagccc agcaacacca aggtggacaa gaaagttgag cccaaatctt gtgacaaaac    3060
tcacacatgc ccaccgtgcc cagcacctga actcctgggg ggaccgtcag tcttcctctt    3120
ccccccaaaa cccaaggaca ccctcatgat ctcccggacc cctgaggtca catgcgtggt    3180
ggtggacgtg agccacgaag accctgaggt caagttcaac tggtacgtgg acggcgtgga    3240
ggtgcataat gccaagacaa agccgcggga ggagcagtac aacagcacgt accgtgtggt    3300
cagcgtcctc accgtcctgc accaggactg gctgaatggc aaggagtaca agtgcaaggt    3360
ctccaacaaa gccctcccag cccccatcga gaaaaccatc tccaaagcca aagggcagcc    3420
ccgagaacca caggtgtaca ccctgccccc atcccgggat gagctgacca agaaccaggt    3480
cagcctgacc tgcctggtca aaggcttcta tcccagcgac atcgccgtgg agtgggagag    3540
caatgggcag ccggagaaca actacaagac cacgcctccc gtgctggact ccgacggctc    3600
cttcttcctc tacagcaagc tcaccgtgga caagagcagg tggcagcagg gaacgtctt    3660 ctcatgctcc gtgatgcatg aggctctgca caaccactac acgcagaaga gcctctccct    3720
gtctccgggt aaatgaatcg atgcctgcag gtgccggcc acaccggtgc cctctccct    3780 cccccccccc taacgttact ggccgaagcc gcttggaata aggccggtgt gcgtttgtct    3840
atatgttatt ttccaccata ttgccgtctt ttggcaatgt gagggcccgg aaacctggcc    3900
```

```
ctgtcttctt gacgagcatt cctaggggtc tttcccctct cgccaaagga atgcaaggtc    3960
tgttgaatgt cgtgaaggaa gcagttcctc tggaagcttc ttgaagacaa acaacgtctg    4020
tagcgaccct ttgcaggcag cggaaccccc cacctggcga caggtgcctc tgcggccaaa    4080
agccacgtgt ataagataca cctgcaaagg cggcacaacc ccagtgccac gttgtgagtt    4140
ggatagttgt ggaaagagtc aaatggctct cctcaagcgt attcaacaag gggctgaagg    4200
atgcccagaa ggtaccccat tgtatgggat ctgatctggg gcctcggtac acatgcttta    4260
catgtgttta gtcgaggtta aaaaaacgtc taggcccccc gaaccacggg gacgtggttt    4320
tcctttgaaa aacacgatga taagcttgcc acaaccccgg gagatgagga tcgtttcgca    4380
tggccacctc agcaagttcc cacttgaaca aaaacatcaa gcaaatgtac ttgtgcctgc    4440
cccagggtga gaaagtccaa gccatgtata tctgggttga tggtactgga gaaggactgc    4500
gctgcaaaac ccgcaccctg gactgtgagc ccaagtgtgt agaagagtta cctgagtgga    4560
attttgatgg ctctagtacc tttcagtctg agggctccaa cagtgacatg tatctcagcc    4620
ctgttgccat gtttcgggac cccttccgca gagatcccaa caagctggtg ttctgtgaag    4680
ttttcaagta caaccggaag cctgcagaga ccaatttaag gcactcgtgt aaacggataa    4740
tggacatggt gagcaaccag caccctggt ttggaatgga acaggagtat actctgatgg    4800
gaacagatgg gcacccttt ggttggcctt ccaatggctt tcctgggccc caaggtccgt    4860
attactgtgg tgtgggcgca gacaaagcct atggcaggga tatcgtggag gctcactacc    4920
gcgcctgctt gtatgctggg gtcaagatta caggaacaaa tgctgaggtc atgcctgccc    4980
agtgggaatt ccaaatagga ccctgtgaag gaatccgcat gggagatcat ctctgggtgg    5040
cccgtttcat cttgcatcga gtatgtgaag actttggggt aatagcaacc tttgacccca    5100
agcccattcc tgggaactgg aatggtgcag gctgccatac caactttagc accaaggcca    5160
tgcgggagga gaatggtctg aagcacatcg aggaggccat cgagaaacta gcaagcggc    5220 accggtacca cattcgagcc tacgatccca aggggggcct ggacaatgcc cgtcgtctga    5280
ctgggttcca cgaaacgtcc aacatcaacg acttttctgc tggtgtcgcc aatcgcagtg    5340
ccagcatctg cattccccgg actgtcggcc aggagaagaa aggttacttt gaagaccgcc    5400 gccctctgc caattgtgac ccctttgcag tgacagaagc catcgtccgc acatgccttc    5460
tcaatgagac tggcgacgag cccttccaat acaaaaacta attcgaaatg accgaccaag    5520
cgacgcccaa cctgccatca cgagatttcg attccaccgc cgccttctat gaaaggttgg    5580
gcttcggaat cgttttccgg gacgccggct ggatgatcct ccagcgcggg gatctcatgc    5640
tggagttctt cgcccacccc aacttgttta ttgcagctta taatggttac aaataaagca    5700
atagcatcac aaatttcaca aataaagcat ttttttcact gcattctagt tgtggtttgt    5760
ccaaactcat caatgtatct tatcatgtct gtataccgtc gacctctagc tagagcttgg    5820
cgtaatcatg gtcatagctg tttcctgtgt gaaattgtta tccgctcaca attccacaca    5880
acatacgagc cggaagcata aagtgtaaag cctggcgcgc taatgagtg agctaactca    5940 cattaattgc gttgcgctca ctgcccgctt tccagtcggg aaacctgtcg tgccagctgc    6000
attaatgaat cggcgatcgc gcggggagag cggtttgcg tattgggcgc tcttccgctt    6060
cctcgctcac tgactcgctg cgctcggtcg ttcggctgcg gcgagcggta tcagctcact    6120
caaaggcggt aatacggtta tccacagaat caggggataa cgcaggaaag aacatgtgag    6180
caaaaggcca gcaaaaggcc aggaaccgta aaaaggccgc gttgctggcg ttttccata    6240
```

```
ggctccgccc ccctgacgag catcacaaaa atcgacgctc aagtcagagg tggcgaaacc      6300
cgacaggact ataaagatac caggcgtttc ccctggaag ctccctcgtg cgctctcctg       6360
ttccgaccct gccgcttacc ggatacctgt ccgcctttct cccttcggga agcgtggcgc      6420
tttctcatag ctcacgctgt aggtatctca gttcggtgta ggtcgttcgc tccaagctgg      6480
gctgtgtgca cgaaccccc gttcagcccg accgctgcgc cttatccggt aactatcgtc       6540
ttgagtccaa cccggtaaga cacgacttat cgccactggc agcagccact ggtaacagga      6600
ttagcagagc gaggtatgta ggcggtgcta cagagttctt gaagtggtgg cctaactacg      6660
gctacactag aagaacagta tttggtatct gcgctctgct gaagccagtt accttcggaa      6720
aaagagttgg tagctcttga tccggcaaac aaaccaccgc tggtagcggt ttttttgttt      6780
gcaagcagca gattacgcgc agaaaaaaag gatctcaaga agatcctttg atcttttcta      6840
cggggtctga cgctcagtgg aacgaaaact cacgttaagg gattttggtc atgagattat      6900
caaaaaggat cttcacctag atccttttaa attaaaaatg aagttttaaa tcaatctaaa      6960
gtatatatga gtaaacttgg tctgacagtt accaatgctt aatcagtgag gcacctatct      7020
cagcgatctg tctatttcgt tcatccatag ttgcctgact ccccgtcgtg tagataacta      7080
cgatacggga gggcttacca tctggcccca gtgctgcaat gataccgcga gacccacgct      7140
caccggctcc agatttatca gcaataaacc agccagccgg aagggccgag cgcagaagtg      7200
gtcctgcaac tttatccgcc tccatccagt ctattaattg ttgccgggaa gctagagtaa      7260
gtagttcgcc agttaatagt ttgcgcaacg ttgttgccat tgctacaggc atcgtggtgt      7320
cacgctcgtc gtttggtatg gcttcattca gctccggttc ccaacgatca aggcgagtta      7380
catgatcccc catgttgtgc aaaaaagcgg ttagctcctt cggtcctccg atcgttgtca      7440
gaagtaagtt ggccgcagtg ttatcactca tggttatggc agcactgcat aattctctta      7500
ctgtcatgcc atccgtaaga tgcttttctg tgactggtga gtactcaacc aagtcattct      7560
gagaatagtg tatgcggcga ccgagttgct cttgcccggc gtcaatacgg gataataccg      7620
cgccacatag cagaacttta aaagtgctca tcattggaaa acgttcttcg ggcgaaaac      7680 tctcaaggat cttaccgctg ttgagatcca gttcgatgta acccactcgt gcacccaact      7740
gatcttcagc atcttttact ttcaccagcg tttctgggtg agcaaaaaca ggaaggcaaa      7800
atgccgcaaa aaagggaata agggcgacac ggaaatgttg aatactcata ctcttccttt      7860
ttcaatatta ttgaagcatt tatcagggtt attgtctcat gagcggatac atatttgaat      7920
gtatttagaa aaataaacaa ataggggttc cgcgcacatt tccccgaaaa gtgccacctg      7980
acgtc                                                                 7985

<210> SEQ ID NO 86
<211> LENGTH: 128
<212> TYPE: DNA
<213> ORGANISM: Artificial Sequence
<220> FEATURE:
<223> OTHER INFORMATION: Part of hamster?s Aprt (Adenine
      phosphoribosyltransferase) exon2 complementary strand

<400> SEQUENCE: 86
tcgagtcctt agggagcgat ccagcacgag gagaggccgg gaggggcgg gacggggcgg        60 ggcctctggg agagtgggtt gcggggaggc tggcttttgg caggaagtaa cgcatttgct      120
ggactcga                                                              128

<210> SEQ ID NO 87
```

<211> LENGTH: 205
<212> TYPE: DNA
<213> ORGANISM: Artificial Sequence
<220> FEATURE:
<223> OTHER INFORMATION: Second portion of CMV promoter

<400> SEQUENCE: 87

```
gtgatgcggt tttggcagta catcaatggg cgtggatagc ggtttgactc acggggattt      60
ccaagtctcc acccccattga cgtcaatggg agtttgtttt ggcaccaaaa tcaacgggac   120
tttccaaaat gtcgtaacaa ctccgcccca ttgacgcaaa tgggcggtag cgtgtacgg    180
tgggaggtct atataagcag agctc                                         205
```

<210> SEQ ID NO 88
<211> LENGTH: 41
<212> TYPE: DNA
<213> ORGANISM: Artificial Sequence
<220> FEATURE:
<223> OTHER INFORMATION: Multiple Cloning Site (MCS)

<400> SEQUENCE: 88

```
gctagcgttt aaacttaagc ttggtaccga gctcggatcc a                         41
```

<210> SEQ ID NO 89
<211> LENGTH: 729
<212> TYPE: DNA
<213> ORGANISM: Artificial Sequence
<220> FEATURE:
<223> OTHER INFORMATION: Light chain of antibody GA101 (LC 1-729)

<400> SEQUENCE: 89

```
atggacatga gggtccctgc tcagctcctg gggctcctgc tgctctggct ctcaggtgcc      60
agatgtgaca ttgtaatgac acagacccca ctctccctgc ccgtcacccc tggagagccg   120
gcctccatct cctgcaggtc tagtaagagc ctcctgcata gtaatggaat cacctatttg   180
tactggtacc tgcagaagcc agggcagtct ccacagctcc tgatctatca gatgtctaat   240
ctggtgtccg ggtccctga caggttcagt ggcagtggat caggcacaga ttttacactg    300
aaaatcagca gagtggaggc tgaggatgtt ggggtttatt actgcgccca aaacctagag   360
ctgcccctaca ctttcggcgg agggaccaag gtggagatca aacgtaccgt ggcggcgcca  420
tctgtcttca tcttcccgcc atctgatgag cagttgaaat ctggaactgc ctctgttgtg    480
tgcctgctga ataacttcta tcccagagag gccaaagtac agtggaaggt ggataacgcc   540
ctccaatcgg gtaactccca ggagagtgtc acagagcagg acagcaagga cagcaccctac  600
agcctcagca gcaccctgac gctgagcaaa gcagactacg agaaacacaa agtctacgcc    660
tgcgaagtca cccatcaggg cctgagctcg cccgtcacaa agagcttcaa caggggagag   720
tgttagtag                                                           729
```

<210> SEQ ID NO 90
<211> LENGTH: 20
<212> TYPE: DNA
<213> ORGANISM: Artificial Sequence
<220> FEATURE:
<223> OTHER INFORMATION: Wild type Internal Ribosome Entry Site (IRES)

<400> SEQUENCE: 90

```
atgataatat ggccacaacc                                                20
```

<210> SEQ ID NO 91
<211> LENGTH: 1407

<212> TYPE: DNA
<213> ORGANISM: Artificial Sequence
<220> FEATURE:
<223> OTHER INFORMATION: Heavy chain of antibody GA101 (HC 1329-2747)

<400> SEQUENCE: 91

```
atggagtttg ggctgagctg ggttttcctc gttgctcttt ttagaggtgt ccagtgtcag      60
gtgcagctgg tgcagtctgg ggctgaggtg aagaagcctg gtcctccgt gaaggtctcc     120
tgcaaggcct ctggatacgc cttctcctac tcttggatca actgggtgcg acaggcccct    180
ggacaagggc tcgagtggat gggacggatc ttccctggcg atggtgacac agactacaac    240
ggcaagttca agggcagagt caccatcacc gccgacaagt ccacgagcac agcctacatg    300
gaactgagca gcctgagatc tgaggacacg gccgtctatt actgtgcacg aaacgtgttc    360
gatggctatt ggctggtgta ctggggccag ggaccctgg tcaccgtcag cagcgctagc     420
accaagggcc catcggtctt ccccctggca ccctcctcca gagcacctc tggggcaca      480
gcggccctgg gctgcctggt caaggactac ttccccgaac cggtgacggt gtcatggaac    540
tcaggcgccc tgaccagcgg cgtgcacacc ttcccggctg tcctacagtc ctcaggactc    600
tactccctca gcagcgtggt gaccgtgccc tccagcagct gggcaccca gacctacatc     660
tgcaacgtga atcacaagcc cagcaacacc aaggtggaca agaaagttga gcccaaatct    720
tgtgacaaaa ctcacacatg cccaccgtgc ccagcacctg aactcctggg gggaccgtca    780
gtcttcctct tccccccaaa acccaaggac accctcatga tctcccggac ccctgaggtc    840
acatgcgtgg tggtggacgt gagccacgaa gaccctgagg tcaagttcaa ctggtacgtg    900
gacggcgtgg aggtgcataa tgccaagaca agccgcggg aggagcagta caacagcacg     960
taccgtgtgg tcagcgtcct caccgtcctg caccaggact ggctgaatgg caaggagtac   1020
aagtgcaagg tctccaacaa agccctccca gcccccatcg agaaaaccat ctccaaagcc   1080
aaagggcagc cccgagaacc acaggtgtac accctgcccc catcccggga tgagctgacc   1140
aagaaccagg tcagcctgac ctgcctggtc aaaggcttct atcccagcga catcgccgtg   1200
gagtgggaga gcaatgggca gccggagaac aactacaaga ccacgcctcc cgtgctggac   1260
tccgacggct ccttcttcct ctacagcaag ctcaccgtgg acaagagcag gtggcagcag   1320
gggaacgtct tctcatgctc cgtgatgcat gaggctctgc acaaccacta cacgcagaag   1380
agcctctccc tgtctccggg taaatga                                        1407
```

<210> SEQ ID NO 92
<211> LENGTH: 594
<212> TYPE: DNA
<213> ORGANISM: Artificial Sequence
<220> FEATURE:
<223> OTHER INFORMATION: Attenuated Internal Ribosome Entry Site (attIRES)

<400> SEQUENCE: 92

```
accggtgccc ctctccctcc ccccccccta acgttactgg ccgaagccgc ttggaataag      60
gccggtgtgc gtttgtctat atgttatttt ccaccatatt gccgtctttt ggcaatgtga    120
gggcccggaa acctggccct gtcttcttga cgagcattcc tagggtctt tcccctctcg     180
ccaaaggaat gcaaggtctg ttgaatgtcg tgaaggaagc agttcctctg gaagcttctt    240
gaagacaaac aacgtctgta gcgaccctt gcaggcagcg gaaccccca cctggcgaca     300
ggtgcctctg cggccaaaag ccacgtgtat aagatacacc tgcaaaggcg gcacaacccc    360
agtgccacgt tgtgagttgg atagttgtgg aaagagtcaa atggctctcc tcaagcgtat    420
```

```
tcaacaaggg gctgaaggat gcccagaagg tacccccattg tatgggatct gatctggggc    480
ctcggtacac atgctttaca tgtgtttagt cgaggttaaa aaaacgtcta ggccccccga    540
accacgggga cgtggttttc ctttgaaaaa cacgatgata agcttgccac aacc          594
```

```
<210> SEQ ID NO 93
<211> LENGTH: 23
<212> TYPE: DNA
<213> ORGANISM: Artificial Sequence
<220> FEATURE:
<223> OTHER INFORMATION: Attenuation stretch

<400> SEQUENCE: 93
```

```
ccgggagatg aggatcgttt cgc                                             23
```

```
<210> SEQ ID NO 94
<211> LENGTH: 1122
<212> TYPE: DNA
<213> ORGANISM: Artificial Sequence
<220> FEATURE:
<223> OTHER INFORMATION: Glutamine Synthetase (GS) having R324C mutation

<400> SEQUENCE: 94
```

```
atggccacct cagcaagttc ccacttgaac aaaaacatca agcaaatgta cttgtgcctg     60
ccccagggtg agaaagtcca agccatgtat atctgggttg atggtactgg agaaggactg    120
cgctgcaaaa cccgcacccct ggactgtgag cccaagtgtg tagaagagtt acctgagtgg   180 aatttttgatg gctctagtac ctttcagtct gagggctcca acagtgacat gtatctcagc   240
cctgttgcca tgtttcggga ccccttccgc agagatccca acaagctggt gttctgtgaa    300
gttttcaagt acaaccggaa gcctgcagag accaatttaa ggcactcgtg taaacggata    360
atggacatgg tgagcaacca gcaccccctgg tttggaatgg aacaggagta tactctgatg   420
ggaacagatg gcacccctttt tggttggcct tccaatggct ttcctgggcc ccaaggtccg   480
tattactgtg gtgtgggcgc agacaaagcc tatggcaggg atatcgtgga ggctcactac   540
cgcgcctgct tgtatgctgg ggtcaagatt acaggaacaa atgctgaggt catgcctgcc   600
cagtgggaat tccaaatagg accctgtgaa ggaatccgca tgggagatca tctctgggtg   660
gcccgtttca tcttgcatcg agtatgtgaa gactttgggg taatagcaac ctttgacccc    720
aagcccattc ctgggaactg gaatggtgca ggctgccata ccaactttag caccaaggcc   780
atgcgggagg agaatggtct gaagcacatc gaggaggcca tcgagaaact aagcaagcgg   840
caccggtacc acattcgagc ctacgatccc aaggggggcc tggacaatgc ccgtcgtctg    900
actgggttcc acgaaacgtc caacatcaac gactttttctg ctggtgtcgc caatcgcagt    960
gccagcatct gcattccccg gactgtcggc caggagaaga aggttacttt gaagaccgc    1020 cgcccctctg ccaattgtga cccctttgca gtgacagaag ccatcgtccg cacatgcctt   1080
ctcaatgaga ctggcgacga gcccttccaa tacaaaaact aa                      1122
```

```
<210> SEQ ID NO 95
<211> LENGTH: 159
<212> TYPE: DNA
<213> ORGANISM: Artificial Sequence
<220> FEATURE:
<223> OTHER INFORMATION: pcDNA sequence between neo and SV40pA

<400> SEQUENCE: 95
```

```
ttcgaaatga ccgaccaagc gacgcccaac ctgccatcac gagatttcga ttccaccgcc     60
```

| gccttctatg aaaggttggg cttcggaatc gttttccggg acgccggctg gatgatcctc | 120 |
| cagcgcgggg atctcatgct ggagttcttc gcccacccc | 159 |

<210> SEQ ID NO 96
<211> LENGTH: 131
<212> TYPE: DNA
<213> ORGANISM: Artificial Sequence
<220> FEATURE:
<223> OTHER INFORMATION: SV40 pA terminator sequence (SV40pA)

<400> SEQUENCE: 96

| aacttgttta ttgcagctta taatggttac aaataaagca atagcatcac aaatttcaca | 60 |
| aataaagcat ttttttcact gcattctagt tgtggtttgt ccaaactcat caatgtatct | 120 |
| tatcatgtct g | 131 |

<210> SEQ ID NO 97
<211> LENGTH: 382
<212> TYPE: DNA
<213> ORGANISM: Artificial Sequence
<220> FEATURE:
<223> OTHER INFORMATION: Corresponding region with pcDNA3.1

<400> SEQUENCE: 97

| tataccgtcg acctctagct agagcttggc gtaatcatgg tcatagctgt ttcctgtgtg | 60 |
| aaattgttat ccgctcacaa ttccacacaa catacgagcc ggaagcataa agtgtaaagc | 120 |
| ctggcgcgcc taatgagtga gctaactcac attaattgcg ttgcgctcac tgcccgcttt | 180 |
| ccagtcggga aacctgtcgt gccagctgca ttaatgaatc ggcgatcgcg cggggagagg | 240 |
| cggtttgcgt attgggcgct cttccgcttc ctcgctcact gactcgctgc gctcggtcgt | 300 |
| tcggctgcgg cgagcggtat cagctcactc aaaggcggta atacggttat ccacagaatc | 360 |
| aggggataac gcaggaaaga ac | 382 |

<210> SEQ ID NO 98
<211> LENGTH: 671
<212> TYPE: DNA
<213> ORGANISM: Artificial Sequence
<220> FEATURE:
<223> OTHER INFORMATION: PUC origin

<400> SEQUENCE: 98

| atgtgagcaa aaggccagca aaaggccagg aaccgtaaaa aggccgcgtt gctggcgttt | 60 |
| ttccataggc tccgcccccc tgacgagcat cacaaaaatc gacgctcaag tcagaggtgg | 120 |
| cgaaacccga caggactata agataccag gcgtttcccc ctggaagctc cctcgtgcgc | 180 |
| tctcctgttc cgaccctgcc gcttaccgga tacctgtccg cctttctccc ttcgggaagc | 240 |
| gtggcgcttt ctcatagctc acgctgtagg tatctcagtt cggtgtaggt cgttcgctcc | 300 |
| aagctgggct gtgtgcacga acccccgtt cagcccgacc gctgcgcctt atccggtaac | 360 |
| tatcgtcttg agtccaaccc ggtaagacac gacttatcgc cactggcagc agccactggt | 420 |
| aacaggatta gcagagcgag gtatgtaggc ggtgctacag agttcttgaa gtggtggcct | 480 |
| aactacggct acactagaag aacagtattt ggtatctgcg ctctgctgaa gccagttacc | 540 |
| ttcggaaaaa gagttggtag ctcttgatcc ggcaaacaaa ccaccgctgg tagcggtttt | 600 |
| tttgtttgca agcagcagat tacgcgcaga aaaaaaggat ctcaagaaga tcctttgatc | 660 |
| ttttctacgg g | 671 |

```
<210> SEQ ID NO 99
<211> LENGTH: 144
<212> TYPE: DNA
<213> ORGANISM: Artificial Sequence
<220> FEATURE:
<223> OTHER INFORMATION: Corresponding region with pcDNA3.1

<400> SEQUENCE: 99
gtctgacgct cagtggaacg aaaactcacg ttaagggatt ttggtcatga gattatcaaa    60
aaggatcttc acctagatcc ttttaaatta aaaatgaagt tttaaatcaa tctaaagtat   120
atatgagtaa acttggtctg acag                                          144

<210> SEQ ID NO 100
<211> LENGTH: 861
<212> TYPE: DNA
<213> ORGANISM: Artificial Sequence
<220> FEATURE:
<223> OTHER INFORMATION: Ampicillin (Amp) resistance gene on
      complementary strand

<400> SEQUENCE: 100
ttaccaatgc ttaatcagtg aggcacctat ctcagcgatc tgtctatttc gttcatccat    60
agttgcctga ctccccgtcg tgtagataac tacgatacgg gagggcttac catctggccc   120
cagtgctgca atgataccgc gagacccacg ctcaccggct ccagatttat cagcaataaa   180
ccagccagcc ggaagggccg agcgcagaag tggtcctgca actttatccg cctccatcca   240
gtctattaat tgttgccggg aagctagagt aagtagttcg ccagttaata gtttgcgcaa   300
cgttgttgcc attgctacag gcatcgtggt gtcacgctcg tcgtttggta tggcttcatt   360
cagctccggt tcccaacgat caaggcgagt tacatgatcc cccatgttgt gcaaaaaagc   420
ggttagctcc ttcggtcctc cgatcgttgt cagaagtaag ttggccgcag tgttatcact   480
catggttatg gcagcactgc ataattctct tactgtcatg ccatccgtaa gatgcttttc   540
tgtgactggt gagtactcaa ccaagtcatt ctgagaatag tgtatgcggc gaccgagttg   600
ctcttgcccg gcgtcaatac gggataatac cgcgccacat agcagaactt taaaagtgct   660
catcattgga aaacgttctt cggggcgaaa actctcaagg atcttaccgc tgttgagatc   720
cagttcgatg taacccactc gtgcacccaa ctgatcttca gcatctttta ctttcaccag   780
cgtttctggg tgagcaaaaa caggaaggca aaatgccgca aaaaagggaa taagggcgac   840
acggaaatgt tgaatactca t                                            861

<210> SEQ ID NO 101
<211> LENGTH: 136
<212> TYPE: DNA
<213> ORGANISM: Artificial Sequence
<220> FEATURE:
<223> OTHER INFORMATION: beta-Lactamase (bla) promoter

<400> SEQUENCE: 101
actcttcctt tttcaatatt attgaagcat ttatcagggt tattgtctca tgagcggata    60
catatttgaa tgtatttaga aaaataaaca ataggggtt ccgcgcacat ttccccgaaa    120
agtgccacct gacgtc                                                   136

<210> SEQ ID NO 102
<211> LENGTH: 1122
<212> TYPE: DNA
<213> ORGANISM: Cricetulus griseus

<400> SEQUENCE: 102
```

```
atggccacct cagcaagttc ccacttgaac aaaggcatca agcaaatgta catgtccctg    60
ccccagggtg agaaagtcca agccatgtat atctgggttg atggtaccgg agaaggactg   120
cgctgcaaaa cccgcaccct ggactgtgag cccaagtgtg tagaagagtt acctgagtgg   180
aattttgatg gctctagtac ctttcagtct gagggctcca acagtgacat gtatctcagc   240
cctgttgcca tgtttcggga ccccttccgc aaagagccca acaagctggt gttctgtgaa   300
gtcttcaagt acaaccggaa gcctgcagag accaatttaa gacacacgtg taaacggata   360
atggacatgg tgagcaacca gcaccctggt ttggaatgg aacaggagta tactctcttg   420
ggaacagatg gcacccttt tggttggcct tccgatggct ccctgggcc caaggtctg    480
tattactgtg gtgtgggcgc agacaaagcc tatcgcaggg atatcatgga ggctcactac   540
cttgcctgct gtatgctgg ggtcaagatt acaggaacat atgctgaggt caagcatgcc   600
cagtgggaat tccaaatagg accctgtgaa ggaatccgca tgggagatca tctgtgggtg   660
gcccgtttca tcttgcatcg agtatgtaaa gactttgggg taatagcaac ctttgacccc   720
aagcccattc ctgggaactg gaatggtgca ggctgccata ccaactttag taccaagacc   780
atgcgggagg agaatggtct gaagcacatc aaggaggcca ttgagaaact aagcaagcgg   840
caccggtacc atattcgagc ctacgatccc aaggggggc tggacaatgc ccgtcgtctg   900
actgggttcc acaaaacgtc caacatcaac gactttccag ctggcgtcgc cgatcgcagt   960
gccagcatcc gcattccccg gactgtcggc caggagaaga aaggttactt tgaagcccgc  1020
tgccctctg ccaattgtga ccctttgca gtgacagaag ccatcgtccg cacatgcctt  1080
ctcaatgaga ctggcgacga gcccttccaa tacaaaaact aa                    1122
```

<210> SEQ ID NO 103
<211> LENGTH: 373
<212> TYPE: PRT
<213> ORGANISM: Cricetulus griseus

<400> SEQUENCE: 103

Met Ala Thr Ser Ala Ser Ser His Leu Asn Lys Gly Ile Lys Gln Met
1               5                   10                  15

Tyr Met Ser Leu Pro Gln Gly Glu Lys Val Gln Ala Met Tyr Ile Trp
                20                  25                  30

Val Asp Gly Thr Gly Glu Gly Leu Arg Cys Lys Thr Arg Thr Leu Asp
            35                  40                  45

Cys Glu Pro Lys Cys Val Glu Glu Leu Pro Glu Trp Asn Phe Asp Gly
        50                  55                  60

Ser Ser Thr Phe Gln Ser Glu Gly Ser Asn Ser Asp Met Tyr Leu Ser
65                  70                  75                  80

Pro Val Ala Met Phe Arg Asp Pro Phe Arg Lys Glu Pro Asn Lys Leu
                85                  90                  95

Val Phe Cys Glu Val Phe Lys Tyr Asn Arg Lys Pro Ala Glu Thr Asn
            100                 105                 110

Leu Arg His Thr Cys Lys Arg Ile Met Asp Met Val Ser Asn Gln His
        115                 120                 125

Pro Trp Phe Gly Met Glu Gln Glu Tyr Thr Leu Leu Gly Thr Asp Gly
    130                 135                 140

His Pro Phe Gly Trp Pro Ser Asp Gly Phe Pro Gly Pro Gln Gly Leu
145                 150                 155                 160

Tyr Tyr Cys Gly Val Gly Ala Asp Lys Ala Tyr Arg Arg Asp Ile Met
                165                 170                 175

-continued

```
Glu Ala His Tyr Leu Ala Cys Leu Tyr Ala Gly Val Lys Ile Thr Gly
            180                 185                 190

Thr Tyr Ala Glu Val Lys His Ala Gln Trp Glu Phe Gln Ile Gly Pro
        195                 200                 205

Cys Glu Gly Ile Arg Met Gly Asp His Leu Trp Val Ala Arg Phe Ile
    210                 215                 220

Leu His Arg Val Cys Lys Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Thr Met Arg Glu Glu Asn Gly Leu Lys His Ile Lys Glu
            260                 265                 270

Ala Ile Glu Lys Leu Ser Lys Arg His Arg Tyr His Ile Arg Ala Tyr
            275                 280                 285

Asp Pro Lys Gly Gly Leu Asp Asn Ala Arg Arg Leu Thr Gly Phe His
        290                 295                 300

Lys Thr Ser Asn Ile Asn Asp Phe Ser Ala Gly Val Ala Asp Arg Ser
305                 310                 315                 320

Ala Ser Ile Arg Ile Pro Arg Thr Val Gly Gln Glu Lys Lys Gly Tyr
                325                 330                 335

Phe Glu Ala Arg Cys Pro Ser Ala Asn Cys Asp Pro Phe Ala Val Thr
            340                 345                 350

Glu Ala Ile Val Arg Thr Cys Leu Leu Asn Glu Thr Gly Asp Glu Pro
            355                 360                 365

Phe Gln Tyr Lys Asn
370
```